(12) United States Patent
Giardina et al.

(10) Patent No.: US 6,743,804 B2
(45) Date of Patent: Jun. 1, 2004

(54) QUINOLINE DERIVATIVES AS NK3 ANTAGONISTS

(75) Inventors: Giuseppe Arnaldo Maria Giardina, Milan (IT); Carlo Farina, Milan (IT); Mario Grugni, Verbania (IT); Luca Francesco Raveglia, Milan (IT)

(73) Assignee: SmithKline Beecham S p.A., Milan (IT)

( * ) Notice: Subject to any disclaimer, the term of this patent is extended or adjusted under 35 U.S.C. 154(b) by 0 days.

(21) Appl. No.: 10/140,452

(22) Filed: May 7, 2002

(65) Prior Publication Data

US 2003/0195204 A1 Oct. 16, 2003

Related U.S. Application Data

(63) Continuation of application No. 09/077,156, filed as application No. PCT/EP96/05209 on Nov. 22, 1996, now abandoned.

(51) Int. Cl.[7] ................................................. A62K 31/47
(52) U.S. Cl. ......................... 514/311; 514/314; 514/912
(58) Field of Search ................................. 514/311, 314, 514/912

(56) References Cited

U.S. PATENT DOCUMENTS 5,538,982 A  *  7/1996  Hagan et al. ................ 514/305

FOREIGN PATENT DOCUMENTS

| EP | 0 112 776 | 7/1984 |
| EP | 0 585 913 | 3/1994 |
| EP | 0 652 218 | 5/1995 |
| WO | WO 95 32948 | 12/1995 |
| WO | WO 96 02509 | 2/1996 |

* cited by examiner

Primary Examiner—Zohreh Fay
(74) Attorney, Agent, or Firm—Nora Stein-Fernandez; Theodore R. Furman

(57) ABSTRACT

The present invention relates to a novel use, in particular a novel pharmaceutical use for a series of quinoline derivatives.

1 Claim, No Drawings

QUINOLINE DERIVATIVES AS NK3 ANTAGONISTS

This application is a continuation of U.S. Ser. No. 09/077,156 filed on May 21, 1988, now abandoned, which is a 371 of PCT/EP96/05209, filed Nov. 22, 1996.

The present invention relates to a novel use, in particular a novel pharmaceutical use for a series of quinoline derivatives.

The mammalian peptide Neurokinin B (NKB) belongs to the Tachykinin (TK) peptide family which also include Substance P (SP) and Neurokinin A (NKA). Pharmacological and molecular biological evidence has shown the existence of three subtypes of TK receptor ($NK_1$, $NK_2$ and $NK_3$) and NKB binds preferentially to the $NK_3$ receptor although it also recognises the other two receptors with lower affinity (Maggi et al , 1993, *J. Auton. Pharmacol.*, 13, 23–93).

Selective peptidic $NK_3$ receptor antagonists are known (Drapeau, 1990 *Regul. Pept.*, 31, 125–135), and findings with peptidic $NK_3$ receptor agonists suggest that NKB, by activating the $NK_3$ receptor, has a key role in the modulation of neural input in airways, skin, spinal cord and nigrostriatal pathways (Myers and Undern, 1993, *J. Phisiol.*, 470, 665–679; Counture et al., 1993, *Regul. Peptides*, 46, 426–429; Mccarson and Krause, 1994, *J. Neurosci.*, 14 (2), 712–720; Arenas et al. 1991, *J. Neurosci.*, 11, 2332–8).

International Patent Application Number PCT/EP95/02000 describes certain quinoline derivatives, the preparation of the quinolines and their use in medicine. The disclosures of PCT/EP95/02000 are relevant to the present application only by virtue of Article 54(3) of the European Patent Convention.

We have now discovered certain novel uses for the compounds of PCT/EP95/02000 in particular use in the prevention and treatment of certain conditions characterized by overstimulation of the thachykinin receptors, in particular NK-3 receptors. Such conditions include disorders of the central nervous system, such as schizophrenia; neurodegenerative disorders, such as aids related dementia, senile dementia of the Alzheimer type and Down's syndrome; demyelinating diseases such as multiple sclerosis and other neuropathological disorders such as diabetic or peripheral neuropathy, AIDS related neuropathy, chemotherapy-induced neuropathy and neuralgia; respiratory diseases such as, bronchopneumonia and bronchospasm; inflammatory diseases such as inflammatory bowel disease, fibrositis, osteoarthritis, rheumatoid arthritis; allergies such as eczema and rhinitis; hypersensivity disorders such as poison ivy; ophthalmic diseases such as conjunctivitis, vernal conjuctivitis and the like; cutaneous diseases such as contact dermatitis, urticaria and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancment or suppression such as systhemic lupus erythematosis; gastrointestinal (GI) disorders and diseases of the GI tract such as disorders associated with the neuronal control of viscera such as ulcerative colitis, Crohn's disease; disorders of the bladder function; fibrosing and collagen diseases such as scleroderma and eosinophilic fascioliasis; disorders of the blood flow caused by vasodilation and vasospastic diseases such as angina, migraine and Reynaud's disease; pain or nociception, for example, that is attributable to or associated with any of the foregoing conditions especially the transmission of pain in migraine, (herein also referred to as the 'Conditions of the invention'). It will be appreciated that the Conditions of the invention do not include the conditions disclosed in WO PCT/EP95/02000.

Accordingly, the present invention provides a method for the treatment and or prophylaxis of conditions characterized by overstimulation of the thachykinin receptors, in particular NK-3 receptors, which method comprises the administration to a mammal in need thereof, of an effective, non-toxic, pharmaceutically acceptable amount of a compound of formula (I):

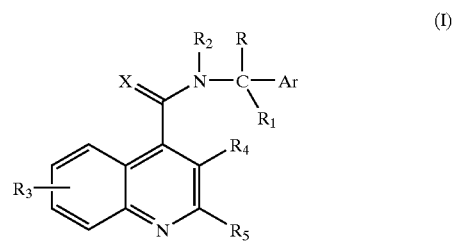

or a pharmaceutically acceptable solvate thereof, or a pharmaceutically acceptable salt thereof, wherein:

Ar is an optionally substituted phenyl, naphthyl or $C_{5-7}$ cycloalkdienyl group, or an optionally substituted single or fused ring heterocyclic group, having aromatic character, containing from 5 to 12 ring atoms and comprising up to four hetero-atoms in the or each ring selected from S, O, N;

R is linear or branched $C_{1-8}$ alkyl, $C_{3-7}$ cycloalkyl, $C_{4-7}$ cycloalkylalkyl, optionally substituted phenyl or phenyl $C_{1-6}$ alkyl, an optionally substituted five-membered heteroaromatic ring comprising up to four heteroatom selected from O and N, hydroxy $C_{1-6}$ alkyl, amino $C_{1-6}$ alkyl, $C_{1-6}$ alkylaminoalkyl, di $C_{1-6}$ alkylaminoalkyl, $C_{1-6}$ acylaminoalkyl, $C_{1-6}$ alkoxyalkyl, $C_{1-6}$ alkylcarbonyl, carboxy, $C_{1-6}$ alkoxyxcarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl, halogeno $C_{1-6}$ alkyl; or is a group —$(CH_2)_p$— when cyclized onto Ar, where p is 2 or 3.

$R_1$ and $R_2$, which may be the same or different, are independently hydrogen or $C_{1-6}$ linear or branched alkyl, or together form a —$(CH_2)$n-group in which n represents 3, 4, or 5; or $R_1$ together with R forms a group —$(CH_2)_q$—, in which q is 2, 3, 4 or 5;

$R_3$ and $R_4$, which may be the same or different, are independently hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, $C_{1-6}$ alkoxycarbonyl, trifluoromethyl, acyloxy, phthalimido, amino, mono- and di-$C_{1-6}$ alkylamino, —$O(CH_2)_r$—$NT_2$, in which r is 2, 3, or 4 and T is hydrogen or $C_{1-6}$ alkyl or it forms with the adjacent nitrogen a group

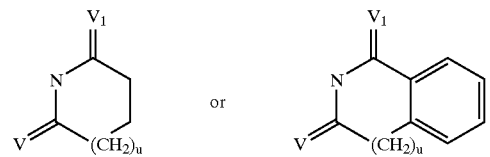

in which V and $V_1$ are independently hydrogen or oxygen and u is 0, 1 or 2;

—$O(CH_2)_s$—OW in which s is 2, 3, or 4 and W is hydrogen or $C_{1-6}$ alkyl;

hydroxyalkyl, aminoalkyl, mono- or di-alkylaminoalkyl, acylamino, alkylsulphonylamino, aminoacylamino, mono- or di-alkylaminoacylamino; with up to four $R_3$ substituents being present in the quinoline nucleus;

or $R_4$ is a group —$(CH_2)_t$— when cyclized onto $R_5$ as aryl, in which t is 1, 2, or 3;

$R_5$ is branched or linear $C_{1-6}$ alkyl, $C_{3-7}$ cycloalkyl, $C_{4-7}$ cycloalkylalkyl, optionally substituted aryl, or an optionally substituted single or fused ring heterocyclic group, having aromatic character, containing from 5 to 12 ring atoms and comprising up to four hetero-atoms in the or each ring selected from S, O, N;

X is O, S, or N—C≡N.

Suitable mammals are humans.

Suitable conditions for prevention and treatment characterized by overstimulation of the thachykinin receptors, in particular NK-3 receptors are the Conditions of the Invention described above.

Favoured conditions for prevention and treatment are disorders of the central nervous system, such as schizophrenia; neuropathological disorders such as diabetic or peripheral neuropathy; respiratory diseases such as, bronchopneumonia and bronchospasm; inflammatory diseases such as inflammatory bowel disease, fibrositis, osteoarthritis, rheumatoid arthritis allergies such as eczema and rhinitis; ophthalmic diseases such as conjunctivitis, vernal conjuctivitis and the like; cutaneous diseases such as contact dermatitis, urticaria and other eczematoid dermatitis; gastrointestinal (GI) disorders and diseases of the GI tract such as disorders associated with the neuronai control or viscera such as ulcerative colitis, Crohn's disease; disorders of the bladder function; pain or nociception, for example, that is attributable to or associated with any of the foregoing conditions especially the transmission of pain in migraine.

A suitable inflamatory disease for prevention and treatment is inflammatory bowel disease.

A suitable ophthalmic disease for prevention and treatment is conjunctivitis.

Suitable disorders and diseases of the GI tract for prevention and treatment are disorders associated with the neuronal control of viscera such as ulcerative colitis.

Preferred conditions for prevention and treatment are respiratory diseases such as, bronchopneumonia and bronchospasm; inflammatory diseases such as inflammatory bowel disease; allergies such as eczema and rhinitis; ophthalmic diseases such as conjunctivitis; cutaneous diseases such as contact dermatitis and urticaria; gastrointestinal (GI) disorders and diseases of the GI tract; disorders of the bladder function; pain or nociception, especially the transmission of pain in migraine.

Examples of Ar are phenyl, optionally substituted by hydroxy, halogen, $C_{1-6}$ alkoxy or $C_{1-6}$ alkyl. Examples of halogen are chlorine and fluorine, an example of $C_{1-6}$ alkoxy is methoxy and an example of $C_{1-6}$ alkyl is methyl.

Examples of Ar as a heterocyclic group are thienyl and pyridyl.

Examples of Ar as a $C_{5-7}$ cycloalkdienyl group is cyclohexadienyl.

Examples of R are as follows:

$C_{1-8}$ alkyl: methyl, ethyl, n-propyl, iso-propyl, n-butyl, heptyl;

phenyl $C_{1-6}$ alkyl: benzyl;

hydroxy $C_{1-6}$ alkyl: —$CH_2OH$, —$CH_2CH_2OH$, $CH(Me)OH$;

amino $C_{1-6}$ alkyl: —$CH_2NH_2$;

di $C_{1-6}$ alkylaminoalkyl: —$CH_2NMe_2$;

$C_{1-6}$ alkoxyalkyl: $CH_2OMe$;

$C_{1-6}$ alkylcarbonyl: $COMe$;

$C_{1-6}$ alkoxycarbonyl: $COOMe$;

$C_{1-6}$ alkoxycarbonyl $C_{1-6}$ alkyl: $CH_2COOMe$;

$C_{1-6}$ alkylaminocarbonyl: $CONHMe$;

di $C_{1-6}$ alkylaminocarbonyl: $CONMe_2$, $CO(1$-pyrrolidinyl);

halogen $C_{1-6}$ alkyl: trifluoromethyl;

—$(CH_2)_p$— when cyclized onto Ar:

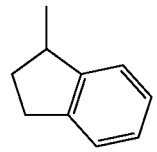

Example of $R_1$ and $R_2$ as $C_{1-6}$ alkyl is methyl; example of $R_1$ together with R forming a group-$(CH_2)_q$— is spirocyclopentane.

Examples of $R_3$ and $R_4$ are methyl, ethyl, n-propyl, n-butyl, methoxy, hydroxy, amino, chlorine, fluorine, bromine, acetyloxy, 2-(dimetylamino)ethoxy, 2-(phthalimido)ethoxy, aminoethoxy, 2-(1-pyrrolidinyl)ethoxy, phthalimido, dimethylaminopropoxy, dimethylaminoacetylamino, acetylamino, dimethylaminomethyl and phenyl.

Examples of $R_5$ are cyclohexyl, phenyl optionally substituted as defined for Ar above; examples of $R_5$ as a heterocyclic group are furyl, thienyl, pyrryl, thiazolyl, benzofuryl and pyridyl.

A preferred group of compounds of formula (I) are those in which:

Ar is phenyl, optionally substituted by $C_{1-6}$ alkyl or halogen; thienyl or a $C_{5-7}$ cycloalkdienyl group;

R is $C_{1-6}$ alkyl, $C_{1-6}$ alkoxycarbonyl, $C_{1-6}$ alkylcarbonyl, hydroxy $C_{1-6}$ alkyl;

$R_1$ and $R_2$ are each hydrogen or $C_{1-6}$ alkyl;

$R_3$ is hydrogen, hydroxy, halogen, $C_{1-6}$ alkoxy, $C_{1-6}$ alkyl;

$R_4$ is hydrogen, $C_{1-6}$ alkyl, $C_{1-6}$ alkoxy, hydroxy, amino, halogen, aminoalkoxy, mono- or di-alkylaminoalkoxy, mono- or di-alkylaminoalkyl, phthalimidoalkoxy, mono- or di-alkylaminoacylamino and acylamino;

$R_5$ is phenyl, thienyl, furyl, pyrryl and thiazolyl.

A further preferred group of compounds of formula (I) are those in which:

Ar is phenyl, 2-chlorophenyl, 2-thienyl or cyclohexadienyl;

R is methyl, ethyl, n-propyl, —COOMe, —COMe;

$R_1$ and $R_2$ are each hydrogen or methyl;

$R_3$ is hydrogen, methoxy, or hydroxy;

$R_4$ is hydrogen, methyl, ethyl, methoxy, hydroxy, amino, chlorine, bromine, dimethylaminoethoxy, 2-(phthalimido)ethoxy, aminoethoxy, 2-(1-pyrrolidinyl)ethoxy, dimethylaminopropoxy, dimethylaminoacetylamino, acetylamino, and dimethylaminomethyl.

$R_5$ is phenyl, 2-thienyl, 2-furyl, 2-pyrryl, 2-thiazolyl and 3-thienyl; and X is oxygen.

A preferred sub-group of compounds within the scope of formula (I) above is of formula (Ia):

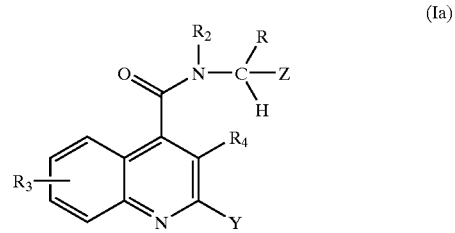

(Ia)

in which:

R, $R_2$, $R_3$ and $R_4$ are as defined in formula (I), and Y and Z, which may be the same or different, are each Ar as defined in formula (I).

A particularly preferred group of compounds of formula (Ia) are those of formula (Ib) in which the group R is oriented downward and H upward.

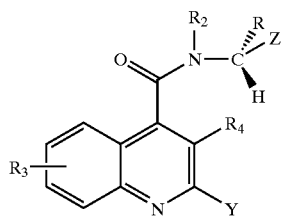

(Ib)

The compounds of formula (I) or their salts or solvates are in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in pharmaceutical composition. In the case of salts and solvates the additional ionic and solvent moieties must also be non-toxic.

Examples of pharmaceutically acceptable salts of a compound of formula (D) include the acid addition salts with the conventional pharmaceutical acids, for example maleic, hydrochloric, hydrobromic, phosphoric, acetic, fumaric, salicylic, citric, lactic, mandelic, tartaric, succinic, benzoic, ascorbic, and methanesulphonic.

Examples of pharmaceutically acceptable solvates of a compound of formula (I) include hydrates.

The compounds of formula (I) may have at least one asymmetric center and therefore may exist in more than one stereoisomeric form. The treatment of the invention extends to all such forms and to mixtures thereof, including racemates.

A compound of formula (I) is prepared by reacting a compound of formula (III)

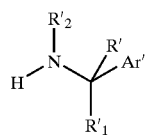

(III)

in which R', R'$_1$, R'$_2$ and Ar' are R, R$_1$, R$_2$ and Ar as defined for formula (I) or a group or atom convertible to R, R$_1$, R$_2$ and Ar, with a compound of formula (II)

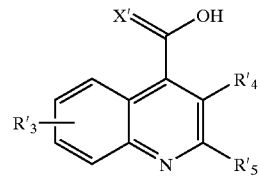

(II)

or an active derivative thereof, in which R'$_3$, R'$_4$, R'$_5$ and X' are R$_3$, R$_4$, R$_5$ and X as defined for formula (I) or a group convertible to R$_3$, R$_4$, R$_5$ and X, to form a compound of formula (Ic)

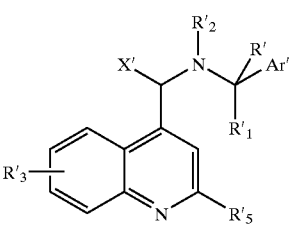

(Ic)

and optionally thereafter performing one or more of the following steps:

(a) where R', R'$_1$ to R'$_5$, Ar' and X' are other than R, R$_1$ to R$_5$, Ar and X, converting any one of R', R'$_1$, to R'$_5$, Ar' and X' to R, R$_1$ to R$_5$, Ar and X to obtain a compound of formula (I), (b) where R', R'$_1$ to R'$_5$, Ar' and X' are R, R$_1$ to R$_5$, Ar and X, converting any one of R, R$_1$ to R$_5$, Ar and X to another R, R$_1$ to R$_5$, Ar and X, to obtain a compound of formula (I), (c) forming a salt and/or solvate of the obtained compound of formula (Ic).

Suitable active derivatives of the compounds of formula (II) are acid halides (preferably chlorides), acid azides or acid anhydrides. Another suitable derivative is a mixed anhydride formed between the acid and an alkyl chloroformate; another suitable derivative is an activated ester such as a cyanomethyl ester, thiophenyl ester, p-nitrophenyl ester, p-nitrothiophenyl ester, 2,4,6-trichlorophenyl ester, pentachlorophenyl ester, pentafluorophenyl ester, N-hydroxyphtalimido ester, N-hydroxypiperidine ester, N-hydroxysuccinimide ester, N-hydroxy benzotriazole ester; or the carboxy group may be activated using a carbodiimide or N,N'-carbonyldiimidazole.

For example, in standard methods well known to those skilled in the art, the compounds of formula (III) may be coupled:

(a) with an acid chloride in the presence of an inorganic or organic base in a suitable aprotic solvent such as dimethylformamide (DMF) at a temperature in a range from −70 to 50° C. (preferably in a range from −10 to 20° C.), (b) with the acid in the presence of a suitable condensing agent, such as for example N,N'-carbonyl diimidazole (CDI) or a carbodiimide such as dicyclohexylcarbodiimide (DCC) or N-dimethylaminopropyl-N'-ethylcarbodiimide and N-hydroxybenzotriazole (HOBT) to maximise yields and avoid racemization processes (*Synthesis*, 453, 1972) in an aprotic solvent such as a mixture of acetonitrile (MeCN) and tetrahydrofuran (THF) in a ratio from 1:9 to 7:3, respectively, at a temperature in a range from −70 to 50° C. (preferably in a range from −10 to 25° C.) (see Scheme 1), Scheme 1

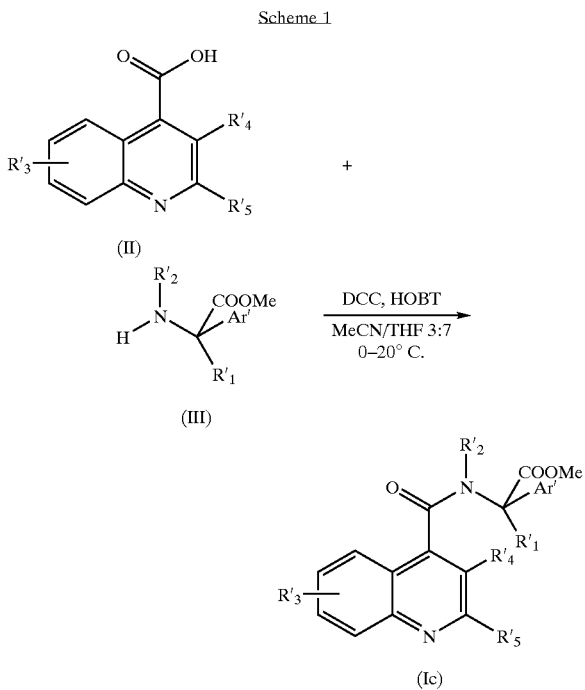

(c) with a mixed anhydride generated in situ from the acid and an alkyl (for example isopropyl) chloroformate in a suitable aprotic solvent such as dichloromethane at a temperature in a range from −70 to 50° C. (preferably in a range from −20 to 20° C.).

It will be appreciated that a compound of formula (Ic) may be converted to a compound of formula (I), or one compound of formula (I) may be converted to another compound of formula (I), by interconversion of suitable substituents. Thus, certain compounds of formula (I) and (Ic) are useful intermediates in forming other compounds used in the present invention. For example $R'_2$ may be hydrogen and converted to $R_2$ alkyl group, for example methyl, by conventional amide alkylation procedures (Zabicky, *The chemistry of amides*; Interscience, London, 1970, p. 749). When X' is oxygen, it may be converted to X sulphur by standard thioamide formation reagents, such as $P_2S_5$ (*Chem. Rev.*, 61, 45, 1961 or *Angew. Chem.*, 78, 517, 1966) or the Lawesson reagent (*Tetrahedron*, 41, 5061, 1985). When Ar' or $R'_5$ is a methoxy substituted phenyl, it may be converted to another Ar' or $R'_5$ hydroxy substituted phenyl by standard demethylation procedures via Lewis acids, such as boron tribromide (*Synthesis*, 249, 1983) or mineral acids, such as hydrobromic or hydroiodic acid. When R is an alkoxycarbonyl group, for example methoxycarbonyl, it may be converted to another R, such as ethoxycarbonyl by transesterification with an appropriate alcohol at a temperature in a range from 20 to 120° C., carboxy by hydrolysis in acidic or basic medium, aminocarbonyl, alkylaminocarbonyl or dialkylaminocarbonyl by transamidation with ammonia, a primary amine or a secondary amine in methanol as solvent at a temperature in a range from 10 to 120° C., optionally in the presence of a catalytic amount of NaCN (*J. Org. Chem.*, 52, 2033, 1987) or by using trimethylaluminium ($Me_3Al$) (*Tetrahedron Letters*, 48, 4171, 1977), hydroxymethyl by a selective metal hydride reduction, such as lithium borohydride reduction (*Tetrahedron*, 35, 567, 1979) or sodium borohydride reduction in THF+MeOH (*Bull. Chem. Soc. Japan*, 57, 1948, 1984 or *Synth. Commun.*, 12, 463, 1982), alkylcarbonyl by acyl chloride formation and subsequent reaction with alkylmagnesium halides in THF as solvent at a temperature in a range from −78 to 30° C. (*Tetrahedron Letters*, 4303, 1979) or with alkylcadmium halides or dialkylcadmium in the presence of $MgCl_2$ or LiCl (*J. Org. Chem.*, 47, 2590, 1982). Another group which R' as methoxycarbonyl can be converted into is a substituted heteroaromatic ring, such as an oxadiazole (*J. Med. Chem.*, 34, 2726, 1991).

Scheme 2 summarizes some of the above described procedures to convert a compound of formula (Ic) or (I) in which X' is oxygen, R' is COOMe, Ar' and $R'_1$ to $R'_5$ are as described for formula (I) to another compound of formula (I).

Scheme 2

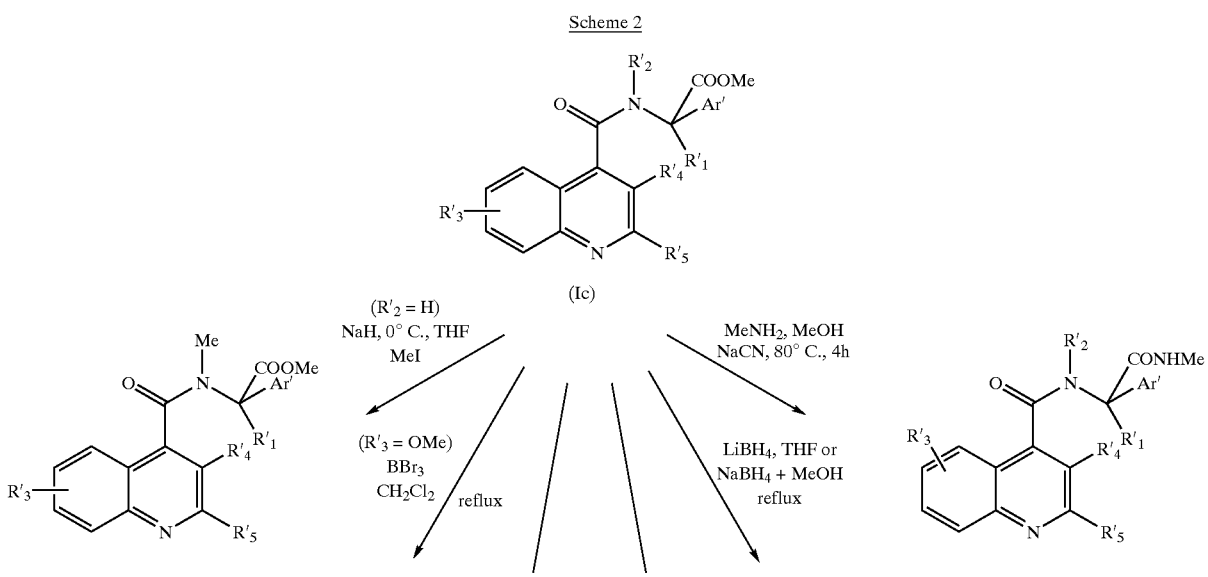

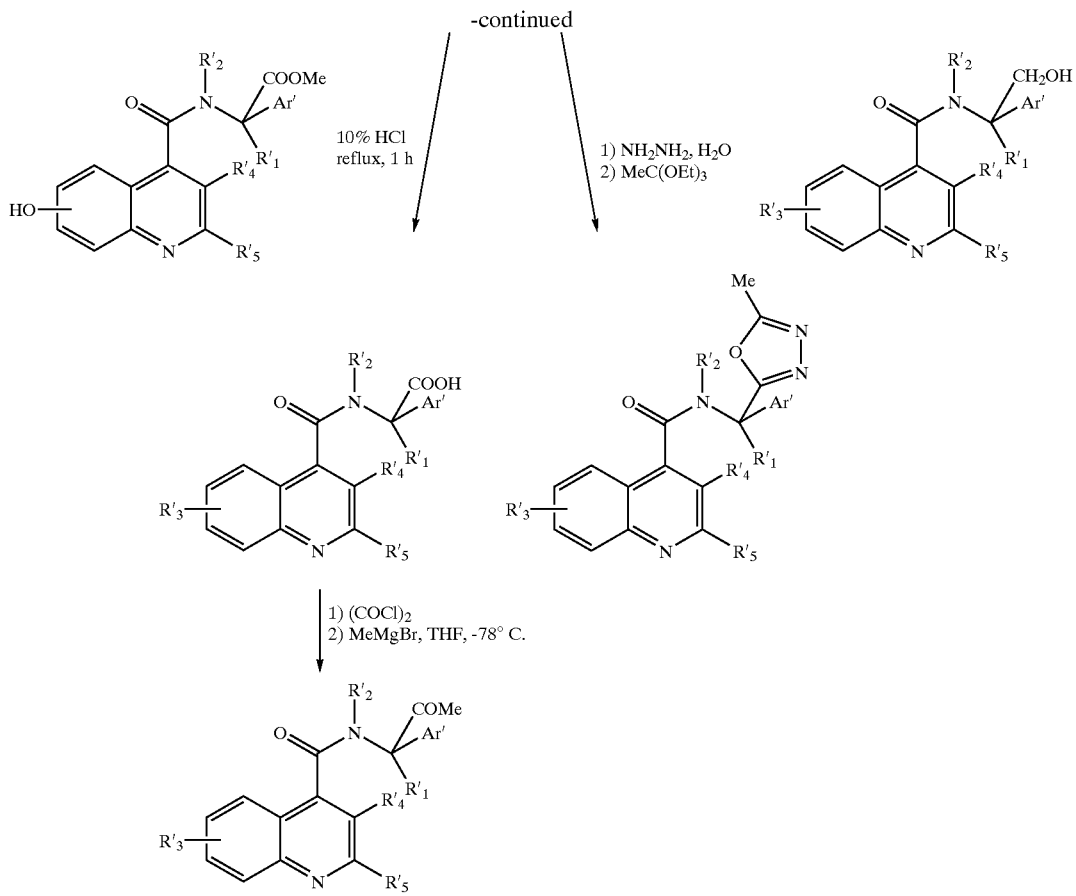

The compounds of formula (I) may be converted into their pharmaceutically acceptable acid addition salts by reaction with the appropriate organic or mineral acids.

Solvates of the compounds of formula (I) may be formed by crystallization or recrystallization from the appropriate solvent. For example, hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates.

As mentioned before, the compounds of formula (I) may exist in more than one stereoisomeric form and the above mentioned processes may produce racemates as well as enantiomerically pure forms. To obtain pure enantiomers, appropriate enantiomerically pure primary or secondary amines of formula (IIId) or (IIIe)

(IIId)

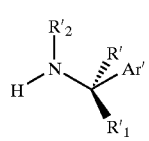

(IIIe)

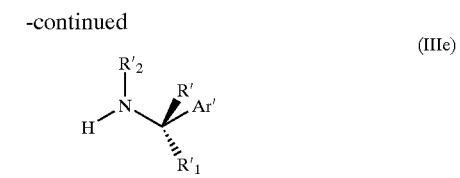

are reacted with compounds of formula (II), to obtain compounds of formula (I'd) or (I'e).

(I'd)

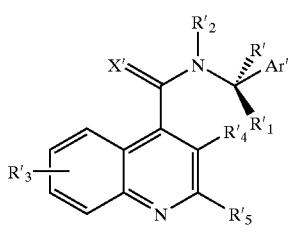

(I'e)

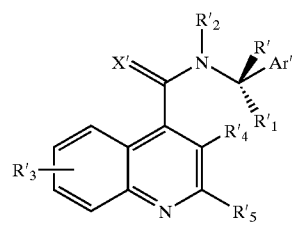

Compounds of formula (I'd) or(I'e) may subsequently be converted to compounds of formula (Id) or (Ie) by the methods of conversion mentioned before.

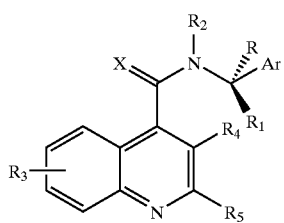

(Id)

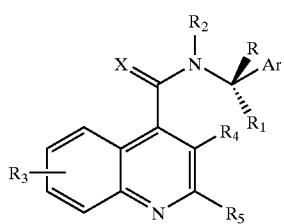

(Ie)

Compounds of formula (II) are known compounds or can be prepared from known compounds by known methods.

For example, the compound of formula (II), in which X' is oxygen, R'$_3$, R'$_4$ and R'$_5$ are hydrogen is described in Pfitzinger, *J. Prakt. Chem.*, 38, 582, 1882 and in Pfitzinger, *J. Prakt. Chem.*, 56, 293, 1897; the compound of formula (II), in which X' is oxygen, R'$_3$ and R'$_4$ are hydrogen and R'$_5$ is 2-pyridyl is described in Risaliti, *Ric. Scient.*, 28, 561, 1958; the compound of formula (II), in which X' is oxygen, R'$_3$ and R'$_4$ are hydrogen and R'$_5$ is o-, m- and p-chlorophenyl, o-fluorophenyl and 3,4-dichlorophenyl are described in Brown et al., *J. Am. Chem. Soc.*, 68, 2705, 1946; the compound of formula (II), in which X' is oxygen, R'$_3$ and R'$_4$ are hydrogen and R'$_5$ is p-methoxyphenyl is described in Ciusa and Luzzatto, *Gazz. Chim. Ital.*, 44, 64, 1914; the compound of formula (II), in which X' is oxygen, R'$_3$ and R'$_4$ are hydrogen and R'$_5$ is m-trifluoromethylphenyl is described in Shargier and Lalezari, *J. Chem. Eng. Data*, 8, 276, 1963; the compound of formula (II), in which X' is oxygen, R'$_3$ and R'$_4$ are hydrogen and R'$_5$ is p-fluorophenyl is described in Bu Hoi et al., *Rec Trav. Chim.*, 68, 781, 1949; the compound of formula (II), in which X' is oxygen, R'$_3$ and R'$_4$ are hydrogen and R'$_5$ is p-methylphenyl is described in Prevost et al., *Compt. Rend. Acad. Sci.*, 258, 954, 1964; the compound of formula (II), in which X' is oxygen, R'$_3$ and R'$_4$ are hydrogen and R'$_5$ is p-bromophenyl is described in Nicolai et al., *Eur. J. Med. Chem.*, 27, 977, 1992; the compound of formula (II) in which X' is oxygen, R'$_4$ and R'$_5$ are hydrogen and R'$_3$ is 6-methyl is described in Buchmann and Howton, *J. Am. Chem. Soc.*, 68, 2718, 1946; the compound of formula (II), in which X' is oxygen, R'$_4$ and R'$_5$ are hydrogen and R'$_3$ is 8-nitro is described in Buchmann et al, *J. Am. Chem. Soc.*, 69, 380, 1947; the compound of formula (II), in which X' is oxygen, R'$_4$ is hydrogen, R'$_3$ is 6-chloro, R'$_5$ is p-chlorophenyl is described in Lutz et al., *J. Am. Chem. Soc.*, 68, 1813, 1946; the compound of formula (II), in which X' is oxygen, R'$_4$ and R'$_5$ are hydrogen and R'$_5$ is 2-thiazolyl is described in Eur. Pat. Appl. EP 112,776; compounds of formula (II), in which X' is oxygen, R'$_3$ is 8-trifluoromethyl, R'$_4$ is hydrogen and R'$_5$ are phenyl, o- and p-fluorophenyl, 3,4-dichlorophenyl, p-methoxyphenyl are described in Nicolai et al., *Eur. J. Med. Chem.*, 27, 977, 1992; compounds of formula (II), in which X' is oxygen, R'$_3$ is 6-bromo, R'$_4$ is hydrogen and R'$_5$ are phenyl or p-fluorophenyl are described in Nicolai et al *Eur. J. Med. Chem.*, 27, 977, 1992; other compounds of formula (II) are described in Ger. Offen. DE 3,721,222 and in Eur. Pat. Appl. EP 384,313.

Compounds of formula (III), (IIId) and (IIIe) are commercially available compounds or can be prepared from known compounds by known methods (for example, compounds of formula (III) in which R' is alkoxycarbonyl, R'$_1$ and R'$_2$ are hydrogen and Ar' is as defined for the compounds of formula (I), are described in *Liebigs Ann. der Chemie*, 523, 199, 1936).

The activity of the compounds of formula (I) as NK$_3$ receptor antagonists in standard tests indicates that they are of potential therapeutic utility in the treatment of certain clinical conditions characterized by overstimulation of the thachykinin receptors, in particular the Conditions of the Invention disclosed above.

There is also provided in the present invention the use of a compound of formula (I), or a pharmaceutically acceptable salt thereof or a pharmaceutically acceptable solvate thereof, in the manufacture of a medicament for the treatment of certain conditions characterized by overstimulation of the thachykinin receptors, in particular the Conditions of the Invention disclosed above.

The present invention further provides a pharmaceutical composition comprising a compound of formula (I), or a pharmaceutically acceptable salt thereof or a or pharmaceutically acceptable solvate thereof, and a pharmaceutically acceptable carrier therefor, for use in the treatment of certain clinical conditions characterized by overstimulation of the thachykinin receptors, in particular the Conditions of the Invention disclosed above.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the conditions.

Preferably, a pharmaceutical composition of the invention is in unit dosage form and in a form adapted for use in the medical or veterinarial fields. For example, such preparations may be in a pack form accompanied by written or printed instructions for use as an agent in the treatment of the conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The active compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

The active compounds of this invention may also be administered by inhalation, via the nasal or oral routes. Such administration can be carried out with a spray formulation comprising a compound of the invention and a suitable carrier, optionally suspended in, for example, a hydrocarbon propellant.

Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the active compounds of this invention comprises transdermal delivery utilising a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

No unacceptable toxicological effects are expected with the compounds of formula (I), or a pharmaceutically acceptable salt thereof or a or pharmaceutically acceptable solvate thereof, when administered in accordance with the invention.

The activity of the compounds of the present invention, as $NK_3$ ligands, is determined by their ability to inhibit the binding of the radiolabelled $NK_3$ ligands, [$^{125}$I]-[Me-Phe$^7$]-NKB or [$^3$H]-Senktide, to guinea-pig and human $NK_3$ receptors (Renzertti et al, 1991, Neuropeptide, 18, 104–114; Buell et al, 1992, FEBS, 299(1), 90–95; Chung et al, 1994, Biochem. Biophys. Res. Commun., 198(3), 967–972). The binding assays utilized allow the determination of the concentration of the individual compound required to reduce by 50% the [$^{125}$I]-[Me-Phe$^7$]-NKB and [$^3$H]-Senktide specific binding to $NK_3$ receptor in equilibrium conditions (IC50). Binding assays provide for each compound tested a mean $IC_{50}$ value of 2–5 separate experiments performed in duplicate or triplicate. The most potent compounds of the present invention show $IC_{50}$ values in the range 1–1000 nM; in particular, in guinea-pig cortex membranes by displacement of [$^3$H]-Senktide, the compounds of the Examples 22, 47, 48, and 85 display $K_i$s (nM) of 5.6, 8.8, 12.0 and 4.8 respectively (n=3). The $NK_3$-antagonist activity of the compounds of the present invention is determined by their ability to inhibit senktide-induced contraction of the guinea-pig ileum (Maggi et al, 1990, Br. J. Pharmacol., 101, 996–1000) and rabbit isolated iris sphincter muscle (Hall et al., 1991, Eur. J. Pharmacol., 199, 9–14) and human $NK_3$ receptors-mediated $Ca^{++}$ mobilization (Mochizuki et al, 1994, J. Biol. Chem., 269, 9651–9658). Guinea-pig and rabbit in-vitro functional assays provide for each compound tested a mean $K_B$ value of 3–8 separate experiments, where $K_B$ is the concentration of the individual compound required to produce a 2-fold rightward shift in the concentration-response curve of senktide. Human receptor functional assay allows the determination of the concentration of the individual compound required to reduce by 50% ($IC_{50}$ values) the $Ca^{++}$ mobilization induced by the agonist NKB. In this assay, the compounds of the present invention behave as antagonists. The therapeutic potential of the compounds of the present invention in treating the conditions can be assessed using rodent disease models.

The following Descriptions illustrate the preparation of the intermediates, whereas the Examples illustrate the preparation of the compounds used in the present invention. The compounds of the Examples are summarised in the Tables 1 to 6.

DESCRIPTION 1

2-phenylquinoline4-carboxylic acid chloride 11.7 ml (136.3 mmol) of oxalyl chloride were dissolved in 150 ml of $CH_2Cl_2$. The solution was cooled at −10° C. and 20 g (80.2 mmol) of commercially available 2-phenylquinoline-4-carboxylic acid were added portionwise. The reaction mixture was left overnight at room temperature and then evaporated to dryness to yield 22 g of the title compound, used without further purification.

$C_{16}H_{10}ClNO$
M.W.=267.76

DESCRIPTION 2

7-methoxy-2-phenylquinoline-4-carboxylic acid 5 g (28.2 mmol) of 6-methoxyisatin, 4 ml (33.8 mmol) of acetophenone and 5.2 g (92.6 mmol) of potassium hydroxide were dissolved in 22.9 ml of abs. EtOH and the slurry heated at 80° C. for 42 hours. After cooling of the reaction mixture, 50 ml of water were added and the solution extracted with 50 ml of $Et_2O$. The ice-cooled aqueous phase was acidified to pH 1 with 37% HCl and the precipitate collected by filtration and washed with water.

The solid obtained was dried in-vacuo at 40° C. to yield 7.0 g of the title compound.

$C_{17}H_{13}NO_3$
M.P.=226–228° C.
M.W.=279.30

Elemental analysis: Calcd. C, 73.11; H, 4.69; N, 5.01; Found C, 72.07; H, 4.59; N, 4.90.

I.R. (KBr): 3420; 1630 $cm^{-1}$.

DESCRIPTION 3

7-methoxy-2-phenylquinoline-4-carboxylic acid chloride 2.8 ml (32.3 mmol) of oxalyl chloride were dissolved in 60 ml of $CH_2Cl_2$. The solution was cooled at −10° C. and 6 g (19.0 mmol) of 7-methoxy-2-phenylquinoline-4-carboxylic acid were added portionwise. The reaction mixture was left overnight at room temperature and then evaporated to dryness to yield 7 g of the title compound, used without further purification.

$C_{17}H_{12}ClNO_2$
M.W.=297.74

DESCRIPTION 4

7-hydroxy-2-phenylquinoline-4-carboxylic acid hydroiodide 1.5 g (5.4 mmol) of 7-methoxy-2-phenylquinoline-4-carboxylic acid were added portionwise to 50 ml of 57% aqueous HI. The reaction mixture was refluxed and vigourously stirred for 5 hours; then it was evaporated in-vacuo to dryness to yield 2.1 g of the title compound.

$C_{16}H_{11}NO_3 \cdot HI$
M.W.=393.17
I.R. (KBr): 3120; 1650; 1620 $cm^{-1}$.

DESCRIPTION 5

2-(2-thienyl)quinoline-4-carboxylic acid 5 g (34.0 mmol) of isatin, 4.4 ml (40.8 mmol) of 2-acetylthiophene and 6.3 g (112.2 mmol) of potassium hydroxide were dissolved in 40 ml of abs. EtOH and the slurry heated at 80° C. for 16 hours. After cooling of the reaction mixture, 50 ml of water were added and the solution extracted with 50 ml of $Et_2O$. The ice-cooled aqueous phase was acidified to pH 1 with 37% HCl and the precipitate collected by filtration and washed with water.

The crude product obtained was dried in-vacuo at 40° C. and triturated with EtOAc to yield 4.8 g of the title compound.

$C_{14}H_9NO_2S$
M.P.=181–183° C.
M.W.=255.29
I.R. (KBr): 1620 $cm^{-1}$.

300 MHz $^1H$-NMR (DMSO-$d_6$): δ 8.60 (d, 1H); 8.45 (s, 1H); 8.10 (m, 2H); 7.78 (m, 2H); 7.68 (t, 1H); 7.22 (m, 1H).

DESCRIPTION 6

2-(2-furyl)quinoline-4-carboxylic acid 5 g (34.0 mmol) of isatin, 4 ml (40.8 mmol) of 2-acetylfuran and 6.3 g (112.2 mmol) of potassium hydroxide were dissolved in 40.9 ml of abs. EtOH and the slurry heated at 80° C. for 12 hours. After cooling of the reaction mixture, 50 ml of water were added and the solution extracted with 50 ml of $Et_2O$. The ice-cooled aqueous phase was acidified to pH 1 with 37% HCl and the precipitate collected by filtration and washed with water. The crude product obtained was dried in-vacuo at 40° C. to yield 8.5 g of the title compound.

$C_{14}H_9NO_3$
M.W.=239.23

DESCRIPTION 7

2-(2-furyl)quinoline-4carboxylic acid chloride 5.2 ml (60.4 mmol) of oxalyl chloride were dissolved in 70 ml of $CH_2Cl_2$. The solution was cooled at −10° C. and 8.5 g (35.5 mmol) of 2-(2-furyl)quinoline-4-carboxylic acid were added portionwise. The reaction mixture was left overnight at room temperature and then evaporated to dryness to yield 9.2 g of the title compound, used without further purification.

$C_{14}H_8ClNO_2$
M.W.=257.78

DESCRIPTION 8

2-(4-pyridyl)quinoline4-carboxylic acid hydrochloride 5 g (34.0 mmol) of isatin, 4.5 ml (40.8 mmol) of 4-acetylpyridine and 6.3 g (112.2 mmol) of potassium hydroxide were dissolved in 40 ml of abs. EtOH and the slurry heated at 80° C. for 12 hours. After cooling of the reaction mixture, 50 ml of water were added and the solution extracted with 50 ml of $Et_2O$. The ice-cooled aqueous phase was acidified to pH 1 with 37% HCl and the precipitate collected by filtration and washed with water.

The aqueous solution was evaporated in-vacuo to dryness, the residue triturated with EtOH and filtered off. Evaporation of the solvent afforded 6.0 g of the crude title compound. This product was combined with the previously obtained precipitate and recrystallized from toluene containing traces of MeOH to yield 4.5 g of the title compound.

$C_{15}H_{10}N_2O_2\cdot HCl$
M.P.=297–301° C.
M.W.=286.72
I.R. (KBr): 1705; 1635; 1610 cm$^{-1}$.
300 MHz $^1$H-NMR (DMSO-d$_6$): δ 8.90 (d, 2H); 8.70 (m, 2H); 8.50 (s, 2H); 8.28 (d, 1H); 7.89 (dt, 2H).

DESCRIPTION 9

2-(4-pyridyl)quinoline4-carboxylic acid chloride hydrochloride 1.3 ml (10.4 mmol) of oxalyl chloride were dissolved in 60 ml of CH$_2$Cl$_2$. The solution was cooled at −10° C. and 3.0 g (14.4 mmol) of 2-(4-pyridyl)quinoline-4-carboxylic acid hydrochloride were added portionwise. The reaction mixture was left 72 hours at room temperature and then evaporated to dryness to yield 4.0 g of the title compound, used without further purification.
$C_{15}H_9ClN_2O\cdot HCl$
M.W.=305.22

EXAMPLE 1

(R,S)-N-(α-methylbenzyl)-2-phenylquinoline-4-carboxamide 1.2 ml (9.4 mmol) of (R,S) α-methylbenzylamine and 1.6 ml (11.7 mmol) of triethylamine (TEA) were dissolved, under nitrogen athmosphere, in 50 ml of a 1:1 mixture of dry CH$_2$Cl$_2$ and CH$_3$CN.

2.0 g (7.8 mmol) of 2-phenylquinoline-4-carbonylchloride, dissolved in 50 ml of a 1:4 mixture of dry CH$_2$Cl$_2$ and DMF, were added dropwise to the ice-cooled solution of the amines and the reaction was kept at 0°–5° C. for 1 hour and left at room temperature overnight.

The reaction mixture was evaporated in-vacuo to dryness, the residue was dissolved in EtOAc and washed twice with a sat. sol. of NaHCO$_3$. The organic layer was separated, dried over Na$_2$SO$_4$, filtered and evaporated in-vacuo to dryness. The residual oil was crystallized from EtOAc to yield 1.1 g of the title compound as a white solid.
$C_{24}H_{20}N_2O$
M.P.=156–157° C.
M.W.=352.43
Elemental analysis: Calcd. C, 81.79; H, 5.72; N, 7.95; Found C, 81.99; H, 5.69; N, 7.89.
I.R. (KBr): 3240;1645 cm$^{-1}$.
300 MHz $^1$H-NMR (DMSO-d$_6$): δ 9.29 (d, 1H); 8.32 (d, 2H); 8.13 (d, 1H); 8.13 (s, 1H); 8.06 (d, 1H); 7.81 (ddd, 1H); 7.68–7.52 (m, 4H); 7.47 (d, 2H); 7.39 (dd, 2H); 7.27 (dd, 1H); 5.30 (dq, 1H); 1.52 (d, 3H).
MS (EI; source 200° C.; 70 V; 200 mA): 352 (M+.); 337; 232; 204; 77.

EXAMPLE 2

S-(+)-N-(α-methylbenzyl)-2-phenylquinoline-4-carboxamide

Prepared as Ex. 1 from 1.2 ml (9.4 mmol) of S-(−)-(α-methylbenzylamine, 1.6 ml (11.7 mmol) of TEA, 2.0 g (7.8 mmol) of 2-phenylquinoline-4-carbonylchloride in 100 ml of a mixture of CH$_2$Cl$_2$, CH$_3$CN and DMF.

The work-up of the reaction mixture was carried out in the same manner as described in Ex. 1. The residual oil was crystallized from EtOAc to yield 1.1 g of the title compound.
$C_{24}H_{20}N_2O$
M.P.=161–162° C.
M.W.=352.43
$[\alpha]_D^{20}$=+25 (C=0.5, DMF)
I.R. (KBr): 3240; 1645 cm$^{-1}$.
300 MHz $^1$H-NMR (DMSO-d$_6$): δ 9.29 (d, 1H); 8.32 (d, 2H); 8.13 (d, 1H); 8.13 (s, 1H); 8.06 (d, 1H); 7.81 (ddd, 1H); 7.68–7.52 (m, 4H); 7.47 (d, 2H); 7.39 (dd, 2H); 7.27 (dd, 1H); 5.30 (dq, 1H); 1.52 (d, 3H).
MS spectra was identical to that of the Ex. 1.

EXAMPLE 3

R-(−)-N-(α-methylbenzyl)-2-phenylquinoline-4-carboxamide

Prepared as Ex. 1 from 1.2 ml (9.4 mmol) of R-(+)-α-methylbenzylamine, 1.6 ml (11.7 mmol) of TEA and 2.0 g (7.8 mmol) of 2-phenylquinoline-4-carbonylchloride in 100 ml of a mixture of CH$_2$Cl$_2$, CH$_3$CN and DMF. The work-up of the reaction mixture was carried out in the same manner as described in Ex. 1. The residual oil was crystallized from EtOAc to yield 1.1 g of the title compound.
$C_{24}H_{20}N_2O$
M.P.=158–160° C.
M.W.=352.43
$[\alpha]_D^{20}$=−25 (C=0.5, DMF)
I.R. (KBr): 3240; 1645 cm$^{-1}$.
The $^1$H-NMR and MS spectra were identical to those of the Ex. 1 and Ex. 2.

EXAMPLE 4

(R,S)-N-[α-(methoxycarbonyl)benzyl]-2-phenylquinoline-4-carboxamide 2.0 g (8.0 mmol) of 2-phenylquinoline-4-carboxylic acid were dissolved, under nitrogen athmosphere, in 130 ml of dry THF and 100 ml of CH$_3$CN.

2.0 g (9.9 mmol) of (D,L) methyl phenylglicinate hydrochloride and 1.5 ml (10.7 mmol) of TEA were added and the reaction mixture was cooled at 5° C.

2.5 g (12.1 mmol) of dicyclohexylcarbodiimide (DCC), dissolved in 10 ml of dry CH$_2$Cl$_2$, were added dropwise and the solution was allowed to reach room temperature, stirred for 5 hours and left overnight.

The precipitated dicyclohexylurea was filtered off and the solution was evaporated in-vacuo to dryness. The residue was dissolved in CH$_2$Cl$_2$ and then washed with H$_2$O. The organic layer was separated, dried over Na$_2$SO$_4$ and evaporated in-vacuo to dryness to obtain 6.0 g of a crude product which was dissolved in 20 ml of CH$_2$Cl$_2$ and left overnight. Some more dicyclohexylurea precipitated and was filtered off. The solution was evaporated in-vacuo to dryness and the residue flash chromatographed on 230–400 mesh silica gel, eluting with a mixture of hexane/ethyl acetate 3:2 containing 0.5% NH$_4$OH. The crude solid obtained was triturated with warm i-Pr$_2$O, filtered, washed and dried to yield 1.1 g of the title compound.
$C_{25}H_{20}N_2O_3$
M.P.=170–172° C.
M. W.=396.45
Elemental analysis: Calcd. C, 75.74; H, 5.09; N, 7.07; Found C, 75.88; H, 5.12; N, 7.06.
I.R. (nujol): 3240; 1750; 1670 cm$^{-1}$.

300 MHz $^1$H-NMR (DMSO-d$_6$): δ 9.72 (d, 1H); 8.28 (dd, 2H); 8.20 (dd, 1H); 8.13 (dd, 1H); 8.11 (s, 1H); 7.83 (ddd, 1H); 7.66 (ddd, 1H); 7.60–7.50 (m, 5H); 7.47–7.37 (m, 3H); 5.78 (d, 1H); 3.72 (s, 3H).

MS (EI; source 200° C.; 70 V; 200 mA): 396 (M+.); 337; 232; 204.

EXAMPLE 5

(+)-(S)-N-[α-(methoxycarbonyl)benzyl]-2-phenylquinoline-4-carboxamide 2.0 g (8.0 mmol) of 2-phenylquinoline-4-carboxylic acid were dissolved, under nitrogen athmosphere, in 70 ml of dry THF and 30 ml of CH$_3$CN.

1.7 g (8.4 mmol) of (L) methyl phenylglicinate hydrochloride, 1.1 ml (9.9 mmol) of N-methylmorpholine and 2.1 g (15.5 mmol) of N-hydroxybenzotriazole (HOBT) were added and the reaction mixture was cooled at 0° C.

1.85 g (9.0 mmol) of DCC, dissolved in 10 ml of CH$_2$Cl$_2$, were added dropwise and the solution was kept at 0°–5° C. for 1 hour and then at room temperature for 2 hours. The precipitated dicyclohexylurea was filtered off and the solution evaporated in-vacuo to dryness. The residue was dissolved in CH$_2$Cl$_2$ and washed with H$_2$O, sat. sol. NaHCO$_3$, 5% citric acid, sat. sol. NaHCO$_3$ and sat. sol. NaCl.

The organic layer was separated, dried over Na$_2$SO$_4$ and evaporated in-vacuo to dryness; the residue was dissolved in 20 ml of CH$_2$Cl$_2$ and left overnight. Some more dicyclohexylurea precipitated and was filtered off.

The solution was evaporated in-vacuo to dryness to obtain 2.6 g of a crude product which was triturated with petroleum ether, filtered washed with i-Pr$_2$O and then recrystallized from 70 ml of i-PrOH to yield 1.7 g of the title compound.

C$_{25}$H$_{20}$N$_2$O$_3$

M.P.=180–181° C.

M.W.=396.45

I.R. (nujol): 3300; 1750; 1640 cm$^{-1}$.

$[α]_D^{20}$=+42.0 (C=0.5, MeOH).

The $^1$H-NMR and MS spectra were identical to those of Ex. 4.

EXAMPLE 6

(−)-(R)-N-[α-(methoxycarbonyl)benzyl]-2-phenylquinoline-4-carboxamide

Prepared as Ex. 5 from 2.0 g (8.0 mmol) of 2-phenylquinoline-4-carboxylic acid, 1.7 g (8.4 mmol) of (D) methyl phenylglicinate hydrochloride, 1.1 ml (9.9 mmol) of N-methylmorpholine, 2.1 g (15.5 mmol) of HOBT and 1.85 g (9.0 mmol) of DCC in 70 ml of dry THF and 30 ml of CH$_3$CN.

The work-up of the reaction mixture was carried out in the same manner as described in Ex. 5. The crude product obtained (3.5 g) was triturated twice with warm i-Pr$_2$O, filtered, washed and then recrystallized from 80 ml of i-PrOH to yield 2.3 g of the title compound.

C$_{25}$H$_{20}$N$_2$O$_3$

M.P.=180–181° C.

M.W.=396.45

I.R. (nujol): 3300; 1750; 1640 cm$^{-1}$.

$[α]_D^{20}$=42.0 (C=0.5, MeOH).

The $^1$H-NMR and MS spectra were identical to those of Exs. 4 and 5.

EXAMPLE 7

(R,S)-N-[α-(methoxycarbonyl)benzyl]-7-methoxy-2-phenylquinoline-4-carboxamide 1.0 g (5.0 mmol) of (D,L) methyl phenylglicinate hydrochloride were dissolved, under nitrogen athmosphere, in 30 ml of dry DMF.

2.5 g (18.1 mmol) of anhydrous potassium carbonate were added and the solution cooled at 0° C.

0.7 g (2.3 mmol) of the compound of Description 3, dissolved in 25 ml of dry DMF, were added dropwise and the solution was kept at 0°–5° C. for 1 hour and at room temperature overnight.

The reaction mixture was evaporated in-vacuo to dryness and the residue was dissolved in EtOAc and washed twice with H$_2$O. The organic layer was separated, dried over Na$_2$SO$_4$, filtered and evaporated in-vacuo to dryness.

The residual oil was flash chromatographed on 230–400 mesh silica gel, eluting with a mixture of hexane/ethyl acetate 3:2 containing 0.5% NH$_4$OH to afford 0.1 g of the crude product which was triturated with i-Pr$_2$O to yield 0.08 g of the title compound.

C$_{26}$H$_{22}$N$_2$O$_4$

M.P.=187–190° C.

M.W.=426.48

I.R. (KBr): 3220; 1750; 1660; 1620 cm$^{-1}$.

300 MHz $^1$H-NMR (CDCl$_3$): δ 8.13–8.08 (m, 3H); 7.80 (s, 1H); 7.55–7.38 (m, 9H); 7.21 (dd, 1H); 7.02 (d broad, H); 5.88 (d, 1H); 3.97 (s, 3H); 3.80 (s, 3H).

MS (EI; source 200° C.; 70 V; 200 mA): 426 (M+.); 367; 262; 234; 191; 77.

EXAMPLE 8

(R,S)-N-[α-(methoxycarbonyl)benzyl]-7-hydroxy-2-phenylquinoline-4-carboxamide

Prepared as Ex. 5 from 2.1 g (5.3 mmol) of the compound of Description 4, 1.08 g (5.3 mmol) of (D,L) methyl phenylglicinate hydrochloride, 1.5 ml (10.7 mmol) of TEA, 1.7 g (12.5 mmol) of HOBT and 1.2 g (5.8 mmol) of DCC in 70 ml of dry THF and 30 ml of CH$_3$CN.

The work-up of the reaction mixture was carried out in the same manner as described in Ex. 5. The crude product obtained was triturated with i-Pr$_2$O and then recrystallized twice from i-PrOH to yield 0.06 g of the title compound.

C$_{25}$H$_{20}$N$_2$O$_4$

M.P.=256–257° C.

M.W.=412.45

I.R. (KBr): 3270; 1750; 1650; 1620 cm$^{-1}$.

300 MHz $^1$H-NMR (DMSO-d$_6$): δ 10.30 (s broad, 1H); 9.64 (d, 1H); 8.22 (d, 2H); 8.04 (d, 1H); 7.85 (s, 1H); 7.60–7.34 (m, 9H); 7.21 (dd, 1H); 5.74 (d, 1H); 3.71 (s, 3H).

MS (EI; source 200° C.; 70 V; 200 mA): 412 (M+.); 353; 248; 220; 77.

EXAMPLE 9

(R,S)-N-[α-(carboxy)benzyl]-7-methoxy-2-phenylquinoline-4-carboxamide hydrochloride 0.18 g (0.4 mmol) of the product of Ex. 7 were dissolved in 10 ml of 10% HCl and 5 ml of dioxane. The reaction mixture was refluxed and stirred for 3 hours, then evaporated in-vacuo to dryness.

The crude product was triturated with warm EtOAc (containing a few drops of EtOH) to yield 0.16 g of the title compound.

$C_{25}H_{20}N_2O_4 \cdot HCl$

M.P.=228–230° C.

M.W.=448.91

I.R. (KBr): 3180; 1735; 1655; 1630 cm$^{-1}$.

300 MHz $^1$H-NMR (DMSO-d$_6$): δ 9.6 (d, 1H); 8.26 (dd, 2H); 8.14 (d, 1H); 7.98 (s, 1H); 7.63–7.52 (m, 6H); 7.46–7.36 (m, 3H); 7.33 (dd, 1H); 5.66 (d, 1H); 3.98 (s, 3H).

MS (EI; source 200° C.; 70 V; 200 mA): 412 (M+.); 368; 262; 234; 191; 77.

EXAMPLE 10

(R,S)-N-[α-(methylaminocarbonyl)benzyl]-2-phenylquinoline-4-carboxamide 0.45 g (1.1 mmol) of the product of Ex. 4 were dissolved in 40 ml of 33% MeNH$_2$/EtOH; a catalitic amount of NaCN was added and the reaction mixture was heated at 70° C. for 1 hour in a parr apparatus. The internal pressure rised to 40 psi. The solution was evaporated in-vacuo to dryness and the residue was triturated with water, filtered, dried and recrystallized from a mixture of i-PrOH (50 ml) and EtOH (30 ml) to yield 0.2 g of the title compound.

$C_{25}H_{21}N_3O_2$

M.P.=261–263° C.

M.W.=395.47

Elemental analysis: Calcd. C, 75.93; H, 5.35; N, 10.63; Found C, 75.65; H, 5.34; N, 10.55.

I.R. (KBr): 3300; 3270; 1660; 1635 cm$^{-1}$.

300 MHz $^1$H-NMR (DMSO-d$_6$): δ 9.48 (d, 1H); 8.33–8.25 (m, 3H); 8.18–8.10 (m, 3H); 7.80 (ddd, 1H); 7.68–7.50 (m, 6H); 7.40–7.28 (m, 3H); 5.75 (d, 1H); 2.63 (d, 3H).

MS (EI; source 200° C.; 70 V; 200 mA): 395 (M+.); 337; 232; 204; 77.

EXAMPLE 11

(R,S)-N-[α-(methoxycarbonyl)benzyl]-2-(2-thienyl)quinoline-4-carboxamide

Prepared as Ex. 5 from 2.0 g (7.3 mmol) of 2-(2-thienyl)quinoline-4-carboxylic acid, 1.7 g (8.4 mmol) of (D,L) methyl phenylglicinate hydrochloride, 1.1 ml (10 mmol) of N-methylmorpholine, 2.1 g (15.5 mmol) of HOBT and 1.85 g (9.0 mmol) of DCC in 70 ml of dry THF, 30 ml of CH$_3$CN and 10 ml of CH$_2$Cl$_2$.

The work-up of the reaction mixture was carried out in the sane manner as described in Ex. 5. The crude product obtained was crystallized from EtOAc and then recrystallized from abs. EtOH to yield 0.9 g of the tide compound.

$C_{23}H_{18}N_2O_3S$

M.P.=178–180° C.

M.W.=402.47

Elemental analysis: Calcd. C, 68.64; H, 4.51; N, 6.96; Found C, 67.50; H, 4.99; N, 7.43.

I.R. (KBr): 3300; 1745; 1645 cm$^{-1}$.

300 MHz $^1$H-NMR (DMSO-d$_6$): δ 9.70 (d, 1H); 8.12 (d, 1H); 8.08 (s, 1H); 8.04 (d, 1H); 8.02 (d, 1H); 7.19 (t, 1H); 7.76 (d, 1H); 7.62 (t, 1H); 7.53 (d, 2H); 7.46–7.37 (m, 3H); 7.3 (dd, 1H); 5.68 (d, 1H); 3.68 (s, 3H).

MS (EI; source 200° C.; 70 V; 200 mA): 402 (M+.); 343; 238; 210; 77.

EXAMPLE 12

(R,S)-N-[α-(methoxycarbonyl)benzyl]-2-(2-furyl)quinoline-4-carboxamide

Prepared as Ex. 1 from 7.2 g (35.5 mmol) of (D,L) methyl phenylglicinate hydrochloride, 12.4 ml (88.8 mmol) of TEA and 9.1 g (35.5 mmol) of crude 2-(2-furyl)quinoline-4-carbonylchloride in 350 ml of a mixture of CH$_2$Cl$_2$, CH$_3$CN and DMF. The work-up of the reaction mixture was carried out in the same manner as described in Ex. 1. The crude product obtained was triturated with MeOH to yield 3.3 g of the title compound.

$C_{23}H_{18}N_2O_4$

M.P.=178–180° C.

M.W.=386.405

Elemental analysis: Calcd. C, 71.49; H, 4.70; N, 7.25; Found C, 71.67; H, 4.74; N, 7.17.

I.R. (KBr): 3300: 1750; 1650 cm$^{-1}$.

300 MHz $^1$H-NMR (DMSO-d$_6$): δ 9.72 (d, 1H); 8,12 (d, 1H); 8.06 (d, 1H); 7.96 (dd, 1H); 7.92 (s, 1H); 7.80 (ddd, 1H); 7.6 (ddd, 1H); 7.52 (dd, 2H); 7.45–7.35 (m, 4H); 6.73 (dd, 1H); 5.77 (d, 1H); 3.74 (s, 3H).

MS (EI; source 200° C.; 70 V; 200 mA): 386 (M+.); 327; 222; 194; 77.

EXAMPLE 13

(R,S)-N-[α-(methoxycarbonyl)benzyl]-2-(4-pyridyl)quinoline-4-carboxamide

Prepared as Ex. 1 from 3.4 g (16.7 mmol) of (D,L) methyl phenylglicinate hydrochloride, 3.9 ml (27.8 mmol) of TEA and 3.0 g (11.1 mmol) of 2-(4-pyridyl)quinoline-4-carbonylchloride in 100 ml of a mixture of CH$_2$Cl$_2$, CH$_3$CN and DMF. The work-up of the reaction mixture was carried out in the same manner as described in Ex. 1. The crude product obtained was recrystallized three times from EtOAc to yield 1.9 g of the title compound.

$C_{24}H_{19}N_3O_3$

M.P.=172–174° C.

M.W.=397.43

Elemental analysis: Calcd. C, 72.53; H, 4.82; N, 10.57; Found C, 71.87; H, 4.87; N, 10.44.

I.R. (KBr): 3240; 1750; 1670 cm$^{-1}$.

300 MHz $^1$H-NMR (DMSO-d$_6$): δ 9.74 (d, 1H); 8.79 (dd, 2H); 8.27–8.17 (m, 5H); 7.89 (ddd, 1H); 7.74 (ddd, 1H); 7.54 (dd, 2H); 7.47–7.38 (m, 3H); 5.8 (d, 1H); 3.75 (s, 3H).

MS (EI; source 200° C.; 70 V; 200 mA): 397 (M+.); 338; 233; 205; 77.

EXAMPLE 14

(R,S)-N-[α-(methoxycarbonyl)-2-thienylmethyl]-2-phenylquinoline-4-carboxamide

Prepared as Ex. 1 from 1.94 g (9.4 mmol) of (D,L) methyl thienylglicinate hydrochloride, 2.7 ml (19.5 mmol) of TEA and 2.0 g (7.8 mmol) of 2-phenylquinoline-4-carbonylchloride in 100 ml of a mixture of CH$_2$Cl$_2$, CH$_3$CN and DMF. The work-up of the reaction mixture was carried out in the same manner as described in Ex. 1. The crude product obtained was recrystallized three times from EtOAc to yield 0.66 g of the title compound.

$C_{23}H_{18}N_2O_3S$

M.P.=144–145° C.

M.W.=402.47

Elemental analysis: Calcd. C, 68.64; H, 4.51; N, 6.96; Found C, 68.81; H, 4.46; N, 6.96.

I.R. (KBr): 3295; 1745; 1640 cm$^{-1}$.

300 MHz $^1$H-NMR (CDCl$_3$): δ 8.25 (dd, 1H); 8.22 (dd, 1H); 8.17 (dd, 2H); 7.95 (s, 1H); 7.78 (ddd, 1H); 7.60 (ddd, 1H); 7.56–7.45 (m, 3H); 7.35 (dd, 1H) ; 7.20 (d, 1H); 7.05 (dd, 1H); 7.05 (s broad, 1H); 6.22 (d, 1H); 3.9 (s, 3H).

MS (EI; source 200° C.; 70 V; 200 mA): 402 (M+.); 343; 232; 204.

EXAMPLE 15

(R,S)-N-[α-(methoxycarbonylmethyl)benzyl]-2-phenylquinoline-4-carboxamide

Prepared as Ex. 5 from 1.39 g (5.60 mmol) of 2-phenylquinoline-4-carboxylic acid, 1.2 g (5.60 mmol) of (R,S) methyl 3-amino-3-phenylpropionate hydrochloride, 0.78 ml (5.60 mmol ) of TEA, 1.51 g (11.2 mmol) of HOBT and 2.31 g (11.2 mmol) of DCC in 10 ml of dry THF, 4 ml of CH$_3$CN and 7 ml of CH$_2$Cl$_2$. The work-up of the reaction mixture was carried out in the same manner as described in Ex. 5. The crude product obtained was dissolved in CH$_2$Cl$_2$ and left at 0° C. overnight. Some more dicyclohexylurea precipitated and was filtered off.

The solution was evaporated in-vacuo to dryness to obtain 1.4 g of a crude product which was triturated with a mixture of i-Pr$_2$O/acetone 99:1 to yield 1.2 g of the title compound as a white solid.

C$_{26}$H$_{22}$N$_2$O$_3$

M.P.=156–158° C.

M.W.=410.47

Elemental analysis: Calcd. C, 76.07; H, 5.40; N, 6.82; Found C, 75.77; H, 5.38; N, 6.94.

I.R. (KBr): 3295; 1755; 1645; 1590; 1530 cm$^{-1}$.

300 MHz $^1$H-NMR (DMSO-d$_6$): δ 9.40 (d, 1H); 8.29 (dd, 2H); 8.14 (d, 1H); 8.07 (d, 1H); 8.04 (s, 1H); 7.83 (ddd, 1H); 7.66–7.52 (m, 4H); 7.50 (d, 2H); 7.40 (dd, 2H); 7.31 (ddd, 1H); 5.60 (dt, 1H); 3.65 (s, 3H); 3.04–2.89 (m, 2H).

MS (EI; source 200° C.; 70 V; 200 mA): 410 (M+.); 337; 233; 205.

TABLE 1

| Ex. | Ar | R | R$_1$ | R$_2$ | R$_3$ | R$_4$ | R$_5$ | * | Molecular formula | Melting point °C. | [α]$_D^{20}$ c = 0.5, MeOH |
|---|---|---|---|---|---|---|---|---|---|---|---|
| 1 | Ph | Me | H | H | H | H | Ph | (R,S) | C$_{24}$H$_{20}$N$_2$O | 156–157 | |
| 2 | Ph | Me | H | H | H | H | Ph | (S) | C$_{24}$H$_{20}$N$_2$O | 161–162 | +25°$^a$ |
| 3 | Ph | Me | H | H | H | H | Ph | (R) | C$_{24}$H$_{20}$N$_2$O | 158–160 | −25°$^a$ |
| 4 | Ph | COOMe | H | H | H | H | Ph | (R,S) | C$_{25}$H$_{20}$N$_2$O$_3$ | 170–172 | |
| 5 | Ph | COOMe | H | H | H | H | Ph | (S) | C$_{24}$H$_{20}$N$_2$O$_3$ | 180–181 | +42° |
| 6 | Ph | COOMe | H | H | H | H | Ph | (R) | C$_{24}$H$_{20}$N$_2$O$_3$ | 180–181 | −42° |
| 7 | Ph | COOMe | H | H | 7-OMe | H | Ph | (R,S) | C$_{26}$H$_{22}$N$_2$O$_4$ | 187–190 | |
| 8 | Ph | COOMe | H | H | 7-OH | H | Ph | (R,S) | C$_{25}$H$_{20}$N$_2$O$_4$ | 256–257 | |
| 9 | Ph | COOH | H | H | 7-OMe | H | Ph | (R,S) | C$_{25}$H$_{20}$N$_2$O$_4$.HCl | 228–230 | |
| 10 | Ph | CONHMe | H | H | H | H | Ph | (R,S) | C$_{25}$H$_{21}$N$_3$O$_2$ | 261–263 | |
| 11 | Ph | COOMe | H | H | H | H | 2-thienyl | (R,S) | C$_{23}$H$_{18}$N$_2$O$_3$S | 178–180 | |
| 12 | Ph | COOMe | H | H | H | H | 2-furyl | (R,S) | C$_{23}$H$_{18}$N$_2$O$_4$ | 178–180 | |
| 13 | Ph | COOMe | H | H | H | H | 4-Py | (R,S) | C$_{24}$H$_{19}$N$_3$O$_3$ | 172–174 | |
| 14 | 2-thienyl | COOMe | H | H | H | H | Ph | (R,S) | C$_{23}$H$_{18}$N$_2$O$_3$S | 144–145 | |
| 15 | Ph | CH$_2$COOMe | H | H | H | H | Ph | (R,S) | C$_{26}$H$_{22}$N$_2$O$_3$ | 156–158 | |

| Ex. | Acyl chloride of (II) | (III) | (I) |
|---|---|---|---|
| 18 | | | |

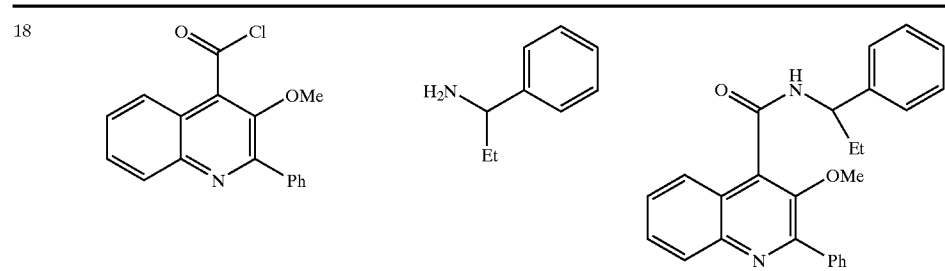

TABLE 1-continued

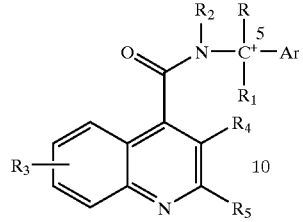

| Ex. | Stereo chemistry | Molecular formula | M.W. | yield (%) | m.p. (° C.) (recryst. solv.) | $[\alpha]_D^{20}$ (c = 1, MeOH) |
|---|---|---|---|---|---|---|
| 18 | (R,S) | $C_{26}H_{24}N_2O_2$ | 396.49 | 48 | 164–165 (iPrOH/iPr$_2$O) | |
| 19 | (R,S) | $C_{29}H_{30}N_2O$ | 422.58 | 30 | 147–150 (hexane) | |
| 20 | (R,S) | $C_{28}H_{24}N_2O_3$ | 436.52 | 43 | 186–188 (iPrOH/iPr$_2$O) | |
| 21 | (R,S) | $C_{31}H_{34}N_2O$ | 450.63 | 24 | 131–134 (hexane/iPr$_2$O) | |

[a]The solvent DMF

The compounds of the Examples 16–49 of general formula (I) (grouped in the following Table 2) were synthesized starting from the appropriate acyl chlorides of (II) and amines of formula (III) shown in the table and following the synthetic procedure described in Example 1. Acyl chlorides were synthesized starting from the corresponding acid of formula (II) and following Description 1. Reaction yields are calculated on the purified, but unrecrystallized material. Analytical and spectroscopic data of the compounds of the Examples 16–49 are grouped in Table 5.

TABLE 2
Acyl chloride of (II) + (III) → (I)
| Ex. | Acyl chloride of (II) | (III) | (I) | Stereo chemistry |
|---|---|---|---|---|
| 16 |  | 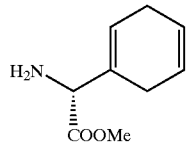 | 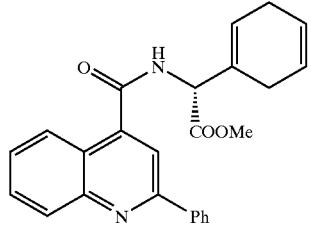 | (R) |
| 17 | 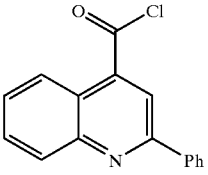 | 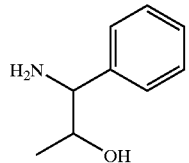 | 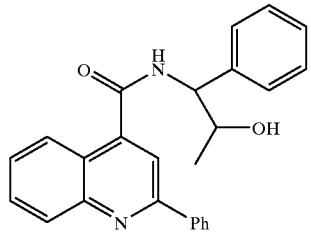 | (R,S) single diast. |
| 22 | 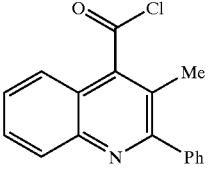 | 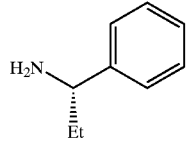 | 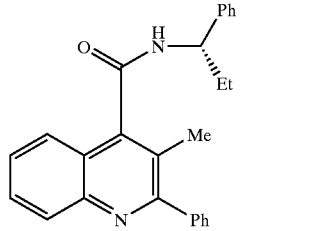 | (S) |
| 23 | 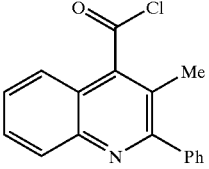 | 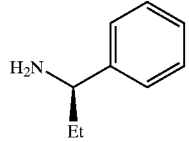 | 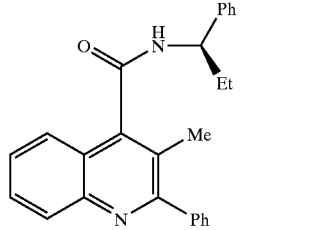 | (R) |
| 24 | 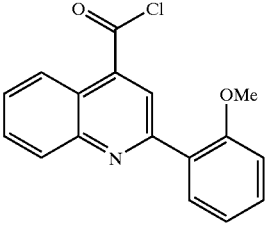 |  | 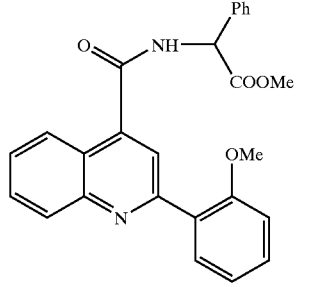 | (R,S) |
| 25 | 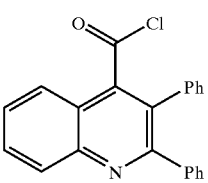 | 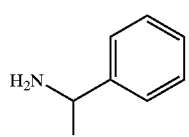 | 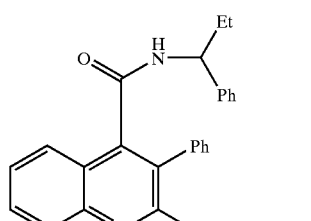 | (R,S) |

TABLE 2-continued
Acyl chloride of (II) + (III) → (I)
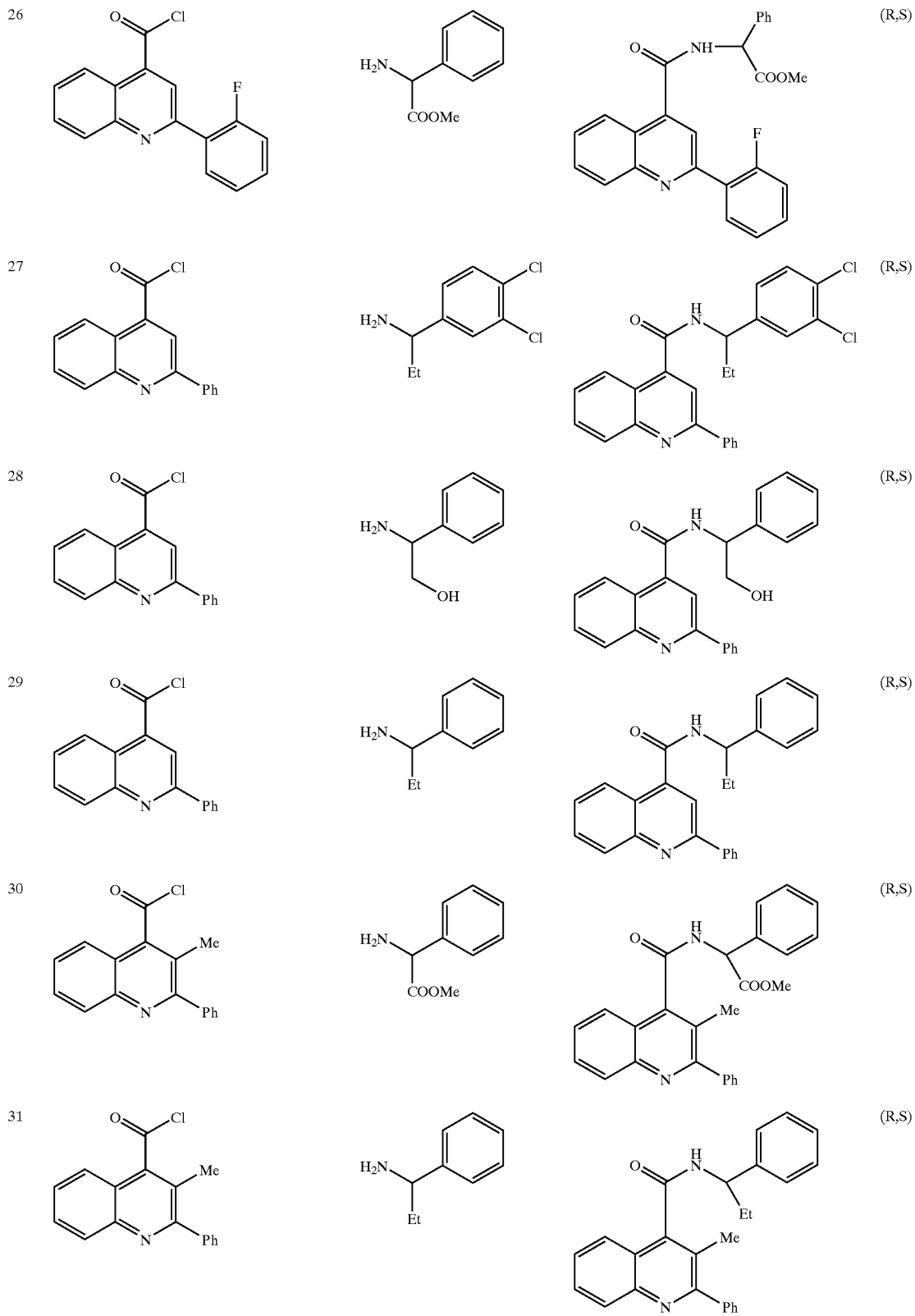

TABLE 2-continued
Acyl chloride of (II) + (III) → (I)
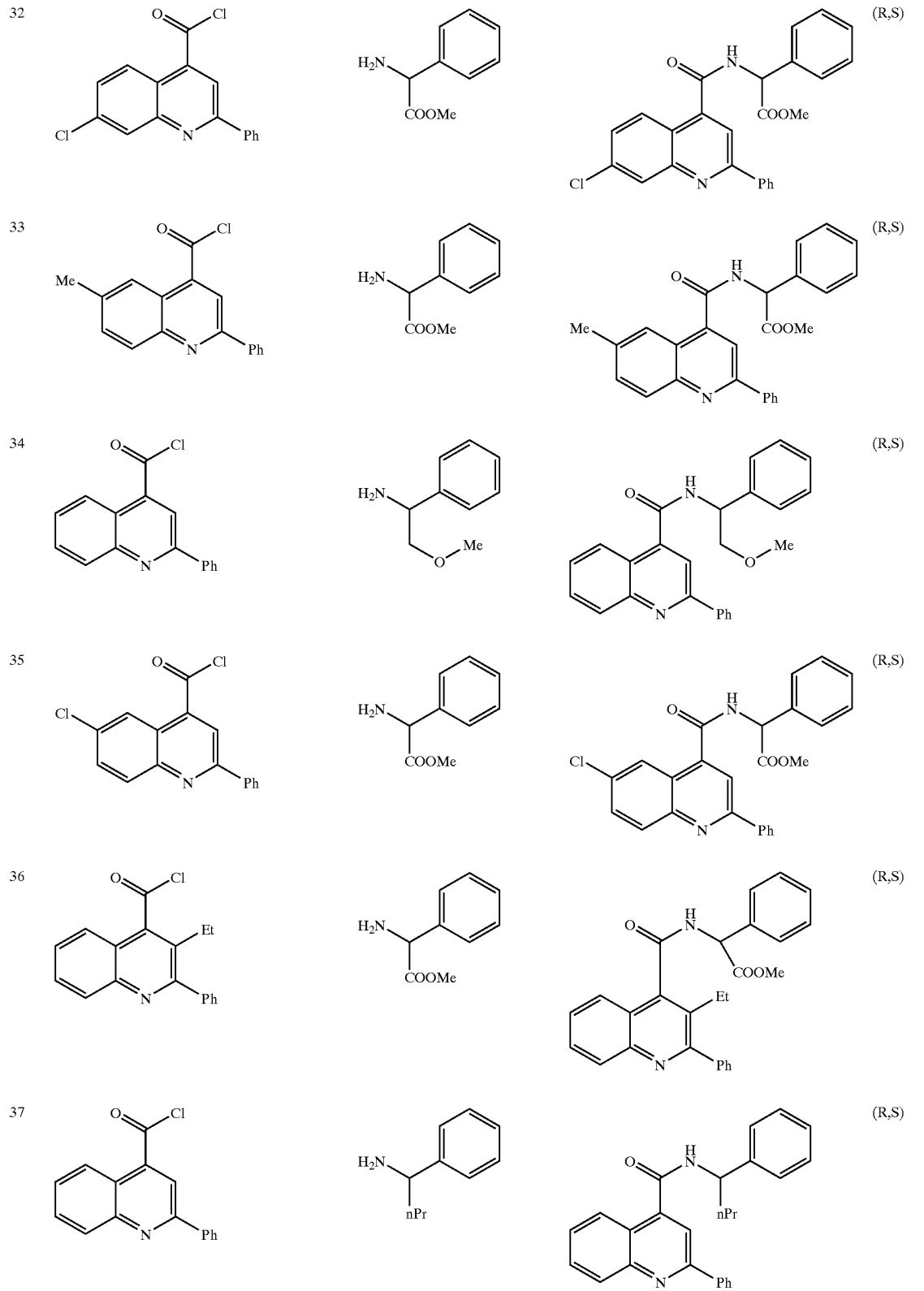

TABLE 2-continued

Acyl chloride of (II) + (III) → (I)

| | Acyl chloride (II) | Amine (III) | Product (I) | |
|---|---|---|---|---|
| 38 | 3-Et, 2-Ph quinoline-4-carbonyl chloride | 1-phenylpropylamine | corresponding amide | (R,S) |
| 39 | 3-phthalimido, 2-Ph quinoline-4-carbonyl chloride | 1-phenylpropylamine | corresponding amide | (R,S) |
| 40 | 3-nPr, 2-Ph quinoline-4-carbonyl chloride | 1-phenylpropylamine | corresponding amide | (R,S) |
| 41 | 6-Br, 3-Me, 2-(4-bromophenyl) quinoline-4-carbonyl chloride | (S)-1-phenylpropylamine | corresponding amide | (S) |
| 42 | 6-Br, 3-Me, 2-Ph quinoline-4-carbonyl chloride | (S)-1-phenylpropylamine | corresponding amide | (S) |
| 43 | 6-MeO, 2-Ph quinoline-4-carbonyl chloride | methyl phenylglycinate | corresponding amide | (R,S) |

TABLE 2-continued

Acyl chloride of (II) + (III) → (I)

| # | Acyl chloride | Amine | Product | Config. |
|---|---|---|---|---|
| 44 | 2-(benzofuran-2-yl)quinoline-4-carbonyl chloride | H₂N-CH(Ph)-COOMe | corresponding amide | (R,S) |
| 45 | 2-phenylquinoline-4-carbonyl chloride | H₂N-CH(Ph)-CH₂Ph | corresponding amide | (R,S) |
| 46 | 2-phenylquinoline-4-carbonyl chloride | H₂N-CH(Ph)-CF₃ | corresponding amide | (R,S) |
| 47 | 3-methoxy-2-phenylquinoline-4-carbonyl chloride | H₂N-CH(Ph)-Et | corresponding amide | (S) |
| 48 | 3-ethyl-2-phenylquinoline-4-carbonyl chloride | H₂N-CH(Ph)-Et | corresponding amide | (S) |
| 49 | 2-phenylquinoline-4-carbonyl chloride | H₂N-CH(4-ClC₆H₄)-Et | corresponding amide | (R,S) |

TABLE 2-continued

Acyl chloride of (II) + (III) → (I)

| Ex. | Molecular formula | M.W. | yield (%) | m.p. (° C.) (recryst. solv.) | $[\alpha]_D^{20}$ (c = 1, MeOH) |
|---|---|---|---|---|---|
| 16 | $C_{25}H_{22}N_2O_3$ | 398.47 | 16 | 120–122 (iPr$_2$O) | −18.9 (c = 0.5) |
| 17 | $C_{25}H_{22}N_2O_2$ | 382.47 | 44 | 204–205 (iPrOH/iPr$_2$O) | |
| 22 | $C_{26}H_{24}N_2O$ | 380.49 | 58 | 153–155 (iPr$_2$O) | −36.0 |
| 23 | $C_{26}H_{24}N_2O$ | 380.49 | 78 | 155–156 (iPr$_2$O) | +35.9 |
| 24 | $C_{26}H_{22}N_2O_4$ | 426.48 | 55 | 124–125 (toluene) | |
| 25 | $C_{31}H_{26}N_2O$ | 442.57 | 49 | 198–200 (toluene) | |
| 26 | $C_{25}H_{19}FN_2O_3$ | 414.44 | 75 | 146–147 (toluene) | |
| 27 | $C_{25}H_{20}Cl_2N_2O$ | 435.36 | 44 | 193–194 (toluene) | |
| 28 | $C_{24}H_{20}N_2O_2$ | 368.43 | 24 | 117–119 (toluene) | |
| 29 | $C_{25}H_{22}N_2O$ | 366.47 | 80 | 141–143 (toluene) | |
| 30 | $C_{26}H_{22}N_2O_3$ | 410.48 | 60 | 180–181 (toluene/iPr$_2$O) | |
| 31 | $C_{26}H_{24}N_2O$ | 380.49 | 55 | 156–158 (toluene/hexane) | |
| 32 | $C_{25}H_{19}ClN_2O_3$ | 430.90 | 48 | 180–183 (toluene) | |
| 33 | $C_{26}H_{22}N_2O_3$ | 410.48 | 48 | 179–181 (toluene) | |
| 34 | $C_{25}H_{22}N_2O_2$ | 382.47 | 42 | 144–145 (toluene) | |
| 35 | $C_{25}H_{19}ClN_2O_3$ | 430.90 | 46 | 197–199 (toluene) | |
| 36 | $C_{27}H_{24}N_2O_3$ | 424.50 | 52 | 156–157 (toluene/hexane) | |
| 37 | $C_{26}H_{24}N_2O$ | 380.49 | 50 | 149–150 (toluene) | |
| 38 | $C_{27}H_{26}N_2O$ | 394.52 | 53 | 158–159 (Et$_2$O/iPr$_2$O) | |
| 39 | $C_{33}H_{25}N_3O_3$ | 511.58 | 16 | 201–202 (toluene) | |
| 40 | $C_{28}H_{28}N_2O$ | 408.55 | 71 | 149–151 (toluene/hexane) | |
| 41 | $C_{26}H_{22}Br_2N_2O$ | 538.30 | 24 | 230–231 (Et$_2$O/iPr$_2$O) | −49.8 (c = 0.2) |
| 42 | $C_{26}H_{23}BrN_2O$ | 459.40 | 39 | 179–180 (hexane/iPrOH) | −60.5 |
| 43 | $C_{26}H_{22}N_2O_4$ | 426.48 | 45 | 209–211 (Me$_2$CO) | |
| 44 | $C_{27}H_{20}N_2O_4$ | 436.47 | 65 | 240–241 (EtOAc) | |
| 45 | $C_{30}H_{24}N_2O$ | 428.53 | 47 | 194–196 (EtOAc) | |
| 46 | $C_{24}H_{17}F_3N_2O$ | 406.41 | 45 | 180–181 (toluene) | |
| 47 | $C_{26}H_{24}N_2O_2$ | 396.49 | 58 | 132–134 (Me$_2$CO) | −45 (c = 0.5) |
| 48 | $C_{27}H_{26}N_2O$ | 394.52 | 53 | 118–120 (hexane) | −42 (c = 0.5) |
| 49 | $C_{25}H_{21}ClN_2O$ | 400.91 | 40 | 177–178 (toluene) | |

The compounds of the Examples 50–88 of general formula (I) (grouped in the following Table 3) were synthesized starting from the appropriate reagents (II) and (III) shown in the table and following the synthetic procedure described in Example 5. Reaction yields are calculated on the purified, but unrecrystallized material. Analytical and spectroscopic data of the compounds of the Examples 50–88 are grouped in Table 5.

TABLE 3

(II) + (III) → (I)

| Ex. | (II) | (III) | (I) | Stereo chemistry |
|---|---|---|---|---|
| 50 | 2-Ph-quinoline-4-COOH | MeNH-CH(Ph)-COOMe | N-Me, N-[CH(Ph)COOMe] 2-phenylquinoline-4-carboxamide | (R,S) |
| 51 | 2-(3-thienyl)-quinoline-4-COOH | H$_2$N-CH(Ph)-COOMe | N-[CH(Ph)COOMe] 2-(3-thienyl)quinoline-4-carboxamide | (R,S) |

TABLE 3-continued
(II) + (III) → (I)
| 52 | 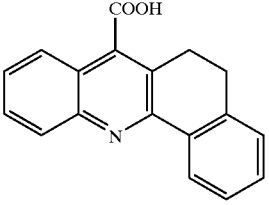 | 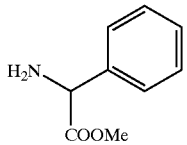 | 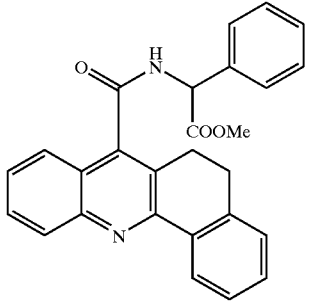 | (R,S) |
| 53 | 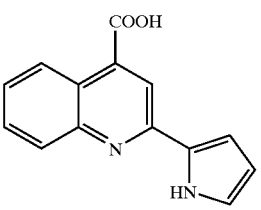 | 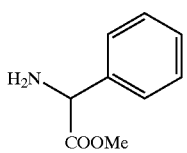 | 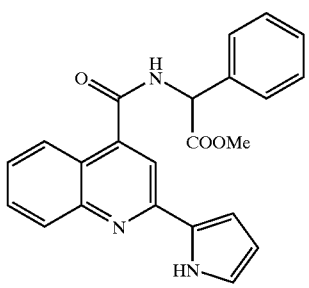 | (R,S) |
| 54 | 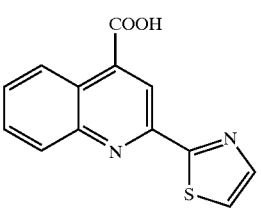 | 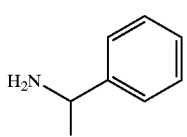 | 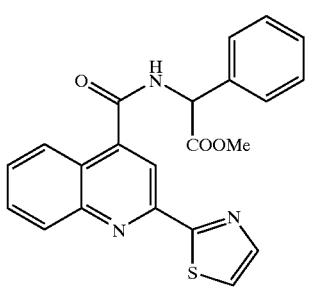 | (R,S) |
| 55 | 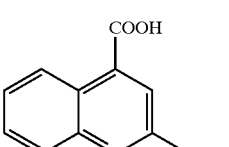 | 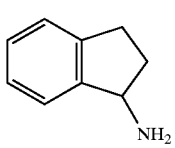 | 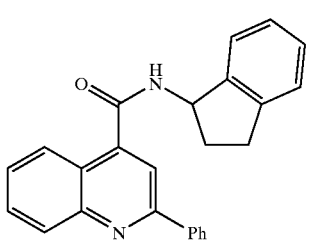 | (R,S) |
| 56 | 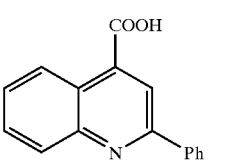 | 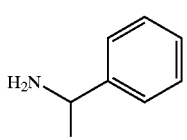 | 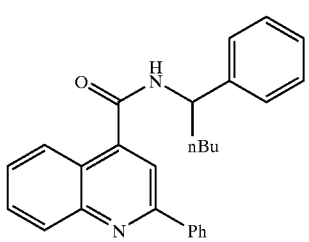 | (R,S) |

TABLE 3-continued (II) + (III) → (I)

| | | | | |
|---|---|---|---|---|
| 57 | 2-(4-methylphenyl)quinoline-4-carboxylic acid | methyl 2-amino-2-phenylacetate | methyl 2-({[2-(4-methylphenyl)quinolin-4-yl]carbonyl}amino)-2-phenylacetate | (R,S) |
| 58 | 2-phenylquinoline-4-carboxylic acid | 1-phenyloctan-1-amine | N-(1-phenyloctyl)-2-phenylquinoline-4-carboxamide | (R,S) |
| 59 | 2-(2-methylphenyl)quinoline-4-carboxylic acid | methyl 2-amino-2-phenylacetate | methyl 2-({[2-(2-methylphenyl)quinolin-4-yl]carbonyl}amino)-2-phenylacetate | (R,S) |
| 60 | 2-(4-methoxyphenyl)quinoline-4-carboxylic acid | methyl 2-amino-2-phenylacetate | methyl 2-({[2-(4-methoxyphenyl)quinolin-4-yl]carbonyl}amino)-2-phenylacetate | (R,S) |
| 61 | 2-phenylquinoline-4-carboxylic acid | 1-phenylcyclopentan-1-amine | N-(1-phenylcyclopentyl)-2-phenylquinoline-4-carboxamide | — |

TABLE 3-continued (II) + (III) → (I)

| | (II) | (III) | (I) | |
|---|---|---|---|---|
| 62 | 2-(4-hydroxyphenyl)quinoline-4-carboxylic acid | methyl 2-amino-2-phenylacetate | N-(methoxycarbonyl(phenyl)methyl)-2-(4-hydroxyphenyl)quinoline-4-carboxamide | (R,S) |
| 63 | 2-(benzo[d][1,3]dioxol-5-yl)quinoline-4-carboxylic acid | methyl 2-amino-2-phenylacetate | N-(methoxycarbonyl(phenyl)methyl)-2-(benzo[d][1,3]dioxol-5-yl)quinoline-4-carboxamide | (R,S) |
| 64 | 2-phenylquinoline-4-carboxylic acid | 2-phenylpropan-2-amine | N-(2-phenylpropan-2-yl)-2-phenylquinoline-4-carboxamide | — |
| 65 | 2-phenylquinoline-4-carboxylic acid | 1-(4-methylphenyl)propan-1-amine | N-(1-(4-methylphenyl)propyl)-2-phenylquinoline-4-carboxamide | (R,S) |
| 66 | 2-(1H-pyrrol-3-yl)quinoline-4-carboxylic acid | methyl 2-amino-2-phenylacetate | N-(methoxycarbonyl(phenyl)methyl)-2-(1H-pyrrol-3-yl)quinoline-4-carboxamide | (R,S) |

TABLE 3-continued (II) + (III) → (I)

| | | | | |
|---|---|---|---|---|
| 67 | 2-(3,4-dichlorophenyl)quinoline-4-carboxylic acid | methyl phenylglycinate | corresponding amide | (R,S) |
| 68 | 2-phenylquinoline-4-carboxylic acid | 2-amino-1-phenyl-ethyl phthalimide (a) | corresponding amide with CH₂NH₂ | (R) |
| 69 | 3-amino-2-phenylquinoline-4-carboxylic acid | (S)-1-phenylpropylamine | corresponding amide | (S) |
| 70 | 3-chloro-2-phenylquinoline-4-carboxylic acid | (S)-1-phenylpropylamine | corresponding amide | (S) |
| 71 | 3-bromo-2-phenylquinoline-4-carboxylic acid | (S)-1-phenylpropylamine | corresponding amide | (S) |
| 72 | 2-phenylquinoline-4-carboxylic acid | 2-methyl-1-phenylpropylamine | corresponding amide | (R,S) |

TABLE 3-continued (II) + (III) → (I)

| 73 | quinoline-4-COOH, 2-Ph | (S)-1-phenylpropylamine (NH2, Et) | N-[(S)-1-phenylpropyl] 2-phenylquinoline-4-carboxamide | (S) |
| 74 | quinoline-4-COOH, 2-Ph | (R)-1-phenylpropylamine (NH2, Et) | N-[(R)-1-phenylpropyl] 2-phenylquinoline-4-carboxamide | (R) |
| 75 | 6-fluoro-2-phenylquinoline-4-COOH | H2N-CH(Ph)-COOMe | methyl 2-[(6-fluoro-2-phenylquinoline-4-carbonyl)amino]-2-phenylacetate | (R,S) |
| 76 | 2-cyclohexylquinoline-4-COOH | H2N-CH(Ph)-COOMe | methyl 2-[(2-cyclohexylquinoline-4-carbonyl)amino]-2-phenylacetate | (R,S) |
| 77 | 2-(3-chlorophenyl)quinoline-4-COOH | H2N-CH(Ph)-COOMe | methyl 2-{[2-(3-chlorophenyl)quinoline-4-carbonyl]amino}-2-phenylacetate | (R,S) |
| 78 | 2-(2-chlorophenyl)quinoline-4-COOH | H2N-CH(Ph)-COOMe | methyl 2-{[2-(2-chlorophenyl)quinoline-4-carbonyl]amino}-2-phenylacetate | (R,S) |

TABLE 3-continued (II) + (III) → (I)

| # | (II) | (III) | (I) | |
|---|---|---|---|---|
| 79 | 3-hydroxy-2-phenylquinoline-4-carboxylic acid | H2N-CH(Et)-Ph | 3-hydroxy-2-phenyl-quinoline-4-carboxamide, N-(1-phenylpropyl) | (R,S) |
| 80 | 8-methoxy-2-phenylquinoline-4-carboxylic acid | H2N-CH(COOMe)-Ph | 8-methoxy-2-phenyl-quinoline-4-carboxamide, N-(methoxycarbonyl-phenylmethyl) | (R,S) |
| 81 | 8-hydroxy-2-phenylquinoline-4-carboxylic acid | H2N-CH(COOMe)-Ph | 8-hydroxy-2-phenyl-quinoline-4-carboxamide, N-(methoxycarbonyl-phenylmethyl) | (R,S) |
| 82 | 2-(2,4-dichlorophenyl)quinoline-4-carboxylic acid | H2N-CH(COOMe)-Ph | 2-(2,4-dichlorophenyl)-quinoline-4-carboxamide, N-(methoxycarbonyl-phenylmethyl) | (R,S) |
| 83 | 2-phenylquinoline-4-carboxylic acid | H2N-CH(COOMe)-(4-OH-C6H4) | 2-phenyl-quinoline-4-carboxamide, N-[(4-hydroxyphenyl)(methoxycarbonyl)methyl]·HCl | (R) |
| 84 | 2-phenylquinoline-4-carboxylic acid | H2N-CH(Ph)2 | 2-phenyl-quinoline-4-carboxamide, N-(diphenylmethyl) | — |

TABLE 3-continued (II) + (III) → (I)

| 85 | 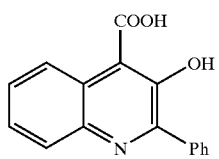 | 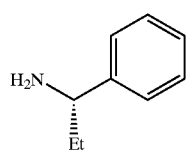 | 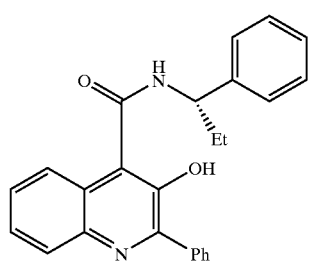 | (S) |
| 86 | 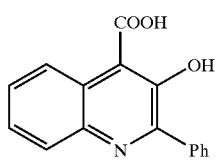 | 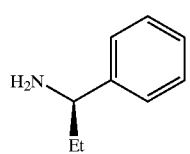 | 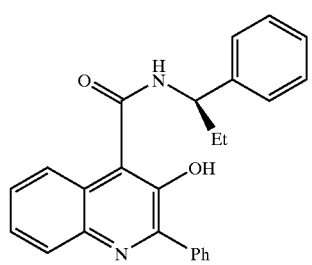 | (R) |
| 87 | 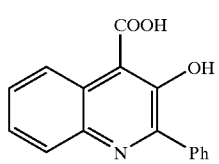 | 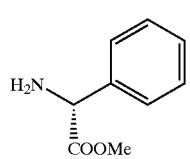 | 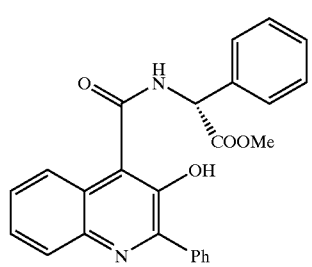 | (R) |
| 88 | 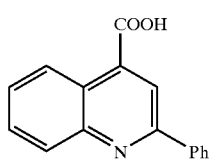 | 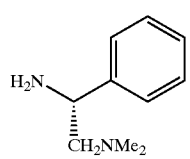 | 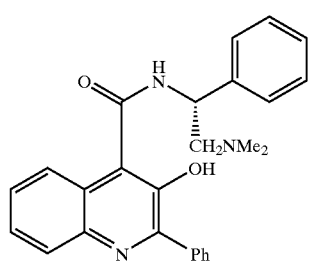 | (R) |

| Ex. | Molecular formula | M.W. | yield (%) | m.p. (° C.) (recryst. solv.) | $[\alpha]_D^{20}$ (c = 1, MeOH) |
|---|---|---|---|---|---|
| 50 | $C_{26}H_{22}N_2O_3$ | 410.48 | 46 | 128–129 (iPrOH) | |
| 51 | $C_{23}H_{18}N_2O_3S$ | 402.47 | 88 | 169–171 (iPrOH) | |
| 52 | $C_{27}H_{22}N_2O_3$ | 422.49 | 41 | 217–219 (EtOH abs.) | |
| 53 | $C_{23}H_{19}N_3O_3$ | 385.42 | 44 | 181–182 (iPrOH) | |
| 54 | $C_{22}H_{17}N_3O_3S$ | 403.45 | 50 | 209–211 (iPrOH) | |
| 55 | $C_{25}H_{20}N_2O$ | 364.45 | 95 | 183–184 (iPrOH) | |
| 56 | $C_{27}H_{26}N_2O$ | 394.52 | 77 | 155–156 (iPrOH/iPr$_2$O) | |
| 57 | $C_{26}H_{22}N_2O_3$ | 410.48 | 83 | 172–174 (iPrOH) | |
| 58 | $C_{30}H_{32}N_2O$ | 436.60 | 91 | 121–128 (iPr$_2$O) | |
| 59 | $C_{26}H_{22}N_2O_3$ | 410.48 | 79 | 180–182 (iPrOH) | |
| 60 | $C_{26}H_{22}N_2O_4$ | 426.48 | 62 | 182–183 (iPrOH) | |
| 61 | $C_{27}H_{24}N_2O$ | 392.51 | 82 | 164–165 (iPrOH) | |
| 62 | $C_{25}H_{20}N_2O_4$ | 412.45 | 50 | 226–227 (iPrOH) | |
| 63 | $C_{26}H_{20}N_2O_5$ | 440.46 | 70 | 186–187 (iPrOH) | |
| 64 | $C_{25}H_{22}N_2O$ | 366.47 | 75 | 173–174 (iPrOH) | |
| 65 | $C_{26}H_{24}N_2O$ | 380.49 | 90 | 160–162 (iPrOH) | |
| 66 | $C_{23}H_{19}N_3O_3$ | 385.42 | 10 | 202–204 (iPr$_2$O) | |
| 67 | $C_{25}H_{18}Cl_2N_2O_3$ | 465.34 | 59 | 164–165 (iPrOH) | |
| 68 | $C_{24}H_{21}N_3O$ | 367.45 | 49 | 139–141 (iPrOH/iPr$_2$O) | −6.9 (c=0.5) |
| 69 | $C_{25}H_{23}N_3O$ | 381.48 | 78 | 153–155 (iPrOH/iPr$_2$O) | −68.0 (c=0.5) |
| 70 | $C_{25}H_{21}ClN_2O$ | 400.91 | 58 | 137–139 (toluene/hexane) | −40.5 (c=0.5) |

TABLE 3-continued

| | | (II) + (III) → (I) | | | | |
|---|---|---|---|---|---|---|
| | 71 | $C_{25}H_{21}BrN_2O$ | 445.37 | 20 | 119–122 (toluene/hexane) | −41.4 (c=0.5) |
| | 72 | $C_{26}H_{24}N_2O$ | 380.49 | 59 | 165–166 (iPrOH) | |
| | 73 | $C_{25}H_{22}N_2O$ | 366.46 | 77 | 140–141 (iPrOH) | −26.7 |
| | 74 | $C_{25}H_{22}N_2O$ | 366.46 | 51 | 151–152 (iPrOH) | +26.6 |
| | 75 | $C_{25}H_{19}FN_2O_3$ | 414.44 | 44 | 174–176 (toluene/EtOAc) | |
| | 76 | $C_{25}H_{26}N_2O_3$ | 402.50 | 53 | 151–153 (EtOAc) | |
| | 77 | $C_{25}H_{19}ClN_2O_3$ | 430.90 | 68 | 161–163 (toluene/hexane) | |
| | 78 | $C_{25}H_{19}ClN_2O_3$ | 430.90 | 43 | 175–178 (toluene/hexane) | |
| | 79 | $C_{25}H_{22}N_2O_2$ | 382.47 | 47 | 168–169 (toluene) | |
| | 80 | $C_{27}H_{22}N_2O_5$ | 454.49 | 16 | 193–194 (toluene) | |
| | 81 | $C_{25}H_{20}N_2O_4$ | 412.40 | 32 | 178–180 (toluene) | |
| | 82 | $C_{25}H_{18}Cl_2N_2O_3$ | 465.34 | 61 | 142–143 (iPrOH) | |
| | 83 | $C_{25}H_{20}N_2O_4 \cdot HCl$ | 448.88 | 50 | 140 dec. ($Me_2CO$) | −7 |
| | 84 | $C_{29}H_{22}N_2O$ | 414.51 | 42 | 182–184 (EtOAc) | |
| | 85 | $C_{25}H_{22}N_2O_2$ | 382.47 | 66 | 122–125 ($iPr_2O$) | −28.4 (c=0.5) |
| | 86 | $C_{25}H_{22}N_2O_2$ | 382.47 | 66 | 122–125 (hexane/EtOAc) | +27.2 (c=0.5) |
| | 87 | $C_{25}H_{20}N_2O_4$ | 412.45 | 70 | 125–127 ($iPr_2O$) | +50 (c=0.5) |
| | 88 | $C_{26}H_{25}N_3O$ | 395.51 | 26 | 133–135 ($iPr_2O$/iPrOH) | −11.2 (c=0.5) |

(a) the phthalimido protecting group was removed by refluxing for 4h with hydrate hydrazine in 95% EtOH/1,2 dichloroethane, 9:1 respectively and then adding 37% HCl (up to pH=1) and refluxing an additional hour.

The compounds of the Examples 89–92 of general formula (I) (grouped in the following Table 4) were synthesized starting from other compounds of formula (I) (i.e. compounds of formula Ic) and following the synthetic procedures described in Example 10 (for compounds of the Examples 89, 90 and 91) and in Example 9 (for compound of the Example 92). Reaction yields are calculated on the purified, but unrecrystallized material. Analytical and spectroscopic data of the compounds of the Examples 89–92 are grouped in Table 5.

TABLE 4

| | (Ic) → (I) | | | |
|---|---|---|---|---|
| Ex. | (Ic) | (I) | Stereo chemistry | Molecular formula |
| 89 | [structure: quinoline-2-Ph with 4-carboxamide-NH-CH(Ph)-COOMe] | [structure: quinoline-2-Ph with 4-carboxamide-NH-CH(Ph)-COOMe₂] | (R,S) | $C_{26}H_{23}N_3O_2$ |
| 90 | [structure: quinoline-2-Ph with 4-carboxamide-NH-CH(Ph)-COOMe] | [structure: quinoline-2-Ph with 4-carboxamide-NH-CH(Ph)-CONH₂] | (R,S) | $C_{24}H_{19}N_3O_2$ |
| 91 | [structure: quinoline-2-Ph with 4-carboxamide-NH-CH(Ph)-COOMe] | [structure: quinoline-2-Ph with 4-carboxamide-NH-CH(Ph)-CO-pyrrolidine] | (R,S) | $C_{28}H_{25}N_3O_3$ |

TABLE 4-continued (Ic) → (I)

| 92 | [Structure: quinoline with COOMe and N-phenyl amide, 2-Ph] → [Structure: quinoline with COOH·HCl and N-phenyl amide, 2-Ph] (R) | $C_{24}H_{18}N_2O_3 \cdot HCl$ |

| Ex. | M.W. | yield (%) | m.p. (° C.) (recryst. solv.) | $[\alpha]_D^{20}$ (c = 1, MeOH) |
|---|---|---|---|---|
| 89 | 409.49 | 22 | 219–221 (iPrOH/EtOH) | |
| 90 | 381.43 | 95 | 237–238 (iPrOH/EtOH) | |
| 91 | 435.53 | 69 | 199–200 (iPrOH) | |
| 92 | 418.88 | 94 | 203–205 (acetone) | −40.0 (c = 0.5) |

TABLE 5

Analytical and spectroscopic data of compounds of Examples 16–92

| Ex. | Elemental analysis | IR (KBr); cm$^{-1}$ | MS (EI; source 200° C.; 70 eV; 200 μA) | 300 MHz $^1$H NMR (DMSO), 303 K |
|---|---|---|---|---|
| 16 | | 3240; 1750; 1640; 1595; 1545 | 398 (M+.); 232; 204 | 9.40(d, 1H); 8.30(d, 2H); 8.18(d, 1H); 8.13(d, 1H); 8.10 (s, 1H); 7.83(dd, 1H); 7.66(dd, 1H); 7.63–7.51(m, 3H); 5.87(s br, 1H); 5.70(m, 2H); 5.12(d, 1H); 3.80(s, 3H); 2.92–2.60(m, 4H). |
| 17 | Calcd. C, 78.51; H, 5.80; N, 7.32 Found C, 78.27; H, 5.83; N, 7.24 | 3400; 3200; 1640; 1595; 1532 | 337 (M-C$_2$H$_4$OH)+; 232; 204 | 9.20(d, 1H); 8.31(d, 2H); 8.14(d, 1H); 8.08(s, 1H); 8.04 (d, 1H); 7.82(dd, 1H); 7.64–7.51(m, 4H); 7.47(d, 2H); 7.37(dd, 2H); 7.27(dd, 1H); 5.10(dd, 1H); 4.81(d, 1H); 4.13(dq, 1H); 1.18(d, 3H). |
| 18 | Calcd. C, 78.76; H, 6.10; N, 7.07 Found C, 78.60; H, 6.08; N, 7.00 | 3260; 3220; 1632; 1550* | 396 (M+.); 367; 262; 219 | 9.24(d, 1H); 8.07(d, 1H); 7.97(dd, 2H); 7.76–7.70 (m, 1H); 7.62–7.51(m, 5H); 7.46((d, 2H); 7.39(dd, 2H); 7.29(dd, 1H); 5.10(dt, 1H); 3.52(s, 3H); 1.82(dq, 2H); 1.00(t, 3H). |
| 19 | Calcd. C, 82.43; H, 7.16; N, 6.63 Found C, 82.31; H, 7.20; N, 6.58 | 3240; 1630; 1540 | 423 (MH+)● | (353 K): 8.89(d br, 1H); 8.00(d, 1H); 7.70(dd, 1H); 7.60–7.42(m, 9H); 7.36(dd, 2H); 7.28(dd, 1H); 5.13(dt, 1H); 2.66(m, 2H); 1.90(ddq, 2H); 1.30(m, 2H); 1.00(t, 3H); 0.95(m, 2H); 0.57(t br, 3H). |
| 20 | Calcd. C, 77.04; H, 5.54; N, 6.42 Found C, 76.81; H, 5.54; N, 6.35 | 3290; 1760; 1645; 1590; 1532 | 436 (M+.); 377; 272; 271 | (353 K): 9.50(d, 1H); 8.08(d, 1H); 7.88((d, 1H); 7.80–7.72(m, 2H); 7.60(dd, 1H); 7.52(dd, 1H); 7.47–7.30 (m, 6H); 5.90(d, 1H); 2.60(t, 2H); 2.57(t, 2H); 2.26–2.06 (m, 2H). |
| 21 | Calcd. C, 82.63; H, 7.61; N, 6.22 Found C, 82.84; H, 7.64; N, 6.16 | 3270; 1635; 1550* | 450 (M+.); 421; 316 | (373 K): 8.71(d br, 1H); 7.99(d, 1H); 7.70(m, 2H); 7.52–7.42(m, 8H); 7.37(dd, 2H); 7.27(dd, 1H); 5.12(dt, 1H); 2.67(dd, 2H); 1.91(ddq, 2H); 1.36–1.26(m, 2H); 1.12–1.02(m, 2H); 1.00(t, 3H); 1.00–0.90(m, 4H); 0.76(t, 3H). |
| 22 | Calcd. C, 82.07; H, 6.36; N, 7.36 Found C, 81.95; H, 6.33; N, 7.30 | 3260; 1630; 1535 | 380 (M+.); 351; 246; 218 | (353 K): 8.90(d br, 1H); 8.01(d, 1H); 7.72(dd, 1H); 7.65 (d br, 1H); 7.60–7.49(m, 6H); 7.46(d, 2H); 7.38(dd, 2H); 7.24(dd, 1H); 5.12(dt, 1H); 2.30(s, 3H); 1.98–1.78 (m, 2H); 0.99(t, 3H). |
| 23 | Calcd. C, 82.07; H, 6.36; N, 7.36 Found C, 81.80; H, 6.37; N, 7.30 | 3260; 1630; 1535 | 380 (M+.); 351; 246; 218 | (353 K): 8.90(d br, 1H); 8.01(d, 1H); 7.72(dd, 1H); 7.65 (d br, 1H); 7.60–7.49(m, 6H); 7.46(d, 2H); 7.38(dd, 2H); 7.24(dd, 1H); 5.12(dt, 1H); 2.30(s, 3H); 1.98–1.78 (m, 2H); 0.99(t, 3H). |
| 24 | Calcd. C, 73.22; H, 5.20; N, 6.57 Found C, 72.88; H, 5.25; N, 6.44 | 3282; 1750; 1640; 1530 | 426 (M+.); 367; 277 | 9.65(d, 1H); 8.18(d, 1H); 8.11(d, 1H); 7.96(s, 1H); 7.83 (dd, 1H); 7.81(dd, 1H); 7.66(dd, 1H); 7.54–7.46(m, 3H); 7.44–7.33(m, 3H); 7.22(d, 1H); 7.13(dd, 1H); 5.80 (d, 1H); 3.87(s, 1H); 3.71(s, 3H). |
| 25 | Calcd. C, 84.13; H, 5.92; N, 6.33 Found C, 82.28; H, 5.86; N, 6.19 | 3250; 1630; 1545 | 442(M+.); 413; 308; 280 | 8.86(d, 1H); 8.13(d, 1H); 7.83(dd, 1H); 7.71–7.59 (m, 2H); 7.31–7.14(m, 12H); 7.04(d br, 2H); 4.75(dt, 1H); 1.58–1.42(m, 2H); 0.63(t br, 3H). |
| 26 | Calcd. C, 72.45; H, 4.62; N, 6.76 Found C, 72.19; H, 4.66; N, 6.69 | 3320; 1745; 1650; 1595 | 414 (M+.); 355; 250; 222 | 9.70(d, 1H); 8.21(d, 1H); 8.16(d, 1H); 8.07(dd, 1H); 7.90 (d, 1H); 7.86(dd, 1H); 7.72(dd, 1H); 7.64–7.55(m, 1H); 7.51(dd, 1H); 7.45–7.34(m, 4H); 5.80(d, 1H); 3,75 (s, 3H). |

TABLE 5-continued

Analytical and spectroscopic data of compounds of Examples 16–92

| Ex. | Elemental analysis | IR (KBr); cm$^{-1}$ | MS (EI; source 200° C.; 70 eV; 200 μA) | 300 MHz $^1$H NMR (DMSO), 303 K |
|---|---|---|---|---|
| 27 | Calcd. C, 69.03; H, 4.62; N, 6.44<br>Found C, 68.97; H, 4.63; N, 6.43 | 3250; 1650; 1585; 1550 | 434 (M+.); 405; 232; 204 | 9.50(d, 1H); 8.31(d, 2H); 8.15(d, 1H); 8.10(s, 1H); 8.00 (d, 1H); 7.81(dd, 1H); 7.72(d, 1H); 7.66(d, 1H); 7.64–7.52(m, 4H); 7.46(dd, 1H); 4.11(dt, 1H); 1.83(dq, 2H); 0.98(t, 3H). |
| 28 | Calcd. C, 78.24; H, 5.47; N, 7.60<br>Found C, 78.49; H, 5.58; N, 7.41 | 3260; 1645; 1590; 1550 | 368 (M+.); 337; 232; 204 | 9.22(d, 1H); 8.33(d, 2H); 8.18(s, 1H); 8.13(d, 2H); 7.81 (dd, 1H); 7.64–7.51(m, 4H); 7.46(d, 2H); 7.37(dd, 2H); 7.28(dd, 1H); 5.21(dt, 1H); 5.05(t, 1H); 3.71(dd, 2H). |
| 29 | Calcd. C, 81.93; H, 6.05; N, 7.64<br>Found C, 81.79; H, 6.06; N, 7.62 | 3260; 1650; 1595; 1550 | 366 (M+.); 337; 232; 204 | 9.24(d, 1H); 8.30(d, 2H); 8.14(d, 1H); 8.09(s, 1H); 8.02 (d, 1H); 7.82(dd, 1H); 7.63–7.51(m, 4H); 7.46(d, 2H); 7.38(dd, 2H); 7.24(dd, 1H); 5.14(dt, 1H); 1.95–1.78 (m, 2H); 0.98(t, 3H). |
| 30 | Calcd. C, 76.08; H, 5.40; N, 6.83<br>Found C, 75.88; H, 5.37; N, 7.08 | 3260; 1755; 1735; 1640; 1580; 1530 | 410 (M+.); 351; 261; 246; 217 | 9.70(d, 1H); 8.02(d, 1H); 7.76(dd, 1H); 7.70–7.47 (m, 9H); 7.47–7.34(m, 3H); 6.82(d, 1H); 3.75(s, 3H); 2.32 (s br, 3H). |
| 31 | Calcd. C, 82.08; H, 6.36; N, 7.36<br>Found C, 81.82; H, 6.34; N, 7.33 | 3220; 1630; 1550 | 380 (M+.); 351; 246; 217 | (353 K): 9.00(d, 1H); 8.01(d, 1H); 7.37(d(t, 1H); 7.60–7.48(m, 7H); 7.45(d, 2H); 7.38(dd, 2H); 7.28(dd, 1H); 5.10(dt, 1H); 2.28(s, 3H); 2.00–1.80(m, 2H); 1.00(t, 3H). |
| 32 | Calcd. C, 69.69; H, 4.45; N, 6.50<br>Found C, 69.58; H, 4.49; N, 6.49 | 3270; 1750; 1670; 1595; 1520 | 430 (M+.); 371; 266; 238; 203 | 9.78(d, 1H); 8.29(d, 2H); 8.24(d, 1H); 8.19(d, 1H); 8.16 (s, 1H); 7.73(dd, 1H); 7.61–7.49(m, 5H); 7.47–7.36 (m, 3H); 5.80(d, 1H); 3.79(s, 3H). |
| 33 | Calcd. C, 76.49; H, 5.40; N, 6.82<br>Found C, 76.74; H, 5.40; N, 6.88 | 3240; 1750; 1665; 1590; 1510; 1500 | 410 (M+.); 351; 246; 218 | 9.70(d, 1H); 8.26(d, 2H); 8.08(s, 1H); 8.03(d, 1H); 7.96 (s, 1H); 7.68(dd, 1H); 7.60–7.50(m, 5H); 7.48–7.36 (m, 3H); 5.80(d, 1H); 3.79(s, 3H); 2.50(s, 3H). |
| 34 | Calcd. C, 78.51; H, 5.79; N, 7.32,<br>Found C, 78.78; H, 5.78; N, 7.23 | 3220; 1740; 1695; 1535 | 382 (M+.); 337; 232; 204 | 9.35(d, 1H); 8.32(d, 2H); 8.14(d, 1H); 8.11(d, 1H); 8.10 (s, 1H); 7.84(dd, 1H); 7.64(dd, 1H); 7.61–7.54(m, 3H); 7.50(d, 2H); 7.40(dd, 2H); 7.30(dd, 1H); 5.41(dt, 1H); 3.73–3.60(m, 2H); 3.36(s, 3H). |
| 35 | Calcd. C, 69.69; H, 4.45; N, 6.50<br>Found C, 70.27; H, 4.46; N, 6.45 | 3240; 1750; 1670; 1590; 1550; 1500 | 430 (M+.); 371; 266; 238; 203 | 9.80(d, 1H); 8.29(d, 2H); 8.27(d, 1H); 8.21(s, 1H); 8.16 (d, 1H); 7.86(dd, 1H); 7.61–7.51(m, 5H); 7.48–7.38 (m, 3H); 5.80(d, 1H); 3.75(s, 3H). |
| 36 | Calcd. C, 76.40; H, 5.70; N, 6.60<br>Found C, 76.44; H, 5.72; N, 6.62 | 3240; 1760; 1640; 1540 | 425 (MH+)● | (353 K): 9.52(d, 1H); 8.01(d, 1H); 7.89 br, 1H); 7.74 (dd, 1H); 7.60(dd, 1H); 7.54–7.48(m, 7H); 7.44–7.33 (m, 3H); 4.88((1, 1H); 3.78(s, 3H); 2.91–2.68(m, 2H); 0.91 (t, 3H). |
| 37 | Calcd. C, 82.08; H, 6.36; N, 7.36<br>Found C, 82.21; H, 6.39; N, 7.34 | 3300; 1635; 1590; 1545 | 380 (M+.); 337; 232; 204 | 9.28(d, 1H); 8.14(d, 1H); 8.07(s, 1H); 8.01(d, 1H); 7.82 (dd, 1H); 7.64–7.51(m, 4H); 7.46(d, 2H); 7.39(dd, 2H); 7.28(dd, 1H); 5.15(dt, 1H); 1.94–1.69(m, 2H); 1.54–1.29 (m, 2H); 0.95(t, 3H). |
| 38 | Calcd. C, 82.20; H, 6.64; N, 7.10<br>Found C, 82.34; H, 6.64; N, 7.07 | 3240; 1640; 1550 | 395 (MH+); CI; gas reagent methane; P 5000 mTorr; source 150° C. | (353 K): 8.91(d, 1H); 8.00(d, 1H); 7.71(dd, 1H); 7.68–7.48(m, 7H); 7.45(d, 2H); 7.39(dd, 2H); 7.29(dd, 1H); 5.11(dt, 1H); 2.78–2.62(m, 2H); 2.00–1.80(m, 2H); 1.00 (t, 3H); 0.90(t br, 3H). |
| 39 | Calcd. C, 77.48; H, 4.93; N, 8.21<br>Found C, 77.25; H, 4.99; N, 8.07 | 3330; 1790; 1720; 1665; 1530 | 511 (M+.); 482; 377; 349; 321 | (353 K): 8.90(d, 1H); 8.20(d, 1H); 7.94(dd, 1H); 7.88–6.90(m, 5H); 7.74(d, 1H); 7.69(dd, 1H); 7.48–7.42 (m, 2H); 7.36–7.31(m, 3H); 7.25–7.20(m, 2H); 7.18–7.10 (m, 2H); 4.85(m, 1H); 1.73(ddq, 1H); 0.82(t, 3H). |
| 40 | Calcd. C, 82.32; H, 6.91; N, 6.86<br>Found C, 82.02; H, 6.95; N, 6.90 | 3250; 1635; 1550 | 408 (M+.); 379, 289, 274; 246 | (373 K): 8.72(d, 1H); 8.00(d, 1H); 7.70(dd, 1H); 7.55–7.42(m, 9H); 7.38(dd, 2H); 7.28(dd, 1H); 5.15(dt, 1H); 2.66(dd, 2H); 1.94(ddq, 2H); 1.33(m, 2H); 1.01(t, 3H); 0.56(t, 3H). |
| 41 | Calcd. C, 58.02; H, 4.12; N, 5.20; Br, 29.69<br>Found C, 58.14; H, 4.18; N, 5.22; Br, 29.44 | 3250; 1650; 1540 | 537/539/541 (MH+)● | (353 K): 8.95(d, 1H); 7.96(d, 1H); 7.83(dd, 1H); 7.76 (d, 1H); 7.71(d, 2H); 7.55(d, 2H); 7.45(dd, 2H); 7.39 (dd, 2H); 7.30(dd, 1H); 5.10(dt, 1H); 2.92(s, 3H); 2.30 (s, 3H); 1.88(ddq, 2H); 1.01(t, 3H). |
| 42 | Calcd. C, 67.98; H, 5.04; N, 6.10; Br, 17.39<br>Found C, 68.04; H, 5.02; N, 6.05; Br, 17.26 | 3260; 1640; 1540 | 459/461 (MH+)● | (353 K): 8.94(d br, 1H); 7.96(d, 1H); 7.81(dd, 1H); 7.76 (d, 1H); 7.60–7.49(m, 4H); 7.45(d, 2H); 7.40(dd, 2H); 7.30(dd, 1H); 5.10(dt, 1H); 2.30(s, 3H); 1.89(ddq, 2H); 1.01(t, 3H). |
| 43 | Calcd. C, 73.22; H, 5.20; N, 6.57<br>Found C, 73.41; H, 5.39; N, 6.61 | 3200; 1750; 1665; 1620; 1520 | 426 (M+.); 367; 262; 234 | 9.70(d, 1H); 8.24(d, 2H); 8.08(s, 1H); 8.05(d, 1H); 7.61 (d, 1H); 7.58–7.35(m, 9H); 5.80(d, 1H); 3.89(s, 3H); 3.74 (s, 3H). |
| 44 | Calcd. C, 74.30; H, 4.62; N, 6.42<br>Found C, 74.28; H, 4.61; N, 6.41 | 3200; 1750; 1660; 1590; 1550; 1525; 1500 | 436 (M+.); 337; 272; 244 | 9.80(d, 1H); 8.18(d, 1H); 8.11(d, 1H); 8.09(s, 1H); 7.90 (s, 1H); 7.87(dd, 1H); 7.80(d, 1H); 7.77(d, 1H); 7.67 (dd, 1H); 7.54(d, 2H); 7.47–7.31(m, 5H); 5.80(d, 1H); 3.78(s, 3H). |
| 45 | Calcd. C, 84.08; H, 5.65; N, 6.54<br>Found C, 84.13; H, 5.65; N, 6.51 | 3320; 1635; 1590; 1530 | 337 (M–C$_7$H$_7$)+; 232; 204; 91 | 9.32(AB<u>X</u>Y, 1H); 8.22(d, 2H); 8.09(d, 1H); 7.78 (dd, 1H); 7.77(s, 1H); 7.64–7.52(m, 6H); 7.50–7.28 (m, 9H); 5.53(AB<u>X</u>Y, 1H); 3.20(<u>A</u>BXY, 1H); 3.16 (A<u>B</u>XY, 1H). |
| 46 | Calcd. C, 70.91; H, 4.22; N, 6.89; F, 14.02<br>Found C, 70.86; H, 4.17; N, 6.92; F, 13.88 | 3300; 1655; 1590; 1540; 1500 | 406 (M+.); 386; 232; 204 | 10.15(d, 1H); 8.30(dd, 2H); 8.18(d, 1H); 8.10(s, 1H); 7.98(d, 1H); 7.86(dd, 1H); 7.75–7.42(m, 9H); 6.21 (m, 1H). |

TABLE 5-continued

Analytical and spectroscopic data of compounds of Examples 16–92

| Ex. | Elemental analysis | IR (KBr); cm$^{-1}$ | MS (EI; source 200° C.; 70 eV; 200 µA) | 300 MHz $^1$H NMR (DMSO), 303 K |
|---|---|---|---|---|
| 47 | Calcd. C, 78.74; H, 6.10; N, 7.06<br>Found C, 78.72; H, 6.10; N, 7.01 | 3250; 1635;<br>1550; 1500 | 396 (M+.); 367; 262; 219 | 9.24(d, 1H); 8.07(d, 1H); 7.97(dd, 2H); 7.76–7.70 (m, 1H); 7.62–7.51(m, 5H); 7.46(d, 2H); 7.39(dd, 2H); 7.29(dd, 1H); 5.10(dt, 1H); 3.52(s, 3H); 1.82(dq, 2H); 1.00(t, 3H). |
| 48 | Calcd. C, 82.18; H, 6.64; N, 7.10<br>Found C, 81.93; H, 6.64; N, 7.05 | 3250; 1630;<br>1540; 1500 | 394 (M+.); 365; 275; 260 | (353 K): 8.90(d br, 1H); 8.00(d, 1H); 7.70(dd, 1H); 7.56–7.42(m, 9H); 7.38(dd, 2H); 7.29(dd, 1H); 5.13(dt, 1H); 2.72(m, 2H); 1.90(ddq, 2H); 1.00(t, 3H); 0.90(t br, 3H). |
| 49 | Calcd. C, 74.90; H, 5.28; N, 6.99;<br>Found C, 74.67; H, 5.33; N, 7.03; | 3270; 1645;<br>1590; 1550;<br>1495; 770 | 400 (M+.); 371; 232; 204 | 9.20(d, 1H); 8.32(d, 2H); 8.08(dd, 2H); 8.06(s, 1H); 7.82 (t, 1H); 7.65–7.40(m, 8H); 5.00(dt, 1H); 1.93–1.73 (m, 2H); 0.98(t, 3H). |
| 50 | Calcd. C, 76.08; H, 5.40; N, 6.82<br>Found C, 76.16; H, 5.42; N, 6.84 | 1750; 1640;<br>1595; 1550 | 411 (MH+); 232; 204• | 8.32(d, 2H); 8.16(d, 1H); 8.10(s, 1H); 7.88(dd, 1H); 7.71 (dd, 1H); 7.60–7.42(m, 9H); 3.86(s, 3H); 2.56(s, 3H). |
| 51 | Calcd. C, 68.64; H, 4.51; N, 6.96<br>Found C, 68.52; H, 4.53; N, 6.94 | 3290; 1740;<br>1640; 1590;<br>1530 | 402 (M+.); 343; 238; 210 | 9.72(d, 1H); 8.47(dd, 1H); 8.15(d, 1H); 8.07(d, 1H); 8.05 (s, 1H); 7.96(dd, 1H); 7.81(dd, 1H); 7.71(dd, 1H); 7.62 (dd, 1H); 7.53(d, 2H); 7.46–7.36(m, 3H); 5.78(d, 1H); 3.78(s, 3H). |
| 52 | Calcd. C, 76.76; H, 5.25; N, 6.63<br>Found C, 76.39; H, 5.25; N, 6.55 | 3250; 1750;<br>1660; 1590;<br>1520 | 422 (M+.); 258; 230 | 9.70(d, 1H); 8.45(dd, 1H); 8.18(d, 1H); 7.80–7.38 (m, 11H); 5.83(d, 1H); 3.79(s, 3H); 3.20–2.80(s br, 4H). |
| 53 | Calcd. C, 71.68; H, 4.97; N, 10.90<br>Found C, 71.39; H, 4.99; N, 10.81 | 3410; 3250;<br>1740; 1678;<br>1600* | 385 (M+.); 221; 193 | 11.68(s br, 1H); 9.71(d, 1H); 8.17((d, 1H); 7.99(d, 1H); 7.86(s, 1H); 7.66(dd, 1H); 7.58–7.35(m, 6H); 7.00(s br, 2H); 6.22(s br, 1H); 5.75(d, 1H); 3.73(s, 3H). |
| 54 | Calcd. C, 65.50; H, 4.25; N, 10.42<br>Found C, 65.48; H, 4.22; N, 10.38 | 3300; 1755;<br>1645; 1585;<br>1530 | 344 (M−COOCH$_3$)+;<br>239; 211 | 9.82(d, 1H); 8.28(s, 1H); 8.19(d, 1H); 8.14(d, 1H); 8.10 (d, 1H); 8.00(d, 1H); 7.88(dd, 1H); 7.73(dd, 1H); 7.53 (d, 2H); 7.47–7.36(m, 3H); 5.80(d, 1H); 3.78(s, 3H). |
| 55 | Calcd. C, 82.39; H, 5.53; N, 7.69<br>Found C, 82.31; H, 5.52; N, 7.65 | 3240; 1640;<br>1590; 1545 | 365 (MH)+• | 9.20(d, 1H); 8.31(d, 2H); 8.27(d, 1H); 8.16(s, 1H); 8.14 (d, 1H); 7.85(dd, 1H); 7.68(dd, 1H); 7.62–7.46(m, 4H); 7.32–7.23(m, 3H); 5.69(dt, 1H); 3.08–2.85(m, 2H); 2.64–2.52(m, 1H); 2.10–1.96(m, 1H). |
| 56 | Calcd. C, 82.20; H, 6.64; N, 7.10<br>Found C, 82.29; H, 6.66; N, 7.05 | 3270; 1640;<br>1590; 1540 | 394 (M+.); 337; 232; 204 | 9.12(d, 1H); 8.30(d, 2H); 8.14(d, 1H); 8.07(s, 1H); 8.02 (d, 1H); 7.82(dd, 1H); 7.64–7.52(m, 4H); 7.46(d, 2H); 7.39(dd, 2H); 7.28(dd, 1H); 5.13(dt, 1H); 1.96–1.71 (m, 2H); 1.48–1.27(m, 4H); 0.9(t, 3H). |
| 57 | Calcd. C, 76.08; H, 5.40; N, 6.82<br>Found C, 75.92; H, 5.44; N, 6.77 | 3300; 1752;<br>1642, 1590;<br>1530 | 410 (M+.); 351; 246;<br>218; 203 | 9.74(d, 1H); 8.20(d, 2H); 8.18(d, 1H); 8.12(d, 1H); 8.08 (s, 1H); 7.82(dd, 1H); 7.64(dd, 1H); 7.54(d, 2H); 7.47–7.36(m, 5H); 5.8(d, 1H); 3.79(s, 3H); 2.40(s, 3H). |
| 58 | Calcd. C, 82.53; H, 7.39; N, 6.42<br>Found C, 82.59; H, 7.45; N, 6.39 | 3260; 1650;<br>1590; 1550;<br>1540 | 337 (M−C$_7$H$_{15}$)+; 249;<br>232; 204 | 9.28(d, 1H); 8.29(d, 2H); 8.14(d, 1H); 8.07(s, 1H); 8.02 (d, 1H); 7.82(dd, 1H); 7.64–7.52(m, 4H); 7.46(d, 2H); 7.38(dd, 2H); 7.28(dd, 1H); 5.14(dt, 1H); 1.98–1.71 (m, 2H); 1.30–1.20(m, 10H); 0.86(t br, 3H). |
| 59 | Calcd. C, 76.08; H, 5.40; N, 6.82<br>Found C, 76.21; H, 5.40; N, 6.79 | 3400–3100;<br>1742; 1665;<br>1590; 1530 | 410 (M+.); 261; 218 | 9.70(d, 1H); 8.22(d, 1H); 8.10(d, 1H); 7.84(dd, 1H); 7.70 (dd, 1H); 7.67(s, 1H); 7.56(d, 1H); 7.50(dd, 2H); 7.45–7.33(m, 5H); 5.80(d, 1H); 3.78(s, 3H); 2.42(s, 3H). |
| 60 | Calcd. C, 73.22; H, 5.20; N, 6.57<br>Found C, 72.89; H, 5.20; N, 6.48 | 3300; 1750;<br>1645; 1590;<br>1520 | 426 (M+.); 367; 262;<br>234; 219; 191 | 9.72(d, 1H); 8.25(d, 2H); 8.17(d, 1H); 8.09(d, 1H); 8.07 (s, 1H); 7.80(dd, 1H); 7.62(dd, 1H); 7.54(dd, 2H); 7.46–7.36(m, 3H); 7.12(d, 2H); 5.80(d, 1H); 3.89(s, 3H); 3.75 (s, 3H). |
| 61 | Calcd. C, 82.62; H, 6.16; N, 7.14<br>Found C, 82.76; H, 6.18; N, 7.19 | 3230; 1640;<br>1590; 1550* | 392 (M+.); 249; 232, 204 | 9.00(s, 1H); 8.32(dd, 2H); 8.13(d, 1H); 8.05(s, 1H); 7.93 (d, 1H); 7.81(dd, 1H); 7.64–7.52(m, 6H); 7.39(dd, 2H); 7.26(dd, 1H); 2.61–2.50(m, 2H); 2.10–2.00(m, 2H); 2.00–1.75(m, 4H). |
| 62 | Calcd. C, 72.80; H, 4.89; N, 6.79<br>Found C, 72.86; H, 4.91; N, 6.75 | 3500–3100;<br>1750; 1670;<br>1610; 1590 | 412 (M+.); 353; 248; 220 | 9.90(s, 1H); 9.70(d, 1H); 8.14(d, 2H); 8.14(d, 1H); 8.06 (d, 1H); 8.01(s, 1H); 7.78(dd, 1H); 7.60(dd, 1H); 7.53 (dd, 2H); 7.46–7.35(m, 3H); 6.94(d, 2H); 5.80(d, 3H); 3.75(s, 3H). |
| 63 | Calcd. C, 70.90; H, 4.58; N, 6.36<br>Found C, 70.73; H, 4.59; N, 6.35 | 3350; 1735;<br>1655; 1590 | 440 (M+.); 381; 276; 248 | 9.70(d, 1H); 8.17(d, 1H); 8.09(d, 1H); 8.06(s, 1H); 7.88 (d, 1H); 7.85(dd, 1H); 7.80(dd, 1H); 7.62(dd, 1H); 7.42 (dd, 2H); 7.46–7.36(m, 3H); 7.10(d, 2H); 6.13(s, 2H); 5.73(d, 1H); 3.73(s, 3H). |
| 64 | Calcd. C, 81.94; H, 6.05; N, 7.64<br>Found C, 82.02; H, 6.07; N, 7.60 | 3220; 1640;<br>1590; 1545 | 366 (M+.); 351; 248;<br>232; 204 | 9.01(s br, 1H); 8.34(dd, 2H); 8.15(s, 1H); 8.13(d, 1H); 8.01(d, 1H); 7.81(dd, 1H); 7.66–7.52(m, 6H); 7.39 (dd, 2H); 7.25(dd, 1H). |
| 65 | Calcd. C, 82.07; H, 6.36; N, 7.36<br>Found C, 82.15; H, 6.36; N, 7.41 | 3320; 1640;<br>1590; 1530 | 380 (M+.); 351; 232; 204 | 9.20(d, 1H); 8.29(dd, 2H); 8.14(d, 1H); 8.06(s, 1H); 8.03 (d, 1H); 7.81(dd, 1H); 7.64–7.50(m, 4H); 7.34(d, 2H); 7.19(d, 2H); 5.00(dt, 1H); 2.30(s, 3H); 1.93–1.73(m, 2H); 0.98(t, 3H). |
| 66 | Calcd. C, 71.68; H, 4.97; N, 10.90<br>Found C, 70.42; H, 4.99; N, 10.56 | 3360; 3240;<br>1750; 1630;<br>1600; 1560 | 385 (M+.); 326; 221; 193 | 11.20(s br, 1H); 9.65(d, 1H); 8.05(d, 1H); 7.93(d, 1H); 7.78(s, 1H); 7.70(dd, 1H); 7.67(m, 1H); 7.55–7.34 (m, 6H); 6.87(m, 1H); 6.80(m, 1H); 6.77(d, 1H); 3.75 (s, 3H). |
| 67 | Calcd. C, 64.53; H, 3.90; N, 6.02;<br>Cl, 15.24<br>Found C, 64.59; H, 3.95; N, 5.94;<br>Cl, 15.03 | 3200; 1755;<br>1635; 1590;<br>1535 | 464 (M+.); 405; 300;<br>272; 237 | 9.70(d, 1H); 8.55(d, 1H); 8.30(dd, 1H); 8.22(d, 1H); 8.21 (s, 1H); 8.17(d, 1H); 7.86(dd, 1H); 7.84(d, 1H); 7.70 (dd, 1H); 7.54(dd, 2H); 7.47–7.36(m, 3H); 5.78(d, 1H); 3.74(s, 3H). |

TABLE 5-continued

Analytical and spectroscopic data of compounds of Examples 16–92

| Ex. | Elemental analysis | IR (KBr); cm$^{-1}$ | MS (EI; source 200° C.; 70 eV; 200 μA) | 300 MHz $^1$H NMR (DMSO), 303 K |
|---|---|---|---|---|
| 68 | | 3300; 1635; 1590; 1530; 1495; 770 | 338; 337; 255; 233; 232; 204 | 9.18(d br, 1H); 8.35(d, 2H); 8.20(s, 1H); 8.13(d, 1H); 8.07(d, 1H); 7.81(dd, 1H); 7.63–7.51(m, 4H); 7.44 (d, 2H); 7.38(dd, 2H); 7.28(dd, 2H); 5.08(dt br, 1H); 2.89 (d, 2H); 1.60(s br, 2H). |
| 69 | Calcd. C, 78.71; H, 6.08; N, 11.01 Found C, 78.45; H, 6.10; N, 10.96 | 3490; 3380; 3260; 1630; 1600 | 381 (M+.); 352; 247; 219; 218 | 9.20(d, 1H); 7.87(m, 1H); 7.70(d, 2H); 7.59–7.26 (m, 11H); 5.08(dt, 1H); 4.80(s br, 2H); 2.81(dq, 2H); 0.95(t, 3H). |
| 70 | Calcd. C, 74.90; H, 5.28; N, 6.99; Cl, 8.84 Found C, 74.88; H, 5.25; N, 6.98; Cl, 8.92 | 3230; 1640; 1550 | 400 (M+.); 371; 266; 238; 203 | 9.37(d, 1H), 8.10(d, 1H); 7.85(dd, 1H); 7.75–7.35 (m, 12H); 5.07(dt, 1H); 1.80(dq, 2H); 0.98(t, 3H). |
| 71 | Calcd. C, 67.42; H, 4.75; N, 6.29; Br, 17.94 Found C, 67.57; H, 4.80; N, 6.31; Br, 18.00 | 3240; 1640; 1545 | 444/446 (M+.); 415/417; 310/312; 203 | 9.35(d, 1H); 8.10(d, 1H); 7.85(dd br, 1H); 7.70–7.30 (m, 12H); 5.05(dt, 1H); 1.81(dq, 2H); 0.99(t, 3H). |
| 72 | Calcd. C, 82.07; H, 6.36; N, 7.36 Found C, 82.00; H, 6.36; N, 7.33 | 3240; 1630; 1590; 1545 | 381 (MH)+; TSP, ammonium acetate (50 mM)/acetonitrile 60:40 as eluent; source 250° C. | 9.24(d, 1H); 8.29(d, 2H); 8.14(d, 1H); 8.01(s, 1H); 7.96 (d, 1H); 7.81(dd, 1H); 7.64–7.51(m, 4H); 7.47–7.36 (m, 4H); 7.29(dd, 1H); 4.90(dd, 1H); 2.19–2.02 (m, 1H); 1.08(d, 3H); 0.80(d, 3H). |
| 73 | Calcd. C, 81.94; H, 6.05; N, 7.64 Found C, 79.33; H, 5.82; N, 7.34 | 3320; 1635; 1590; 1535 | 366 (M+.); 337; 232; 204 | 9.24(d, 1H); 8.30(d, 2H); 8.14(d, 1H); 8.09(s, 1H); 8.02 (d, 1H); 7.82(dd, 1H); 7.63–7.51(m, 4H); 7.46(d, 2H); 7.38(dd, 2H); 7.24(dd, 1H); 5.14(dt, 1H); 1.95–1.78 (m, 2H); 0.98(t, 3H). |
| 74 | Calcd. C, 81.94; H, 6.05; N, 7.64 Found C, 82.08; H, 6.09; N, 7.59 | 3280; 1637; 1590; 1540 | 366 (M+.); 337; 232; 204 | 9.24(d, 1H); 8.30(d, 2H); 8.14(d, 1H); 8.09(s, 1H); 8.02 (d, 1H); 7.82(dd, 1H); 7.63–7.51(m, 4H); 7.46(d, 2H); 7.38(dd, 2H); 7.24(dd, 1H); 5.14(dt, 1H); 1.95–1.78 (m, 2H); 0.98(t, 3H). |
| 75 | Calcd. C, 72.45; H, 4.62; N, 6.76 Found C, 72.28; H, 4.59; N, 6.79 | 3280; 1740; 1650; 1630; 1550 | 414 (M+.); 355; 250; 222 | 9.75(d, 1H); 8.28(dd, 2H); 8.21(dd, 1H); 8.2(s, 1H); 7.95 (dd, 1H); 7.77(ddd, 1H); 7.61–7.50(m, 5H); 7.47–7.36 (m, 3H); 5.80(d, 1H); 3.74(s, 3H). |
| 76 | Calcd. C, 74.60; H, 6.51; N, 6.96 Found C, 74.32; H, 6.50; N, 6.90 | 1740; 1665; 1595; 1535 | 402 (M+.); 238; 210 | 9.61(d, 1H); 8.11(d, 1H); 7.99(d, 1H); 7.75(dd, 1H); 7.59 (dd, 1H); 7.50 (d, 2H); 7.47–7.35(m, 4H); 5.74(d, 1H); 3.72(s, 3H); 2.90(tt, 1H); 2.00–1.20(1H, 10H). |
| 77 | Calcd. C, 69.69; H, 4.45; N, 6.50 Found C, 69.81; H, 4.45; N, 6.54 | 3290; 1745; 1660; 1640; 1585; 1530 | 431 (MH+)● | 9.71(d, 1H); 8.37(s, 1H); 8.30–8.15(m, 3H); 7.85 (dd, 1H); 7.69(dd, 1H); 7.63–7.38(m, 8H); 5.79(d, 1H); 3.74(s, 3H). |
| 78 | Calcd. C, 69.69; H, 4.44; N, 6.50 Found C, 69.90; H, 4.42; N, 6.57 | 3290; 1745; 1660; 1600; 1520 | 431 (MH+); TSP, ammonium acetate (0.1 M/acetonitrile 60:40 as eluent; source 250° C. | 9.70(d, 1H); 8.24(d, 1H); 8.14(d, 1H); 7.87(dd, 1H); 7.77(s, 1H); 7.76–7.62(m, 3H); 7.58–7.48(m, 4H); 7.44–7.34(m, 3H); 5.80(d, 1H); 3.72(s, 3H). |
| 79 | Calcd. C, 78.51; H, 5.80; N, 7.32 Found C, 78.55; H, 5.82; N, 7.26 | 3310; 3110; 1645; 1575; 1535 | 382 (M+.); 353; 264; 247; 219 | 9.80(s, 1H); 9.11(d, 1H); 8.00–7.94(m, 3H); 7.61–7.42 (m, 8H); 7.38(dd, 2H); 7.28(dd, 1H); 5.06(dt, 1H); 1.82 (ddq, 2H); 0.97(t, 3H). |
| 80 | Calcd. C, 71.36; H, 4.88; N, 6.16 Found C, 71.39; H, 4.88; N, 6.17 | 3320; 1760; 1735; 1650; 1530 | 455 (MH)+● | 9.74(d, 1H); 8.24(dd, 2H); 8.17(s, 1H); 8.08(dd, 1H); 7.70–7.50(m, 7H); 7.46–7.35(m, 3H); 5.75(d, 1H); 3.75 (s, 3H). |
| 81 | Calcd. C, 72.80; H, 4.89; N, 6.79 Found C, 73.24; H, 5.00; N, 6.42 | 3360; 3300; 1745; 1650; 1600; 1560; | 413 (MH)+● | 9.69(d, 1H); 9.68(s, 1H); 8.49(d, 2H); 8.12(s, 1H); 7.64–7.35(m, 10H); 7.18(d, 1H); 5.79(d, 1H); 3.77(s, 3H). |
| 82 | Calcd. C, 64.53; H, 3.90; N, 6.02 Found C, 64.71; H, 3.96; N, 6.00 | 3240; 1740; 1645; 1595; 1550 | 464 (M+.); 405; 300; 272; 237 | 10.68(d, 1H); 8.25(d, 1H); 8.14(d, 1H); 7.88(dd, 1H); 7.82(d, 1H); 7.78(s, 1H); 7.74(dd, 1H); 7.74(d, 1H), 7.62 (dd, 1H); 7.51(d, 2H); 7.44–7.33(m, 3H); 6.78(d, 1H); 3.74(s, 3H). |
| 83 | Calcd. C, 66.89; H, 4.72; N, 6.24; Cl, 7.90 Found C, 66.53; H, 4.74; N, 6.10; Cl, 7.48 | 3180; 1750; 1660; 1645; 1610; 1535; 1510 | 412 (M+.); 353; 232; 204 | 9.62(d, 1H); 8.28(d, 2H); 8.22(d, 1H); 8.16(d, 1H); 8.11 (s, 1H); 7.86(dd, 1H); 7.68(dd, 1H); 7.61–7.51(m, 3H); 7.30(d, 2H); 6.80(d, 1H); 5.61(d, 1H); 3.71(s, 3H). |
| 84 | Calcd. C, 84.03; H, 5.35; N, 6.76 Found C, 83.27; H, 5.64; N, 7.05 | 3210; 1640; 1590; 1525 | 414 (M+.); 337; 232; 204 | 9.79(d, 1H); 8.30(dd, 2H); 8.15(s, 1H); 8.12(d, 1H); 8.02 (d, 1H); 7.81(dd, 1H); 7.63–7.26(m, 14H); 6.52(d, 1H). |
| 85 | Calcd. C, 78.51; H, 5.80; N, 7.33 Found C, 78.49; H, 5.84; N, 7.26 | 3370; 1625; 1525 | 382 (M+.); 264; 247; 219 | 9.80(s, 1H); 9.11(d, 1H); 8.00–7.94(m, 3H); 7.61–7.42 (m, 8H); 7.38(dd, 2H); 7.28(dd, 1H); 5.06(dt, 1H); 1.82 (ddq, 2H); 0.97(t, 3H) |
| 86 | Calcd. C, 78.51; H, 5.80; N, 7.33 Found C, 78.55; H, 5.84; N, 7.30 | 3270; 1650; 1630; 1570; 1535 | 382 (M+.); 264; 247; 219 | 9.80(s, 1H); 9.11(d, 1H); 8.00–7.94(m, 3H); 7.61–7.42 (m, 8H); 7.38(dd, 2H); 7.28(dd, 1H); 5.06(dt, 1H); 1.82 (ddq, 2H); 0.97(t, 3H). |
| 87 | Calcd. C, 72.80; H, 4.89; N, 6.79 Found C, 72.12; H, 4.88; N, 6.63 | 3360; 1735; 1625; 1530 | 412 (M+.); 353; 248; 219 | 9.85(s, 1H); 9.63(d br, 1H); 7.97(m, 3H); 7.89(d br, 1H); 7.62–7.34(m, 10H); 5.75(d, 1H); 3.76(s, 3H). |
| 88 | Calcd. C, 78.96; H, 6.37; N, 10.62 Found C, 78.63; H, 6.39; N, 10.65 | 3320; 1640; 1590; 1525; 770 | 395 (M+.); 232; 204 | 9.15(d, 1H); 9.30(d, 2H); 9.18(dd, 2H); 8.06(s, 1H); 7.80(t, 1H); 7.70–7.20(m, 9H); 5.30(dt, 1H); 2.75 (dd, 1H); 2.45(dd, 1H); 2.70(s, 6H). |
| 89 | Calcd. C, 76.26; H, 5.66; N, 10.26 Found C, 75.74; H, 5.66; N, 10.06 | 3280; 1660; 1635; 1590 | 409 (M+.); 337; 232; 204 | 9.40(d, 1H); 8.26(d, 2H); 8.22(d, 1H); 8.12(d, 1H); 8.05 (s, 1H); 7.81(dd, 1H); 7.62(dd, 1H); 7.59–7.49(m, 5H); 7.43–7.33(m, 3H); 6.15(d, 1H); 3.00(s, 3H); 2.90(s, 3H). |

TABLE 5-continued

Analytical and spectroscopic data of compounds of Examples 16–92

| Ex. | Elemental analysis | IR (KBr); cm$^{-1}$ | MS (EI; source 200° C.; 70 eV; 200 μA) | 300 MHz $^1$H NMR (DMSO), 303 K |
|---|---|---|---|---|
| 90 | Calcd. C, 75.57; H, 5.02; N, 11.02<br>Found C, 75.23; H, 5.12; N, 10.88 | 3360; 3270; 1680; 1650; 1600 | 381 (M+.); 337; 232; 204 | 9.40(d, 1H); 8.31(d, 2H); 8.16(s, 1H); 8.15(d, 1H); 8.12 (d, 1H); 7.81(dd, 1H); 7.78(s br, 1H); 7.64–7.50(m, 6H); 7.41–7.30(m, 3H); 7.23(s br, 1H); 5.71(d, 1H). |
| 91 | Calcd. C, 77.22; H, 5.79; N, 9.65<br>Found C, 76.91; H, 5.87; N, 9.56 | 3220; 1660; 1620; 1590 | 436 (MH+); TSP, ammonium acetate (0.1 M)/acetonitrile 60:40 as eluent; source 250° C. | 9.48(d, 1H); 8.27(d, 2H); 8.23(d, 1H); 8.12(d, 1H); 8.06 (s, 1H); 8.02(dd, 1H); 7.63(dd, 1H); 7.60–7.50(m, 5H); 7.45–7.33(m, 3H); 5.92(d, 1H); 3.82–3.71(m, 1H); 3.53–3.26(m, 2H); 3.16–3.08(m, 1H); 1.98–1.68(m, 4H). |
| 92 | Calcd. C, 68.82; H, 4.57; N, 6.69; Cl, 8.46<br>Found C, 68.42; H, 4.60; N, 6.56; Cl, 8.22 | 1740; 1670; 1635; 1610; 1540 | 382 (M+.); 337; 204 | 9.64(d, 1H); 8.28(d, 2H); 8.22(d, 1H); 8.16(d, 1H); 8.13 (s, 1H); 7.84(dd, 1H); 7.66(dd, 1H); 7.62–7.51(m, 5H); 7.46–7.34(m, 3H); 5.70(d, 1H). |

*oil mull;
•FAB POS, thioglycerol matrix, Xe gas, 8 KeV, source 50° C.

EXAMPLE 93

(R,S)-N-[α-(Methoxycarbonyl)benzyl]-2-(p-chlorophenyl)quinoline-4-carboxamide 2 g (7.0 mmol) of 2-(p-chlorophenyl)quinoline-4-carboxylic acid and 1.7 ml (15.4 mmol) of N-methylmorpholine were dissolved, under nitrogen athmosphere, in 50 ml of dry THF.

The solution was cooled to −20° C. and 0.91 ml (7.0 mmol) of isobutyl chloroformate were added. After 20 minutes, 2.12 g (10.5 mmol) of methyl (R,S) phenylglycinate hydrochloride and 1.3 ml (11.9 mmol) of N-methylmorpholine, dissolved in 30 ml of dry THF, were added and the reation mixture was stirred at room temperature overnight.

5 ml of H$_2$O were added and the reaction mixture was evaporated in vacuo to dryness. The residue was dissolved in Et$_2$O, washed with a saturated solution of NaHCO$_3$, separated, dried over Na$_2$SO$_4$ and evaporated in vacuo to dryness.

The residual oil was flash chromatographed on 230–400 mesh silica gel, eluting with a mixture of hexane/isopropyl ether 7:3 to afford 0.9 g of crude produce, which was recrystallized three times with iPrO$_2$/toluene to yield 0.5 g of the title compound.

C$_{25}$H$_{19}$ClN$_2$O$_3$

M.P.=170–172 ° C.

M.W.=430.90

Elemental analysis: Calcd. C, 69.72; H, 4.45; N, 6.50 Found C, 69.82; H. 4.47; N, 6.48

I.R. (KBr): 3280; 1740; 1670; 1635; 1590; 1530 cm$^{-1}$.

300 MHz 1H-NMR (DMSO-d6): 9.71 (d, 1H); 8.32 (d, 2H); 8.21 (d, 1H); 8.13 (d, 1H); 8.13 (s, 1H); 7.85 (dd, 1H); 7.67 (dd, 1H); 7.63 (d, 2H); 7.53 (dd, 2H); 7.46–7.38 (m, 3H); 5.79 (d, 1H); 3.74 (s, 3H).

MS (EI; source 200° C.; 70 eV; 200 μA): 430 (M+.); 371; 266; 238; 203.

EXAMPLE 94

(R)-,N-[α-(Methoxycarbonyl)-4-methoxybenzyl]-2-phenylquinoline-4-carboxamide 0.62 g (1.5 mmol) of (R)-N-[α-(methoxycarbonyl)-4-hydroxybenzyl]-2-phenylquinoline-4-carboxamide (compound of Ex. 83) were dissolved in 30 ml of dry acetone and 2 ml of dry DMF; 0.14 g (0.75 mmol) of K$_2$CO$_3$ were added and the reaction mixture was stirred for 30 minutes.

0.093 ml (1.5 mmol) of methyl iodide were added at room temperature and the reaction mixture was heated at 40° C. for 4 hours. 0.104 g (0.75 mmol) of K$_2$CO$_3$ and 0.093 ml (1.5 mmol) of methyl iodide were added again, and the mixture refluxed for additional 6 hours.

The mixture was evaporated in vacuo to dryness, dissolved in EtOAc and washed with H$_2$O. The organic layer, dried over Na$_2$SO$_4$, was evaporated in vacuo to dryness. The residue was recrystallized from Et$_2$O to yield 0.45 g of the title compound.

C$_{26}$H$_{22}$N$_2$O$_4$

M.P.=160–162 ° C.

M.W.=426.48

Elemental analysis: Calcd. C, 73.22; H. 5.20; N, 6.57 Found C, 73.01; H. 5.20: N, 6.48

I.R. (KBr): 3210; 1750; 1635; 1625; 1590; 1530; 1515 cm$^{-1}$

300 MHz 1H-NMR (DMSO-d6): 9.65 (d, 1H); 8.28 (d, 2H); 8.21 (d, 1H); 8.14 (d, 1H); 8.10 (s, 1H); 7.84 (dd, 1H); 7.67 (dd, 1H); 7.61–7.49 (m, 3H); 7.44 (d, 2H); 6.98 (d, 2H); 4.70 (d, 1H); 3.79 (s, 3H); 3.76 (s, 3H).

MS (EI; source 200° C.; 70 eV; 200 μA): 426 (M+.); 367; 232; 204.

EXAMPLE 95

(R,S)-N-[α-(Methoxycarbonyl)-α-(methyl)benzyl]-N-methyl-2-phenylquinoline-4-carboxamide hydrochloride 0.50 g (1.3 mmol) of (R,S)-N-[α-(methoxycarbonyl) benzyl]-2-phenylquinoline-4-carboxamide (compound of Ex. 4) were dissolved, under nitrogen athmosphere, in 10 ml of dry DMF.

The solution was cooled to 0° C. and 0.052 g (1.3 mmol) of NaH (60%) were added; after 20 minutes at 0° C. the temperature was raised to r.t. and 0.09 ml (1.4 mmol) of MeI were added. The reation mixture was stirred at room temperature overnight, then the procedure was repeated by adding additional 0.052 g (1.3 mmol) of NaH (60%) and 0.1 ml (1.6 mmol) of MeI.

After 6 hours at room temperature, 10 ml of saturated solution of NH$_4$Cl were added and the reaction mixture was evaporated in vacuo to dryness. The residue was dissolved in $CH_2Cl_2$ and washed with water; the organic layer was separated, dried over $Na_2SO_4$ and evaporated in vacuo to dryness.

The residual oil was flash chromatographed on 230–400 mesh silica gel, eluting with a mixture of hexane/ethyl acetate 3:2 containing 0.5% of conc. $NH_4OH$ to afford 0.18 g of a crude product which was dissolved in $Et_2O$ and treated with $HCl/Et_2O$ to yield 0.15 g of the title compound.

$C_{27}H_{24}N_2O_3 \cdot HCl$
M.W.=460.96
I.R. (KBr): 1745; 1640; 1610 cm$^{-1}$.
MS (EI; source 200° C.; 70 eV; 200 μA): 424 (M+.); 365; 232; 204.

EXAMPLE 96

(R,S)-N-[α-(Methylcarbonyl)benzyl]-2-phenylquinoline-4-carboxamide 0.27 ml (3.1 mmol) of oxalyl chloride were dissolved, under nitrogen athmosphere, in 2.3 ml of dry $CH_2Cl_2$.

The solution was cooled to –55° C. and 0.22 ml (3.1 mmol) of DMSO, dissolved in 0.7 ml of dry $CH_2Cl_2$, were added dropwise maintaining the temperature below –50° C. The reaction was stirred at –55° C. for 7 minutes then 0.97 g (2.5 mmol) of (R,S)-N-[α-(1-hydroxyethyl)benzyl]-2-phenylquinoline-4-carboxamide (compound of Ex. 17), dissolved in 25 ml of dry $CH_2Cl_2$, were added keeping the temperature between –50 and –55° C.

After 30 minutes at –55° C., 1.9 ml (13.6 mmol) of TEA were added without exceeding –40° C., then the reaction mixture was allowed to reach room temperature and stirred for additional 15 minutes.

The reaction was quenched with 5 ml of $H_2O$ and extracted with $CH_2Cl_2$; the organic layer was washed with $H_2O$, 20% citric acid, saturated solution of $NaHCO_3$ and brine; the organic layer was separated, dried over $Na_2SO_4$ and evaporated in vacuo to dryness.

The residual oil was flash chromatographed on 230–400 mesh silica gel, eluting with a mixture of hexane/ethyl acetate 70:30 containing 0.5% of conc. $NH_4OH$ to afford 0.64 g of a crude product which was triturated with warm $i-Pr_2O/i-PrOH$ 2:1, filtered, washed and dried to yield 0.5 g of the title compound.

$C_{25}H_{20}N_2O_2$
M.P.=160–161° C.
M.W.=380.45
Elemental analysis: Calcd. C, 78.93; H. 5.30; N, 7.36; Found C, 79.01; H, 5.31; N, 7.27.
I.R. (KBr): 3400; 3265; 1725; 1660; 1640; 1592 cm$^{-1}$.
300 MHz 1H-NMR (DMSO-d6): 9.60 (d, 1H); 8.29 (d, 2H); 8.17 (d, 1H); 8.14 (d, 1H); 8.12 (s, 1H); 7.82 (dd, 1H); 7.65 (dd, 1H); 7.61–7.51 (m, 5H); 7.48–7.36 (m, 3H); 2.19 (s, 3H).
MS (EI; source 200° C; 70 eV; 200 μA): 380 (M+.); 337; 232: 204.

EXAMPLE 97

(R,S)-N-[α-(2-Hydroxyethyl)benzyl]-2-phenylquinoline-4-carboxamide 0.7 g (1.7 mmol) of (R,S)-N-[α-(methoxycarbonylmethyl)benzyl]-2-phenylquinoline-4-carboxamide (compound of Ex. 15) were dissolved, under nitrogen athmosphere, in 50 ml of r-BuOH and 2 ml of MeOH.

60 mg (1.6 mmol) of $NaBH_4$ were added in 15 minutes to the boiling solution. The reaction mixture was refluxed for 6 hours, quenched with 5 ml of saturated solution of $NH_4Cl$ and then evaporated in vacuo to dryness. The residue was dissolved in $CH_2Cl_2$ and washed with brine: the organic layer was separated, dried over $Na_2SO_4$ and evaporated in vacuo to dryness.

The crude product was flash chromatographed on 230–400 mesh silica gel, eluting with $Et_2O$ containing 0.5% of conc. $NH_4OH$ and then crystallized from i-PrOH to yield 0.19 g of the title compound.

$C_{25}H_{22}N_2O_2$
M.P.=167–169° C.
M.W.=382.47
Elemental analysis: Calcd. C, 78.52; H, 5.80; N, 7.32; Found C, 78.49; H, 5.79; N, 7.29.
I.R. (KBr): 3360; 1650; 1592 cm$^{-1}$.
300 MHz 1H-NMR (DMSO-d6): 9.30 (d, 1H); 8.31 (d, 2H); 8.13 (d, 1H); 8.10 (s, 1H); 8.03 (d, 1H); 7.81 (dd, 1H); 7.64–7.51 (m, 4H); 7.46 (d, 2H); 7.39 (dd, 2H); 7.29 (dd, 1H); 5.30 (dt, 1H); 4.61 (t, 1H); 3.61–3.41 (m, 2H); 2.11–1.86 (m, 2H).
MS (EI: source 200° C.; 70 eV; 200 μA): 382 (M+.); 337; 232; 204.

EXAMPLE 98

(S)-N-(α-Ethylbenzyl)-3-(2-dimethylaminoethoxy)-2-phenylquinoline-4-carboxamide hydrochloride 0.62 g (1.6 mmol) of (S)-N-(α-ethylbenzyl)-3-hydroxy-2-phenylquinoline-4-carboxamide (compound of Ex. 85) were dissolved in 30 ml of dry DMF.

0.58 g (4.0 mmol) of dimethylaminoethylchloride hydrochloride and 0.56 g (4.0 mmol) of $K_2CO_3$ were added and the reaction mixture was refluxed for 20 hours. The $K_2CO_3$ was filtered off and the mixture was evaporated in vacuo to dryness, dissolved in AcOEt and washed with $H_2O$ and with 20% citric acid. The aqueous layer was made alkaline with 2 N NaOH and extracted with EtOAc; the organic layer was washed with brine, separated, dried over $Na_2SO_4$ and evaporated in vacuo to dryness.

The residue was flash chromatographed on 230–400 mesh silica gel, eluting with $CH_2Cl_2/MeOH$ 98:2 containing 0.4% of conc. $NH_4OH$ and then with $CH_2Cl_2/MeOH$ 86:10 containing 0.6% of conc. $NH_4OH$ to yield 85 mg of a crude product which was dissolved in EtOAc and treated with $HCl/Et_2O$ to obtain 75 mg of the title compound.

$C_{29}H_{31}N_3O_2 \cdot HCl$
M.P.=70° C. dec.
M.W.=490.05
I.R. (nujol): 3600; 3100; 1650; 1550 cm$^{-1}$.
300 MHz 1H-NMR (DMSO-d6): 10.28 (s br, 1H); 9.50 (d, 1H); 8.10 (d, 1H); 7.96 (dd, 2H); 7.78 (m, 1H); 7.67–7.61 (m, 2H); 7.61–7.51 (m, 3H); 7.49–7.39 (m, 4H); 7.33 (dd, 1H); 5.08 (dt, 1H); 3.90 (t, 2H); 2.96 (dt, 2H); 2.49 (s, 6H); 1.85 (m, 2H); 0.97 (t, 3H).
MS (FAB POS, thioglycerol matrix, Xe gas, 8 KeV, source 50° C.): 454 (MH+)

EXAMPLE 99

(S)-N-(α-Ethylbenzyl)-3-acetylamino-2-phenylquinoline-4-carboxamide 0.40 g (1.05 mmol) of (S)-N-(α-ethylbenzyl)-3-amino-2-phenylquinoline-4-carboxamide (compound of Ex. 69) were heated in 25 ml of acetic anhydride at 70° C. for 1 hour and then at 100° C. for additional 3 hours.

The reaction mixture was then evaporated in vacuo to dryness and the residue dissolved in ErOAc; the solution was washed with water, saturated solution of $NaHCO_3$, brine, dried over $Na_2SO_4$ and evaporated in vacuo to dryness.

The crude product (0.39 g) was purified by silica gel flash column chromatography, eluting with a mixture of hexane/EtOAc/conc. $NH_4OH$, 70:30:0.5, respectively, to afford 0.2 g of a pure compound which was recrystallized from acetone to yield 0.14 g of the title compound.

$C_{27}H_{25}N_3O_2$

M.P.=268–269° C.

M.W.=423.52

Elemental analysis: Calcd. C, 76.57; H, 5.95; N, 9.92; Found C. 76.38; H, 5.98; N, 9.90.

I.R. (KBr): 3230; 1670; 1640; 1555; 1525 $cm^{-1}$.

300 MHz 1H-NMR (DMSO-d6): 9.65 (s, 1H); 9.05 (d, 1H); 8.10 (d, 1H); 7.80 (t, 1H); 7.70–7.50 (m, 4H); 7.45–7.20 (m, 8H); 5.08 (dt, 1H); 1.85 (m, 2H); 1.60 (s, 3H); 0.97 (t, 3H).

MS (EI; source 200° C.; 70 eV; 200 µA): 423 (M+.); 381; 334; 289; 261; 247; 218.

EXAMPLE 100

(−)-(S)-N-(α-Ethylbenzyl)-3-(3-dimethylaminopropoxy)-2-phenylquinoline-4-carboxamide hydrochloride 1.2 g (3.1 mmol) of (−)-(S)-N-(α-ethylbenzyl)-3-hydroxy-2-phenylquinoline-4-carboxamide (compound of Ex. 85) were dissolved in 15 ml of dry THF.

1.0 g (8.2 mmol) of 3-dimethylaminopropylchloride, dissolved in 10 ml of ERGO, 1.3 g (9.4 mmol) of $K_2CO_3$ and 0.16 g of KI were added and the reaction mixture was stirred at room temperature for 30 minutes and then refluxed for 2 hours.

Further 0.77 g (6.3 mmol), 1.0 g (8.2 mmol), 0.6 g (4.9 mmol) and additional 0.6 g (4.9 mmol) of 3-dimethylaminopropylchloride, dissolved each time in 10 ml of $Et_2O$, and some KI were added every 12 hours and the reaction refluxed.

The $K_2CO_3$ was filtered off and the mixture was evaporated in-vacuo to dryness, dissolved in EtOAc and washed with HO and with 20% citric acid. The aqueous layer was made alkaline with 2 N NaOH and extracted with EtOAc; the organic layer was washed with brine, separated, dried over $Na_2SO_4$ and evaporated in-vacuo to dryness.

The residue was flash chromatographed on 230–400 mesh silica gci: eluting with $CH_2Cl_2$/MeOH 95: 5 containing 0.5% of conc. $NH_4OH$ to yield 0.9 all of a crude product which was dissolved in EtOAc and treated with $HCl/Et_2O$ to obtain 0.62 g of the title compound.

$C_{30}H_{33}N_3O_2$.HCl

M.P.=108° C. dec.

M.W.=504.08

$[\alpha]_D^{20}$=−16.0 (c=0.5, MeOH)

I.R. (KBr): 3400: 3080: 1655; 1545 $cm^{-1}$.

300 MHz $^1$H-NMR (DMSO-$d_6$): δ 10.55 (s br, 1H); 9.35 (d, 1H); 8.09 (d, 1H); 7.92 (dd, 2H); 7.76 (ddd, 1H); 7.65–7.51 (m, 5H); 7.48–7.40 (m, 4H); 7.31 (dd, 1H); 5.10 (dt, 1H); 3.72–3.62 (m, 2H); 2.75–2.60 (m, 2H); 2.58 (d, 3H); 2.56 (d, 3H); 1.90–1.67 (m, 4H); 1.00 (t, 3H).

MS (EI; source 180° C.; 70 V; 200 mA): 467 (M+.); 466: 395: 58.

EXAMPLE 101

(−)-(S)-N-(α-Ethylbenzyl)-3-[2-(phthalimido)ethoxy]-2-phenylquinoline-4-carboxamide hydrochloride 1.9 g (5.0 mmol) of (−)-(S)-N-(α-ethylbenzyl)-3-hydroxy-2-phenylquinoline-4-carboxamide (compound of Ex. 85) were dissolved in 20 ml of dry THF.

3.8 g (14.9 mmol) of 2-phthalimidoethylbromide, dissolved in 15 ml of THF, 2.0 g (14.5 mmol) of $K_2CO_3$ and 0.25 g of KI were added and the reaction mixture was stirred at room temperature for 2.5 hours and then refluxed for 2 hours.

1.9 g (7.4 mmol) of 2-phthalimidoethylbromide and some KI were added and the reaction was refluxed for additional 3.5 hours.

0.5 g (2.0 mmol) of 2-phthalimidoethylbromide and some KI were added again and the mixture was refluxed for 5 hours.

The $K_2CO_3$ was filtered off and the mixture was evaporated in-vacuo to dryness, dissolved in $CH_2Cl_2$ and washed with $H_2O$. The organic layer was dried over $Na_2SO_4$ and evaporated in-vacuo to dryness.

The residue was flash chromatographed on 230–400 mesh silica gel, eluting with hexane/EtOAc 80:20 containing 0.5% of conc. $NH_4OH$ and then hexane/EtOAc 60:40 containing 0.5% of conc. $NH_4OH$ to afford 2.6 g of a purified product which was triturated with $iPr_2O$ to yield 2.5 g of the title compound.

$C_{35}H_{29}N_3O_4$

M.P.=172–175° C.

M.W.=555.64

$[\alpha]_D^2$=−16.3 (c=0.5, MeOH)

I.R. (KBr): 3280; 3060; 2960; 1780; 1715; 1660; 1530 $cm^{-1}$.

300 MHz $^1$H-NMR (DMSO-$d_6$): δ 9.27 (d, 1H); 8.03 (d, 1H); 7.92–7.84 (m, 4H); 7.78–7.69 (m. 3H); 7.60–7.53 (m, 2H); 7.46–7.38 (m, 4H); 7.27 (dd, 1H); 7.13–7.04 (m, 3H); 4.96 (dt, 1H); 3.92–3.78 (m, 2H); 3.72–3.55 (m, 2H); 1.78 (dq, 2H); 0.93 (t, 3H).

MS (EI; source 180° C.; 70 V; 200 mA): 555 (M+.), 526, 421, 174.

EXAMPLE 102

(−)-(S)-N-(α-Ethylbenzyl)-3-(2-aminoethoxy)-2-phenylquinoline-4-carboxamide hydrochloride 2.2 g (3.9 mmol) of (−)-(S)-N-(α-ethylbenzyl)-3-[2-(phthalimido)ethoxy]-2-phenyl quinoline-4-carboxamide hydrochloride (compound of Ex. 101) were dissolved in 150 ml of 96% EtOH and 0.38 ml (7.8 mmol) of hydrazine hydrate were added to the boiling solution, which was then refluxed for 4 hours.

Further 0.4 ml (8.2 mmol), 0.2 ml (4.1 mmol), 0.2 ml (4.1 mmol), 0.4 ml (8.2 mmol) and 0.4 ml (8.2 mmol) of hydrazine hydrate were added every 12 hours and the reaction mixture was maintained refluxed.

The reaction mixture was then evaporated in-vacuo to dryness, dissolved in 20 ml $H_2O$, cooled and acidified with 10 ml conc. HCl.

The mixture was boiled for 1 hour and cooled, the phthalydrazide was filtered off.

The aqueous layer was washed with EtOAc and then made alkaline with N NaOH and extracted with EtOAc; the organic layer was washed with brine, separated, dried over $Na_2SO_4$ and evaporated in-vacuo to dryness.

The residue was flash chromatographed on 230–400 mesh silica gel, eluting with EtOAc/MeOH 96:4 containing 1.2% of conc. $NH_4OH$ to afford a purified product which was dissolved in EtOAc and treated with $HCl/Et_2O$ to yield 1.2 g of the title compound.

$C_{27}H_{27}N_3O_2 \cdot HCl$
M.P.=119° C. dec.
M.W.=462.00
$[\alpha]_D^{20}=-19.4$ (c=0.5, MeOH)
I.R. (KBr): 3400; 3080; 1640; 1545 cm$^{-1}$.
300 MHz $^1$H-NMR (DMSO-d$_6$): δ 9.45 (d, 1H); 8.09 (d, 1H); 8.00 (dd, 1H); 7.94 (s br, 3H); 7.76 (ddd, 1H); 7.65–7.51 (m, 4H); 7.48–7.40 (m, 3H); 7.31 (dd, 1H); 5.09 (dt, 1H); 3.83 (t, 2H); 2.72 (m, 2H); 1.93–1.80 (m, 2H); 0.99 (t, 3H).
MS (FAB POS, thioglycerol matrix; Xe gas, 8 keV; source 50° C.): 426 (MH+).

EXAMPLE 103

(+)-(S)-N-(α-Ethylbenzyl)-3-[2-(1-pyrrolidinyl)ethoxy]-2-phenylquinoline-4-carboxamide hydrochloride 2.0 g (5.2 mmol) of (−)-(S)-N-(α-ethylbenzyl)-3-hydroxy-2-phenylquinoline-4-carboxamide (compound of Ex. 85) were dissolved in 25 ml of dry THF.

1.0 g (7.5 mmol) of 2-pyrrolidinoethylchloride and 2.2 g (15.9 mmol) of $K_2CO_3$ were added and the reaction mixture was stirred at room temperature for 30 minutes and then refluxed, 1.1 g (8.2 mmol) of 2-pyrrolidinoethylchloride were added to the boiling solution which was refluxed overnight.

The $K_2CO_3$ was filtered off and the mixture was evaporated in-vacuo to dryness, dissolved in EtOAc and washed with $H_2O$ and 20% citric acid. The aqueous layer was made alkaline with 2 N NaOH and extracted with EtOAc; the organic layer was washed with brine, separated, dried over $Na_2SO_4$ and evaporated in-vacuo to dryness.

The residue was flash chromatographed on 230–400 mesh silica gel, eluting with $CH_2Cl_2$/MeOH 97:3 containing 0.5% of conc. $NH_4OH$ to yield 1.8 g of a purified product which was dissolved in EtOAc and treated with $HCl/Et_2O$ to yield 2.0 g of the title compound.

$C_{31}H_{33}N_3O_2 \cdot HCl$
M.P.=110–115° C. (dec.)
M.W.=516.08
$[\alpha]_D^{20}=+4.5$ (c=0.5, MeOH)
I.R. (KBr): 3400; 3080; 1655; 1545 cm$^{-1}$.
300 MHz $^1$H-NMR (DMSO-d$_6$): δ 10.50 (s br, 1H); 9.50 (d, 1H); 8.10 (d, 1H); 7.96 (dd, 2H); 7.78 (ddd, 1H); 7.68–7.30 (m, 10H); 5.10 (dt, 1H); 3.90 (m, 2H); 3.20 (m, 2H); 3.00 (m, 2H); 2.65 (m, 2H); 1.95–1.65 (m, 6H); 1.94 (t, 3H).
MS (EI; source 180° C.; 70 V; 200 mA): 479 (M+.); 478; 383; 97; 84.

EXAMPLE 104

(−)-(S)-N-(α-Ethylbenzyl)-3-(dimethylaminoacetylamino)-2-phenylquinoline-4-carboxamide 1.1 g (2.8 mmol) of (−)-(S)-N-(α-ethylbenzyl)-3-amino-2-phenylquinoline-4-carboxamide (compound of Ex. 69) were dissolved, under nitrogen atmosphere, in 10 ml of warm toluene. 0.96 g (5.6 mmol) of chloroacetic anhydride, dissolved in 5 ml of toluene, were dropped and the solution was refluxed for 1 hour.

The reaction mixture was evaporated in-vacuo to dryness, suspended in 10 ml of $CH_2Cl_2$ and dropped in 5 ml of ice-cooled 28% $Me_2NH$/EtOH.

The solution was stirred at room temperature overnight, then 15 ml of 28% $Me_2NH$/EtOH were added and the reaction mixture was heated at 60° C. in a parr apparatus.

The mixture was evaporated in-vacuo to dryness, dissolved in 20% citric acid and washed with EtOAc. The aqueous layer was basified with 2 N NaOH and extracted with EtOAc; the organic layer was washed with brine, separated, dried over $Na_2SO_4$ and evaporated in-vacuo to dryness to afford 1.4 g of the crude product.

This product was triturated with warm i-$Pr_2O$ to yield 0.86 g of the title compound.

$C_{29}H_{30}N_4O_2$
M.P.=189–191° C.
M.W.=466.59
$[\alpha]_D^{20}=-63.1$ (c=0.5, MeOH)
I.R. (KBr): 3230; 3180; 1670; 1630; 1540 cm$^{-1}$.
300 MHz $^1$H-NMR (DMSO-d$_6$): δ 9.41 (s, 1H); 8.97 (d, 1H), 8.08 (d, 1H); 7.81 (dd, 1H); 7.70–7.59 (m, 4H); 7.49–7.26 (m, 8H); 5.00 (dt, 1H); 2.55 (s, 2H); 1.97 (s, 3H); 1.90–1.65 (m, 2H); 0.93 (t, 3H).
MS (EI; source 180° C.; 70 V; 200 mA): 466 (M+.); 331; 58.

EXAMPLE 105

N-(α,α-Dimethylbenzyl)-3-hydroxy-2-phenylquinoline-4-carboxamide 2.0 g (7.5 mmol) of 3-hydroxy-2-phenylquinoline-4-carboxylic acid were dissolved, under nitrogen atmosphere, in 70 ml of dry THF and 30 ml of $CH_3CN$.

1.02 g (7.5 mmol) of cumylamine and 1.12 g (8.3 mmol) of N-hydroxybenzotriazole (HOBT) were added and the reaction mixture was cooled at −10° C.

1.71 g (8.3 mmol) of DCC, dissolved in 20 ml of $CH_2Cl_2$, were added dropwise and the solution was kept at −5°–0° C. for 2 hours and then at room temperature overnight. The precipitated dicyclohexylurea was filtered off and the solution evaporated in-vacuo to dryness. The residue was dissolved in $CH_2Cl_2$ and washed with $H_2O$, sat. sol. $NaHCO_3$, 5% citric acid, sat. sol. $NaHCO_3$ and brine.

The organic layer was separated, dried over $Na_2SO_4$ and evaporated in-vacuo to dryness; the residue was dissolved in 20 ml of $CH_2Cl_2$ and left overnight. Some more dicyclohexylurea precipitated and was filtered off. The solution was evaporated in-vacuo to dryness to obtain 1.4 g of a crude product which was flash chromatographed on 230–400 mesh silica gel, eluting initially with hexane/EtOAc 9/1 and then hexane/EtOAc 8/2 to afford 0.4 g of the purified product which was recrystallized twice from i-PrOH to yield 0.15 g of the title compound.

$C_{25}H_{22}N_2O_2$
M.P.=166–169° C. dec.
M.W.=382.47
I.R. (nujol): 3200; 1650; 1580; 1535 cm$^{-1}$.
300 MHz $^1$H-NMR (DMSO-d$_6$): δ 9.56 (s, 1H); 8.92 (s br, 1H); 8.00–7.94 (m, 3H); 7.76 (d br, 1H); 7.63–7.45 (m, 7H); 7.36 (dd; 2H); 7.24 (dd, 1H); 1.72 (s, 6H).

MS (EI; source 180° C.; 70 V; 200 mA): 382 (M+.); 264; 247; 219; 119.

EXAMPLE 106

N-(α,α-Dimethylbenzyl)-3-amino-2-phenylquinoline-4-carboxamide 2.0 g (7.6 mmol) of 3-amino-2-phenylquinoline-4-carboxylic acid were dissolved, under nitrogen atmosphere, in 70 ml of dry THF and 30 ml of $CH_3CN$.

1.02 g (7.6 mmol) of cumylamine and 1.12 g (8.3 mmol) of N-hydroxybenzotriazole (HOBT) were added and the reaction mixture was cooled at −10° C.

1.72 g (8.3 mmol) of DCC, dissolved in 20 ml of $CH_2Cl_2$, were added dropwise and the solution was kept at −5°–0° C. for 2 hours and then at room temperature overnight. The precipitated dicyclohexylurea was filtered off and the solution evaporated in-vacuo to dryness. The residue was dissolved in $CH_2Cl_2$ and washed with $H_2O$, sat. sol. $NaHCO_3$, 5% citric acid, sat. sol. $NaHCO_3$ and brine.

The organic layer was separated, dried over $Na_2SO_4$ and evaporated in-vacuo to dryness; the residue was dissolved in 20 ml of $CH_2Cl_2$ and left overnight. Some more dicyclohexylurea precipitated and was filtered off. The solution was evaporated in-vacuo to dryness to obtain 2.0 g of a crude product which was flash chromatographed on 230–400 mesh silica gel, eluting with hexane/EtOAc 6/4 containing 1% of conc. $NH_4OH$ to afford 0.9 g of the purified product which was recrystallized from hexane/EtOAc 1/1 and then from i-PrOH to yield 0.45 g of the title compound.

$C_{25}H_{23}N_3O$
M.P. 166–168° C.
M.W.=381.48
I.R. (nujol): 3460; 3360; 3220; 1667; 1605; 1527 cm$^{-1}$.
300 MHz $^1$H-NMR (DMSO-d$_6$): δ 9.05 (s, 1H); 7.87 (dd, 1H); 7.74–7.68 (m, 3H); 7.60–7.42 (m, 7H); 7.37 (dd, 2H); 7.24 (dd, 1H); 4.74 (s, 2H); 1.71 (s, 6H).
MS (EI; source 180° C.; 70 V; 200 mA): 381 (M+.); 263; 218; 119.

EXAMPLE 107

(−)-(S)-N-(α-Ethylbenzyl)-5-methyl-2-phenylquinoline-4-carboxamide 0.80 g (3.04 mmol) of 5-methyl-2-phenylquinoline-4-carboxylic acid were dissolved, under nitrogen atmosphere, in 30 ml of dry THF and 12 ml of $CH_3CN$.

0.43 g (3.20 mmol) of (S)-(−)-α-ethylbenzylamine and 0.78 g (5.78 mmol) of N-hydroxybenzotriazole (HOBT) were added and the reaction mixture was cooled at −10° C.

0.69 g (3.34 mmol) of DCC, dissolved in 5 ml of $CH_2Cl_2$, were added dropwise and the solution was kept at −5°–0° C. for 2 hours and then at room temperature overnight. The precipitated dicyclohexylurea was filtered off and the solution evaporated in-vacuo to dryness. The residue was dissolved in $CH_2Cl_2$ and washed with $H_2O$, sat. sol. $NaHCO_3$, 5% citric acid, sat. sol. $NaHCO_3$ and brine.

The organic layer was separated, dried over $Na_2SO_4$ and evaporated in-vacuo to dryness; the residue was dissolved in 10 ml of $CH_2Cl_2$ and left overnight. Some more dicyclohexylurea precipitated and was filtered off. The solution was evaporated in-vacuo to dryness to obtain 1.15 g of a crude product which was flash chromatographed on 230–400 mesh silica gel, eluting with hexane/EtOAc 6/2 containing 0.5% of conc. $NH_4OH$ to afford 0.47 g of the purified product which was recrystallized from i-Pr$_2$O containing some drops of EtOAc to yield 0.36 g of the title compound as a white powder.

$C_{26}H_{24}N_2O$
M.P.=189–192° C.
M.W.=380.49
=−3.8 (c=0.5, MeOH)
I.R. (KBr): 3280; 3070; 3020; 1635; 1545 cm$^{-1}$.
300 MHz $^1$H-NMR (DMSO-d$_6$): δ 9.20 (d, 1H); 8.23 (d, 2H); 7.93 (d, 1H); 7.78 (s, 1H); 7.20–7.7I0 (m, 10H); 5.00 (dt, 1H); 2.38 (s broad, 3H); 1.70–1.90 (m, 2H); 0.95 (t, 3H).
MS (EI; source 180° C.; 70 V; 200 mA): 380 (Ml+.); 246; 218.

EXAMPLE 108

(R,S)-N-[α-(1-Hydroxyethyl)benzyl]-3-methyl-2-phenylquinoline-4-carboxamide

Prepared as described in Ex. 1, starting from 11.08 g (39.33 mmol) of crude 3-methyl-2-phenylquinoline-4-carbonylchloride, 4.87 g (32.20 mmol) of 1-phenyl-2-hydroxypropylamine and 10.33 ml (74.14 mmol) of TEA in 150 ml of a 1:1 mixture of dry $CH_2Cl_2$ and $CH_3CN$.

The precipitated TEA hydrochloride was filtered off and the filtrate concentrated in-vacuo to dryness; the residue was dissolved in $CH_2Cl_2$ (100 ml) and washed with a sat. sol. of $NaHCO_3$, 20% citric acid and brine. The organic solution was dried over $Na_2SO_4$ and evaporated in-vacuo to dryness to obtain 13.23 g of an oil, which was crystallized from i-PrO$_2$ (100 ml) containing 6 ml of i-PrOH to yield 9.14 g of the title compound as an off-white solid.

$C_{26}H_{24}N_2O_2$
M.P.=163–165° C.
M.W.=396.49
I.R. (nujol): 3400; 3260; 1635; 1580 cm$^{-1}$.

EXAMPLE 109

(R,S)-N-[α-(Methylcarbonyl)benzyl]-3-methyl-2-phenylquinoline-4-carboxamide

Prepared as described in Example 96, starting from 3.25 g (25.60 mmol) of oxalyl chloride, 3.88 g (49.66 mmol) of DMSO, 8.2 g (20.68 mmol) of (R,S)-N-[α-(1-hydroxyethyl)benzyl]-3-methyl-2-phenylquinoline-4-carboxamide (compound of Ex. 108) and 15.72 ml (112.76 mmol) of TEA in 230 ml of dry $CH_2Cl_2$.

The reaction was quenched with 40 ml of $H_2O$ and the organic layer separated and washed with 20% citric acid, sat. sol. $NaHCO_3$ and brine. The organic solution was dried over $Na_2SO_4$ and evaporated in-vacuo to dryness to afford 9.4 g of the crude title compound as an oil. This residual oil was flash chromatographed on 230–400 mesh silica gel, eluting with a mixture of hexane/ethyl,acetate 70:30 containing 1% of conc. $NH_4OH$ to afford 7.7 g of the purified product which was crystallized from a mixture of EtOAc/hexane 1:3 respectively, to yield 6.0 g of the pure title compound.

$C_{26}H_{22}N_2O_2$
M.P.=156–158° C.
M.W.=394.48
I.R. (nujol): 3270; 3180; 1735; 1725; 1660; 1630; 1527; 1460 cm$^{-1}$.
300 MHz $^1$H-NMR (DMSO-d$_6$): δ 9.53 (d, 1H); 8.01 (d, 1H); 7.73 (dd, 1H); 7.62–7.35 (m, 12H); 5.97 (d, 1H); 2.30 (s br, 3H); 2.18 (s, 3H).

MS (EI; source 180° C.; 70 V; 200 mA): 394 (M+.); 352: 351; 246; 218; 217.

EXAMPLE 110

(R,S)-N-[α-(Ethyl)-4-pyridylmethyl]-2-phenylquinoline-4-carboxamide 4.12 g (16.52 mmol) of 2-phenylquinoline-4-carboxylic acid were dissolved, under nitrogen atmosphere, in 40 ml of dry $CH_2Cl_2$ and 30 ml of THF. 1.50 g (11.01 mmol) of 1-(4-pyridyl)-n-propyl amine and 2.23 g (16.52 mmol) of N-hydroxybenzotriazole (HOBT) were added and the reaction mixture was cooled at 0° C.

3.41 g (16.52 mmol) of DCC, dissolved in 26 ml of dry $CH_2Cl_2$, were added dropwise and the solution was kept at 0° C. for 2 hours and then stirred at room temperature for 36 hours. The precipitated dicyclohexylurea was filtered off and the solution evaporated in-vacuo to dryness. The residue was dissolved in 100 ml of $CH_2Cl_2$ and washed with $H_2O$, 10% $K_2CO_3$, 5% citric acid and brine.

The organic layer was separated, dried over $Na_2SO_4$ and evaporated in-vacuo to dryness; the residue was dissolved in 30 ml of $CH_2Cl_2$ and left overnight. Some more dicyclohexylurea precipitated and was filtered off. The solution was evaporated in-vacuo to dryness to obtain 3.5 g of a crude product which was recrystallized three times from i-PrOH to yield 0.91 g of the title compound.

$C_{24}H_{21}N_3O$

M.P.=218–219° C.

M.W.=367.45

I.R. (KBr): 3260; 3060; 1648; 1595; 1545; 1350 $cm^{-1}$.

300 MHz $^1$H-NMR (DMSO-$d_6$): δ 9.33 (d, 1H); 8.58 (d, 2H); 8.33 (dd, 2H); 8.15 (d, 1H); 8.14 (s, 1H); 8.03 (d, 1H); 7.82 (dd, 1H); 7.6–7.52 (m, 4H); 7.47 (d, 2H); 5.05 (dt, 1H); 1.85 (dq, 2H); 1.00 (t, 3H).

MS (EI; source 180° C.; 70 V; 200 mA): 367 (M+.); 338; 232; 204.

EXAMPLE 111

(R,S)-N-[α-(Ethyl)-2-thienylmethyl]-2-phenylquinoline-4-carboxamide 1.40 g (8.00 mmol) of 1-(2-thienyl)-n-propyl amine hydrochloride and 2.45 ml (17.60 mmol) of TEA were dissolved, under nitrogen atmosphere, in 50 ml of dry $CH_2Cl_2$ and 30 ml of $CH_3CN$.

2.0 g (8.00 mmol) of 2-phenylquinoline-4-carboxylic acid and 1.30 g (9.60 mmol) of N-hydroxybenzotriazole (HOBT) were added.

2.48 g (12.00 mmol) of DCC, dissolved in 30 ml of dry $CH_2Cl_2$, were added dropwise and the solution was stirred at room temperature for 36 hours. 50 ml of 10% HCl were added and the solution stirred for aditional 2 hours. The precipitated dicyclohexylurea was filtered off and the organic layer washed with 10% citric acid and 10% $K_2CO_3$.

The organic layer was separated, dried over $Na_2SO_4$ and evaporated in-vacuo to dryness. The crude product was flash chromatographed on 230–400 mesh silica gel, eluting with a mixture of hexane/EtOAc/$CH_2Cl_2$ 80:15:0.5 to afford 2.0 g of a yellow oil which was crystallized from a mixture of toluene/hexane to yield 0.9 g of the pure title compound as white crystals.

$C_{23}H_{20}N_2OS$

M.P.=134–137° C.

M.W.=372.49

I.R. (KBr): 3230; 3060; 1630; 1590; 1545 $cm^{-1}$.

300 MHz $^1$H-NMR (DMSO-$d_6$): δ 9.33 (d, 1H); 8.30 (dd, 2H); 8.15 (d, 1H); 8.13 (d, 1H); 8.08 (s, 1H); 7.84 (ddd, 1H); 7.68–7.51 (m, 4H); 7.44 (dd, 1H); 7.11 (d, 1H); 7.02 (dd, 1H); 5.33 (dt, 1H); 2.10–1.88 (m, 2H); 1.05 (t, 3H).

MS (EI; source 180° C.; 70 V; 200 mA): 372 (M+.); 343; 232; 204.

EXAMPLE 112

(+)-(S)-N-(α-Ethylbenzyl)-3-dimethylaminomethyl-2-phenylquinoline-4-carboxamide hydrochloride 5.60 g (21.27 mmol) of 3-methyl-2-phenylquinoline-4-carboxylic acid were dissolved in 100 ml of dichloromethane.

7.60 g (42.50 mmol) of N-bromosuccinimide and 0.52 g (2.00 mmol) of dibenzoyl peroxide were added and the solution refluxed for 24 hours.

The reaction mixture was evaporated in-vacuo to dryness, suspended in 100 ml of 33% $Me_2NH/EtOH$ and stirred overnight at room temperature.

The solution was evaporated in-vacuo to dryness, dissolved in 50 ml of 20% $K_2CO_3$ and evaporated again in-vacuo to dryness. 50 ml of water were added to the residue and the solution, acidified with 37% HCl, was evaporated in-vacuo to dryness.

The crude residue and 10.8 ml (77.20 mmol) of TEA were dissolved in 50 ml of $CH_2Cl_2$, 50 ml of THF and 100 ml of $CH_3CN$.

3.00 g (22.20 mmol) of (S)-(-)-α-ethylbenzylamine, 0.78 g (5.78 mmol) of N-hydroxybenzotriazole (HOBT) and 11.9 g (57.90 mmol) of DCC were added and the solution was stirred at room temperature overnight.

The precipitated dicyclohexylurea was filtered off and the organic layer evaporated in-vacuo to dryness.

The brown oily residue was dissolved in 100 ml of $CH_2Cl_2$ and the precipitate was filtered off. The filtrate was extracted three times with 40% citric acid. The acqueous layer, basified with solid $K_2CO_3$, was extracted with $CH_2Cl_2$; the organic solution dried over $Na_2SO_4$ and evaporated in-vacuo to dryness afforded 10 g of a brown oil.

The crude product was flash chromatographed on 230–400 mesh silica gel, eluting with a mixture of i-$Pr_2O$/$CH_2Cl_2$ 9:1 to afford 2.5 g of a white solid which was dissolved in toluene and left overnight.

The DCU precipitated was filtered and the solution, treated with ethanolic HCl, was evaporated in-vacuo to dryness. The crude product was recrystallized from a mixture of toluene/EtOH to yield 0.7 g of the pure title compound as colourless crystals.

$C_{28}H_{29}N_3O \cdot HCl$

M.P.=164–167° C.

M.W.=460.02

$[\alpha]_D^{20}$=+25.3 (c=1, MeOH)

I.R. (KBr): 3440; 3150; 3020; 2560; 2460; 1650; 1540 $cm^{-1}$.

300 MHz $^1$H-NMR (DMSO-$d_6$, 353 K): δ 9.70 (s br, 1H); 8.10 (d, 1H); 7.85 (dd, 1H); 7.80 (s br, 1H); 7.70–7.10 (m, 12H); 5.15 (dt, 1H); 4.38–4.20 (m, 2H); 2.30 (s, 3H); 2.22 (s, 6H); 2.10–1.82 (m, 2H); 1.00 (t, 3H).

MS (EI; source 180° C.; 70 V; 200 mA): 423 (M+.), 380, 288.

EXAMPLE 113

(S)-N-(α-Ethylbenzyl)-3-methyl-7-methoxy-2-phenylquinoline-4-carboxamide

Prepared as described in Ex. 1, starting from 1.27 g (4.09 mmol) of crude 3-methyl-7-methoxy-2-phenylquinoline-4-carbonylchloride, 0.55 g (4.09 mmol) of (S)-(-)-α-ethylbenzylamine and 1.71 ml (12.27 mmol) of TEA in 24 ml of dry $CH_2Cl_2$ and 1 ml of DMF to help solubility. The reaction mixture was stirred 12 hours at room temperture.

After being concentrated in-vacuo to dryness, the residue was dissolved in $CH_2Cl_2$ (30 ml) and washed with 10% $NaHCO_3$, 5% citric acid and brine. The organic solution was dried over $Na_2SO_4$ and evaporated in-vacuo to dryness to obtain 1.87 g of a crude product, which was flash chromatographed on 230–400 mesh silica gel, eluting with a mixture of hexane/EtOAc 70:30 to afford 0.350 g of a yellow oil.

$C_{27}H_{26}N_2O_2$

M.W.=410.51

I.R. (KBr): 3240; 2965; 2930; 1635; 1535; 1220 $cm^{-1}$.

EXAMPLE 114

(S)-N-(α-Ethylbenzyl)-3-amino-5-methyl-2-phenylquinoline-4-carboxamide 0.75 g (2.64 mmol) of 3-amino-5-methyl-2-phenylquinoline-4-carboxylic acid were dissolved, under nitrogen atmosphere, in 30 ml of dry THF and 10 ml of $CH_3CN$.

0.38 g (2.83 mmol) of (S)-(-)-α-ethylbenzylamine and 0.69 g (5.18 mmol) of N-hydroxybenzotriazole (HOBT) were added and the reaction mixture was cooled at −10° C.

0.61 g (2.97 mmol) of DCC, dissolved in 5 ml of $CH_2Cl_2$, were added dropwise and the solution was kept at −5°–0° C. for 2 hours, heated at 50° C. for 4 hours and then left at room temperature overnight.

The precipitated dicyclohexylurea was filtered off and the solution evaporated in-vacuo to dryness. The residue was dissolved in $CH_2Cl_2$ and washed with $H_2O$, sat. sol. $NaHCO_3$, 5% citric acid, sat. sol. $NaHCO_3$ and brine.

The organic layer was separated, dried over $Na_2SO_4$ and evaporated in-vacuo to dryness; the residue was dissolved in 10 ml of $CH_2Cl_2$ and left overnight. Some more dicyclohexylurea precipitated and was filtered off. The solution was evaporated in-vacuo to dryness to obtain 0.86 g of a crude product which was flash chromatographed on 230–400 mesh silica gel, eluting with $CH_2Cl_2$/MeOH/conc. $NH_4OH$, 90:10:0.5 respectively, to afford 0.41 g of the title compound as an oil.

$C_{26}H_{25}N_3O$

M.W.=395.50

I.R. (KBr): 3480; 3390; 3230; 3020; 1635; 1615; 1545 $cm^{-1}$.

EXAMPLE 115

(S)-N-(α-Ethylbenzyl)-3-methoxy-5-methyl-2-phenylquinoline-4-carboxamide 1.29 g (4.40 mmol) of 3-methoxy-5-methyl-2-phenylquinoline-4-carboxylic acid were dissolved, under nitrogen atmosphere, in 40 ml of dry THF and 20 ml of $CH_3CN$.

0.63 g (4.62 mmol) of (S)-(-)-α-ethylbenzylamine and 1.13 g (8.36 mmol) of N-hydroxybenzotriazole (HOBT) were added and the reaction mixture was cooled at −10° C.

1.0 g (4.84 mmol) of DCC, dissolved in 5 ml of $CH_2Cl_2$, were added dropwise and the solution was kept at −5°–0° C. for 2 hours, heated at 50° C. for 4 hours and then left at room temperature overnight.

The precipitated dicyclohexylurea was filtered off and the solution evaporated in-vacuo to dryness. The residue was dissolved in $CH_2Cl_2$ and washed with $H_2O$, sat. sol. $NaHCO_3$, 5% citric acid, sat. sol. $NaHCO_3$ and brine.

The organic layer was separated, dried over $Na_2SO_4$ and evaporated in-vacuo to dryness; the residue was dissolved in 20 ml of $CH_2Cl_2$ and left overnight. Some more dicyclohexylurea precipitated and was filtered off.

The solution was evaporated in-vacuo to dryness to obtain 2.45 g of a crude product which was flash chromatographed on 230–400 mesh silica gel, eluting with hexane/EtOAc 7:2 containing 0.5% of conc. $NH_4OH$, to afford 0.28 g of the title compound as an oil.

$C_{27}H_{26}N_2O_2$

M.W.=410.52

I.R. (KBr): 3270; 3020; 1635; 1535 $cm^{-1}$.

TABLE 6

Analytical data of compounds of Examples 93–115.

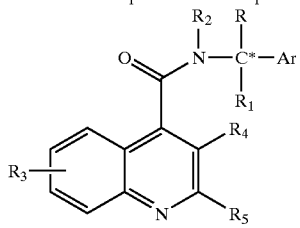

| Ex. | Ar | R | $R_1$ | $R_2$ | $R_3$ | $R_4$ | $R_5$ | * | Molecular formula | Melting point, ° C. | $[\alpha]_D^{20}$ c=0.5 MeOH |
|---|---|---|---|---|---|---|---|---|---|---|---|
| 93 | Ph | COOMe | H | H | H | H | Ph(4-Cl) | (R,S) | $C_{25}H_{19}ClN_2O_3$ | 170–172 | — |
| 94 | Ph(4-OMe) | COOMe | H | H | H | H | Ph | (R) | $C_{26}H_{22}N_2O_4$ | 160–162 | — |
| 95 | Ph | COOMe | Me | Me | H | H | Ph | (R,S) | $C_{27}H_{24}N_2O_3$·HCl | — | — |
| 96 | Ph | COMe | H | H | H | H | Ph | (R,S) | $C_{25}H_{20}N_2O_2$ | 160–161 | — |
| 97 | Ph | $CH_2CH_2OH$ | H | H | H | H | Ph | (R,S) | $C_{25}H_{22}N_2O_2$ | 167–169 | — |
| 98 | Ph | Et | H | H | H | $OCH_2CH_2NMe_2$ | Ph | (S) | $C_{29}H_{31}N_3O_2$·HCl | 70 dec.[a] | —[b] |
| 99 | Ph | Et | H | H | H | NHCOMe | Ph | (S) | $C_{27}H_{25}N_3O_2$ | 268–269 | −71.4 |

TABLE 6-continued

Analytical data of compounds of Examples 93–115.

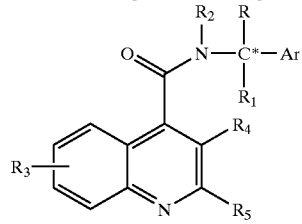

| Ex. | Ar | R | $R_1$ | $R_2$ | $R_3$ | $R_4$ | $R_5$ | * | Molecular formula | Melting point, °C. | $[\alpha]_D^{20}$ c=0.5 MeOH |
|---|---|---|---|---|---|---|---|---|---|---|---|
| 100 | Ph | Et | H | H | H | OCH$_2$CH$_2$CH$_2$NMe$_2$ | Ph | (S) | C$_{30}$H$_{33}$N$_3$O$_2$.HCl | 108 dec. | −16.0 |
| 101 | Ph | Et | H | H | H | OCH$_2$CH$_2$phthalimido | Ph | (S) | C$_{35}$H$_{29}$N$_3$O$_4$ | 172–175 | −16.3 |
| 102 | Ph | Et | H | H | H | OCH$_2$CH$_2$NH$_2$ | Ph | (S) | C$_{27}$H$_{27}$N$_3$O$_2$.HCl | 119 dec. | −19.4 |
| 103 | Ph | Et | H | H | H | OCH$_2$CH$_2$pyrrolidino | Ph | (S) | C$_{31}$H$_{33}$N$_3$O$_2$.HCl | 110–115 | +4.5 |
| 104 | Ph | Et | H | H | H | NHCOCH$_2$NMe$_2$ | Ph | (S) | C$_{29}$H$_{30}$N$_4$O$_2$ | 189–191 | −63.1 |
| 105 | Ph | Me | Me | H | H | OH | Ph | — | C$_{25}$H$_{22}$N$_2$O$_2$ | 166–169 | — |
| 106 | Ph | Me | Me | H | H | NH$_2$ | Ph | — | C$_{25}$H$_{23}$N$_3$O | 166–168 | — |
| 107 | Ph | Et | H | H | 5-Me | H | Ph | (S) | C$_{26}$H$_{24}$N$_2$O | 189–192 | −3.8 |
| 108 | Ph | CH(OH)Me | H | H | H | Me | Ph | (R,S) | C$_{26}$H$_{24}$N$_2$O$_2$ | 163–165 | — |
| 109 | Ph | COMe | H | H | H | Me | Ph | (R,S) | C$_{26}$H$_{22}$N$_2$O$_2$ | 156–158 | — |
| 110 | 4-Py | Et | H | H | H | H | Ph | (R,S) | C$_{24}$H$_{21}$N$_3$O | 218–219 | — |
| 111 | 2-thienyl | Et | H | H | H | H | Ph | (R,S) | C$_{23}$H$_{20}$N$_2$OS | 134–137 | — |
| 112 | Ph | Et | H | H | H | CH$_2$NMe$_2$ | Ph | (S) | C$_{28}$H$_{29}$N$_3$O.HCl | 164–167 | +25.3 |
| 113 | Ph | Et | H | H | 7-MeO | Me | Ph | (S) | C$_{27}$H$_{26}$N$_2$O$_2$ | oil | — |
| 114 | Ph | Et | H | H | 5-Me | NH2 | Ph | (S) | C$_{26}$H$_{25}$N$_3$O | oil | — |
| 115 | Ph | Et | H | H | 5-Me | OMe | Ph | (S) | C$_{27}$H$_{26}$N$_2$O$_2$ | oil | — |

$^a$free base: mp = 141–143;
$^b$free base: $[\alpha]_D^{20}$ = −48.6 (c=0.5, MeOH)

What is claimed is:

1. A method for the treatment of schizophrenia, which method comprises the administration to a mammal in need thereof, of an effective, non-toxic, pharmaceutically acceptable amount of the NK-3 antagonist compound of formula (I):

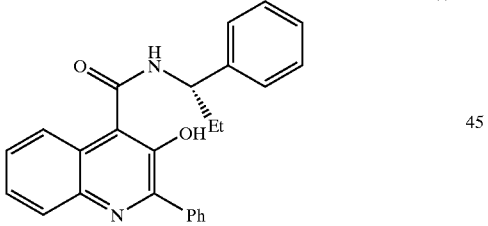

or a pharmaceutically acceptable solvate thereof, or a pharmaceutically acceptable salt thereof.

* * * * *